(12) United States Patent
Iqbal et al.

(10) Patent No.: US 10,570,461 B2
(45) Date of Patent: Feb. 25, 2020

(54) METHODS OF DETECTING TUMOR CELLS

(71) Applicant: BOARD OF REGENTS, THE UNIVERSITY OF TEXAS SYSTEM, Austin, TX (US)

(72) Inventors: Samir M. Iqbal, Euless, TX (US); Swati Goyal, Fremont, CA (US); Young-Tae Kim, Arlington, TX (US); Yuan Wan, Arlington, TX (US); Mohammed A. I. Mahmood, Arlington, TX (US); Umair J. M. Khan, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/201,784

(22) Filed: Nov. 27, 2018

(65) Prior Publication Data

US 2019/0136329 A1 May 9, 2019

Related U.S. Application Data

(60) Division of application No. 14/323,840, filed on Jul. 3, 2014, now Pat. No. 10,155,988, which is a continuation-in-part of application No. 13/081,319, filed on Apr. 6, 2011, now Pat. No. 8,940,663.

(60) Provisional application No. 61/321,770, filed on Apr. 7, 2010.

(51) Int. Cl.
| | |
|---|---|
| *C12N 15/115* | (2010.01) |
| *G01N 33/53* | (2006.01) |
| *C12Q 1/6886* | (2018.01) |
| *G01N 33/574* | (2006.01) |

(52) U.S. Cl.
CPC .......... *C12Q 1/6886* (2013.01); *C12N 15/115* (2013.01); *G01N 33/5308* (2013.01); *G01N 33/57492* (2013.01); *C12Q 2600/112* (2013.01); *G01N 2333/71* (2013.01)

(58) Field of Classification Search
None
See application file for complete search history.

(56) References Cited

PUBLICATIONS

Wan, Yuan et al. "Aptamer-Based Lab-On-Chip for Cancer Cell Isolation and Detection", Proceedings of the 1st Global Congress on NanoEngineering for Medicine and Biology, 2010, NEMB2010-13195; pp. 1-2.*
Wan et al. Cancer Res. vol. 70(22):9371-9380, 2010.*

* cited by examiner

*Primary Examiner* — Sean McGarry
(74) *Attorney, Agent, or Firm* — Christopher S. Dodson; Nexsen Pruet, PLLC

(57) ABSTRACT

In one aspect, methods of detecting tumor cells are described herein. In some embodiments, a method of detecting tumor cells comprises providing a device, the device comprising a substrate surface and a plurality of first aptamer probes attached to the substrate surface. The method further comprises contacting a plurality of cells with the plurality of first aptamer probes attached to the substrate surface; adhering one or more of the plurality of cells to the substrate surface; and measuring a non-uniformity parameter, a Hausdorff distance, a change in the number of pseudopods, and/or a shape of at least one adhered cell. In some cases, the method further comprises using the non-uniformity parameter, Hausdorff distance, change in the number of pseudopods, and/or shape of the adhered cell to identify the adhered cell as a tumor cell or a non-tumor cell.

20 Claims, 36 Drawing Sheets
Specification includes a Sequence Listing.

FIGURE 4A
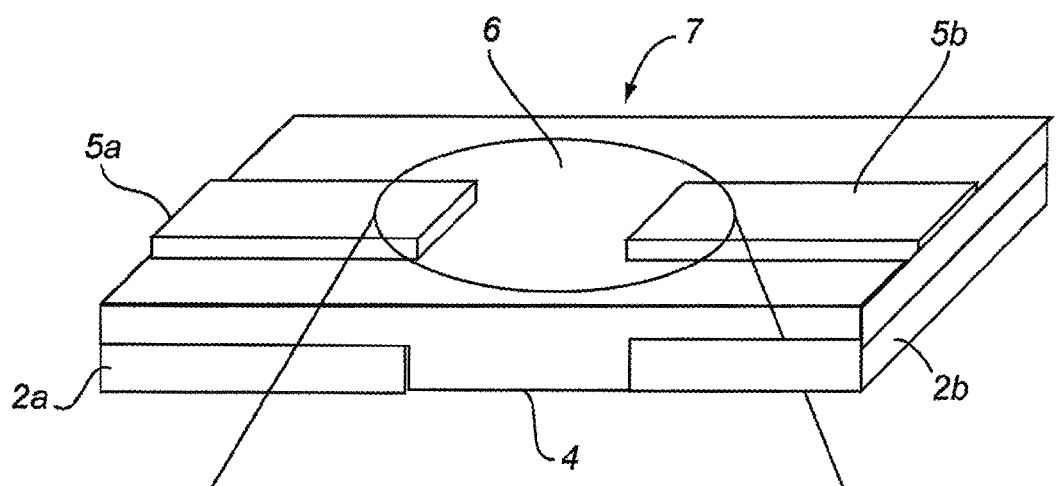
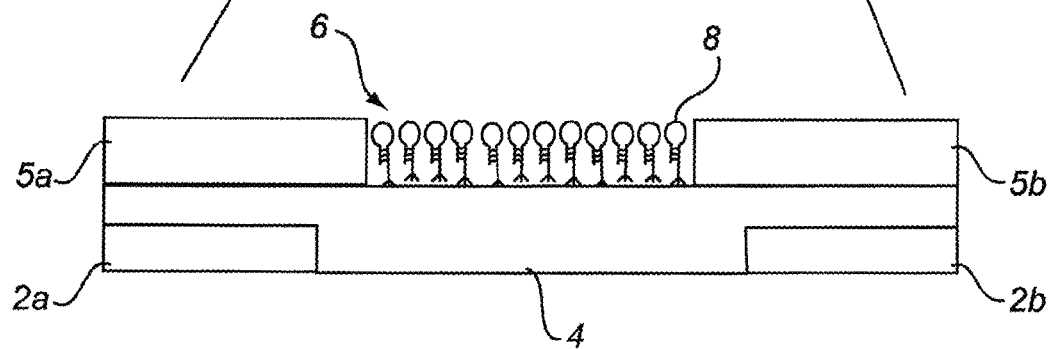
FIGURE 4B (a)

(b)

(c)

(d)

(a)

(b)

```
                        SEQUENCE LISTING

<160> NUMBER OF SEQ ID NOS: 8

<210> SEQ ID NO 1
<211> LENGTH: 117
<212> TYPE: RNA
<213> ORGANISM: Artificial sequence
<220> FEATURE:
<223> OTHER INFORMATION: Synthetic construct

<400> SEQUENCE: 1
ggcgcuccga ccuuagucuc ugugccgcua uaaugcacgg auuuaaucgc cguagaaaag        60
caugucaaag ccggaaccgu guagcacagc agagaauuaa augcccgcca ugaccag         117

<210> SEQ ID NO 2
<211> LENGTH: 117
<212> TYPE: RNA
<213> ORGANISM: Artificial sequence
<220> FEATURE:
<223> OTHER INFORMATION: Synthetic construct

<400> SEQUENCE: 2
ggcgcuccga ccuuagucuc uguucccaca ucaugcacaa ggacaauucu gugcauccaa        60
ggaggaguuc ucggaaccgu guagcacagc agagaauuaa augcccgcca ugaccag         117

<210> SEQ ID NO 3
<211> LENGTH: 117
<212> TYPE: RNA
<213> ORGANISM: Artificial sequence
<220> FEATURE:
<223> OTHER INFORMATION: Synthetic construct

<400> SEQUENCE: 3
ggcgcuccga ccuuagucuc ugugccgcua uaaugcacgg auuuaaucgc cguagaaaag        60
caugucaaag ccggaaccgu guagcacagc agagaauuaa augcccgcca ugaccag         117

<210> SEQ ID NO 4
<211> LENGTH: 117
<212> TYPE: RNA
<213> ORGANISM: Artificial sequence
<220> FEATURE:
<223> OTHER INFORMATION: Synthetic construct

<400> SEQUENCE: 4
ggcgcuccga ccuuagucuc uguucccaca ucaugcacaa ggacaauucu gugcauccaa        60
ggaggaguuc ucggaaccgu guagcacagc agagaauuaa augcccgcca ugaccag         117
```

```
<210> SEQ ID NO 5
<211> LENGTH: 24
<212> TYPE: DNA
<213> ORGANISM: Artificial sequence
<220> FEATURE:
<223> OTHER INFORMATION: Synthetic construct

<400> SEQUENCE: 5
ctggtcatgg cgggcattta attc                                          24

<210> SEQ ID NO 6
<211> LENGTH: 23
<212> TYPE: DNA
<213> ORGANISM: Artificial sequence
<220> FEATURE:
<223> OTHER INFORMATION: Synthetic construct

<400> SEQUENCE: 6
cttaaggtag caaatgcctc gtc                                           23

<210> SEQ ID NO 7
<211> LENGTH: 24
<212> TYPE: DNA
<213> ORGANISM: Artificial sequence
<220> FEATURE:
<223> OTHER INFORMATION: Synthetic construct

<400> SEQUENCE: 7
ctggtcatgg cgggcattta attc                                          24

<210> SEQ ID NO 8
<211> LENGTH: 24
<212> TYPE: DNA
<213> ORGANISM: Artificial sequence
<220> FEATURE:
<223> OTHER INFORMATION: Synthetic construct

<400> SEQUENCE: 8
ctggtcatgg cgggcattta attc                                          24
```

METHODS OF DETECTING TUMOR CELLS

CROSS REFERENCE TO RELATED APPLICATIONS

This application is a divisional application under 35 U.S.C. § 120 of U.S. patent application Ser. No. 14/323,840, filed Jul. 3, 2014, which is a continuation-in-part of U.S. patent application Ser. No. 13/081,319, filed Apr. 6, 2011, which claims priority pursuant to 35 U.S.C. § 119 to U.S. Patent Application Ser. No. 61/321,770, filed Apr. 7, 2010, each of which is hereby incorporated by reference in its entirety.

The sequence listing titled "Sequence Listing" having a file size of 2,204 bytes and filed herewith is incorporated herein by reference as if fully set forth.

STATEMENT REGARDING FEDERALLY SPONSORED RESEARCH

This invention was made with government support under CAREER award contract ECCS 0845669 awarded by the National Science Foundation (NSF). The government has certain rights in the invention.

FIELD

The invention relates generally to devices, systems, and methods for detecting hybridization and/or morphology of proteins and/or cells, including cancer cells, using surface-tethered aptamer probes, without the use of labeling or target modification.

BACKGROUND

Antibodies are commonly used to functionalize nanodevices and nano-objects for detection of specific biomarkers. Such antibody-based molecular recognition has limited capability for field-deployable or point-of-care modalities, as antibodies need a certain range of temperatures, humidity, and solution conditions to retain their structure. In terms of the solution conditions, an important parameter is the need for low ionic strength. Low ionic strength of the buffer solutions is needed to overcome surface Debye screening, but it also results in weak interactions between the surface probe and solution target.

There are other means of protein detection, including amperometric and optical detection, such as those employing microarray technology. Electrical detection methods include capacitive, impedometric, and voltametric detection. In the case of optical detection, a fluorescent tag is usually attached to the DNA or the protein and the change in fluorescent intensity is measured after binding. However, the tagging of the DNA or protein molecule can change the thermodynamic properties of the molecular interactions of DNA and, in some cases, unnaturally stabilize or destabilize the DNA double-strand of the DNA or protein and change the melting temperature significantly. Additionally, expensive fluorescent microscopes are needed to visualize the data and normalization of the data to references remains problematic. Further, the hybridization of the probe and target molecules is a diffusion-limited process requiring long-incubation times as the target molecules must travel to the arrayed probes on the surface of the chip. The fluorophores are also known to have great effect on the stability of the duplexes as a function of the sequence itself. In addition, fluorescent dyes photobleach, quench statically, or interact with each other, so the microarray technologists need to have very detailed knowledge about the limitations of the optics, reagents used, and the sample interactions.

Thus, there is a need for biosensors for proteins and cells, including cancer cells, that integrate sensing, characterization, comparative analysis and decision making all on-board a single chip, while sustaining or increasing sensitivity and specificity. The invention is directed to these, as well as other, important ends.

SUMMARY

The invention provides a nanotechnology-based low-power, rapid, inexpensive, recyclable, and sensitive electrical detection device, system, and method of low concentrations of proteins and cells with no external sample preparation or labeling or other chemical modification of the sample. The biosensors of the invention may be used in wide variety of applications requiring sensitive protein and cell detection, including, but not limited to, cancer cell detection, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

The invention involves a number of features: use of nanoimprint lithography-based techniques to make chips with arrays of nanogap electrodes and embedded heaters for on-chip sample treatment, for recycling of the chip for next batch of targets, and for temperature gradient focusing of the target proteins and cells; use of surface bound linear double-stranded nucleic acid aptamer or hairpin loop nucleic acid probes that are capable of distinguishing between solution phase specific binding and single-base mismatched sequences; use of a nanoparticle conjugated to a short sequence of nucleic acids as a detector to quantify the level of hybridization between probe and target DNA molecules; and use of low-power printed circuit board electronics to interrogate the mass fabricated interaction sites and electrical sensing of the protein-nucleic acid and cell-nucleic acid hybridization.

In one embodiment, the invention is directed to devices, comprising: a thermally responsive, electrically insulating substrate; at least one heating element; and a first detecting unit, comprising: a first electrode and a second electrode separated by a nanogap; and a plurality of first aptamer probes attached to said substrate in said nanogap.

In other embodiments, the invention is directed to devices, wherein said first aptamer probes are double-stranded nucleic acids and have the same nucleic acid sequence.

In yet other embodiments, the invention is directed to devices, wherein said first aptamer probes comprise: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; and wherein each of said first aptamer probes has the same nucleic acid sequence.

In yet another embodiment, the invention is directed to systems, comprising: a device described herein; and an electrical reading device for interrogating said device; wherein said electrical reading device is optionally portable.

In one embodiment, the invention is directed to methods for detecting hybridization of a target, comprising: providing a device, comprising: a thermally responsive, electrically insulating substrate; at least one heating element; and a first detecting unit, comprising: a first electrode and a second electrode separated by a nanogap; and a plurality of first aptamer probes attached to said substrate in said nanogap; providing a solution comprising said target under hybridizing conditions; wherein said target is a protein or a cell; and wherein said target hybridizes at least some of said first aptamer probes; applying a voltage drop across said electrodes; and measuring a change in conductivity, resistivity, capacitance, or impedance across said electrodes at known locations to determine perfect complementarity of said target to said first aptamer probes.

In another aspect, methods of detecting tumor cells are described herein. In some embodiments, a method of detecting tumor cells comprises contacting a plurality of cells with a substrate of a device described herein. Any device described herein may be used. In some cases, the device comprises a substrate surface and a plurality of first aptamer probes attached to the substrate surface. Moreover, a method of detecting tumor cells described herein can further comprise contacting a plurality of cells with the plurality of first aptamer probes attached to the substrate surface; adhering one or more of the plurality of cells to the substrate surface; and measuring a non-uniformity parameter, a Hausdorff distance, a change in the number of pseudopods, and/or a shape of at least one adhered cell. Moreover, in some instances, such a method further comprises using the non-uniformity parameter, Hausdorff distance, change in the number of pseudopods, and/or shape of the adhered cell to identify the adhered cell as a tumor cell or a non-tumor cell. Additionally, in some embodiments, the plurality of first aptamer probes forms a uniform or substantially uniform coating on the substrate surface. Further, the plurality of first aptamer probes can comprise one or more anti-EGFR aptamers.

In some embodiments of methods described herein, the plurality of cells comprises tumor cells, including circulating tumor cells (CTCs). Moreover, in some cases, the plurality of cells comprises a mixture of tumor cells and non-tumor cells. In addition, in some instances, contacting a plurality of cells with the plurality of first aptamer probes comprises contacting a bodily fluid such as urine, blood, or saliva with the plurality of first aptamer probes. Contacting a plurality of cells with the plurality of first aptamer probes can also comprise contacting an operative specimen, pleural fluid, ascites, spinal fluid, benign tissue, or suspected malignant tissue with the plurality of first aptamer probes.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 4A is a schematic view of metal nanoplates as heating elements 2a, 2b embedded on a silicon dioxide chip 1 with a set of electrodes 5a, 5b with a nanogap 6.

FIG. 4B is an expanded side view of metal nanoplates as heating elements 2a, 2b embedded on a silicon dioxide chip 1 with a set of electrodes 5a, 5b with a nanogap 6 shown in FIG. 4A, but also showing the attached hairpin loop aptamer probes 8.

DETAILED DESCRIPTION

Figure 1A:
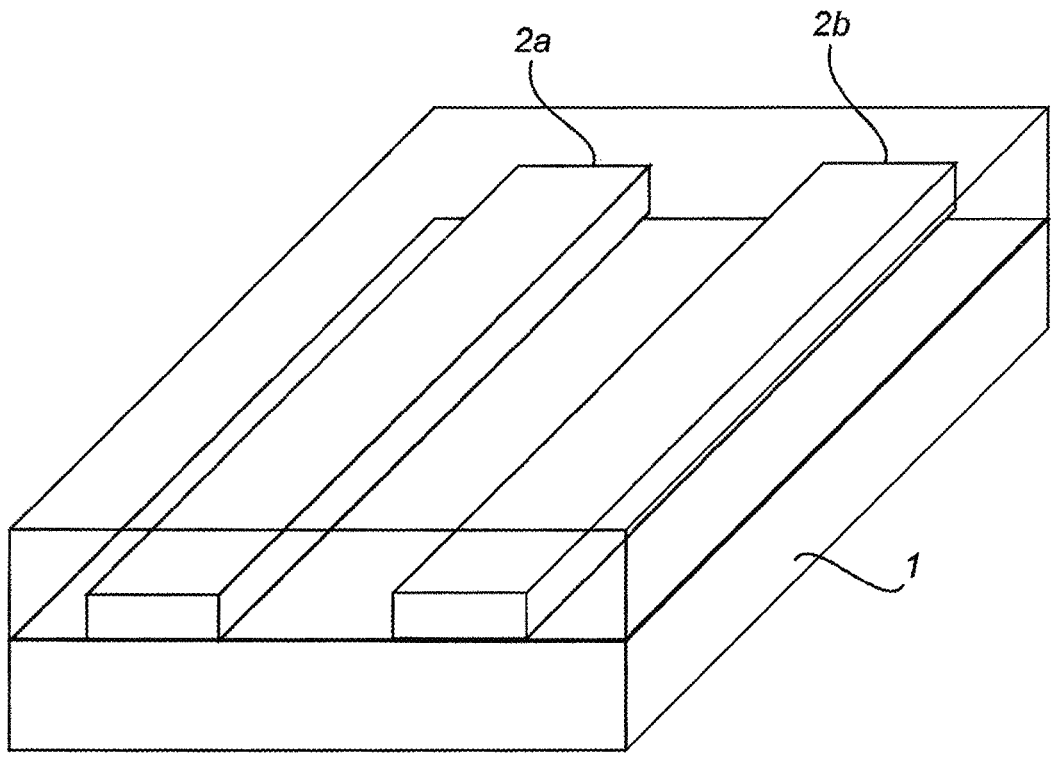
FIG. 1A is a three-dimensional view of metal nanoplates as heating elements 2a, 2b embedded on a silicon dioxide chip 1.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

Unless defined otherwise, all technical and scientific terms used herein have the same meaning as commonly understood to one of ordinary skill in the art to which this invention belongs. The following definitions are provided for the full understanding of terms used in this specification.

As used herein, the article "a," "an," and "the" means "at least one," unless the context in which the article is used clearly indicates otherwise.

As used herein, the term "nucleic acid" as used herein means a polymer composed of nucleotides, e.g. deoxyribonucleotides or ribonucleotides.

As used herein, the terms "ribonucleic acid" and "RNA" as used herein mean a polymer composed of ribonucleotides.

As used herein, the terms "deoxyribonucleic acid" and "DNA" as used herein mean a polymer composed of deoxyribonucleotides.

As used herein, the term "oligonucleotide" denotes single- or double-stranded nucleotide multimers of from about 2 to up to about 100 nucleotides in length.

Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™. technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

As used herein, the term "cDNA" means a complementary DNA molecule made as a copy of mRNA amplified using PCR for deposition on arrays. cDNAs can range from about 100 bp to about 8,000 bp, where average cDNAs are typically 1 to 2 kb in length.

As used herein, the term "array" means a substrate having a plurality of binding agents (probes) stably attached to its surface, where the binding agents (probes) are arranged in a spatially defined and physically addressable manner across the surface of the substrate in any of a number of different patterns. Generally, at least two of the plurality of binding agents (probes) is different.

As used herein, the term "complementary" refers to the topological compatibility or matching together of interacting surfaces of a probe molecule and its target. Thus, the target and its probe can be described as complementary, and furthermore, the contact surface characteristics are complementary to each other.

As used herein, the term "bind" in the context of an aptamer refers to a process of establishing a non-covalent, sequence-specific interaction between nucleic acid strands in the aptamer molecule and either protein or whole cell of the target to form conjugate.

As used herein, the term "probe" refers to a surface-immobilized molecule that can be recognized by a particular target.

As used herein, the term "target" refers to a molecule that has an affinity for a given probe. Targets may be naturally-occurring or man-made molecules. Also, they can be employed in their unaltered state or as aggregates with other species.

As used herein, the term "biological chip," "chip", or "bio sensor" refers to a substrate having a surface to which one or more arrays of probes is attached.

As used herein, the term "wafer" refers to a substrate having a surface to which a plurality of probe arrays is attached. On a wafer, the arrays are physically separated by a distance of at least about a millimeter, so that individual chips can be made by dicing a wafer or otherwise physically separating the array into units having a probe array.

As used herein, the term "aptamer" refers to nucleic acid molecules having specific binding affinity to molecules through interactions other than classic Watson-Crick base pairing. Aptamers, like peptides generated by phage display or monoclonal antibodies, are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarity, hydrophobic contacts, steric exclusion) that drive affinity and specificity in antibody-antigen complexes.

As used herein, the term "hairpin structure" refers to an oligonucleotide that contains a double-stranded stem segment and a single-stranded loop segment wherein the two polynucleotide or nucleic acid strands that form the double-stranded stem segment is linked and separated by the single polynucleotide or nucleic acid strand that forms the loop segment. The "hairpin structure" can also further comprise 3' and/or 5' single-stranded region(s) extending from the double-stranded stem segment.

As used herein, the phrase "two perfectly complementary nucleotide sequences" refers to a nucleic acid duplex wherein the two nucleotide strands match according to the Watson-Crick base pair principle, i.e., A-T and C-G pairs in DNA:DNA duplex and A-U and C-G pairs in DNA:RNA or RNA:RNA duplex, and there is no deletion or addition in each of the two strands.

As used herein, the term "nano-textured" to surfaces having at least one dimension on the nanoscale, i.e., only the thickness of the surface of an object is between 0.1 and 100 nm.

Accordingly, in one embodiment, the invention is directed to devices, comprising: a thermally responsive, electrically insulating substrate; at least one heating element; and a first detecting unit, comprising: a first electrode and a second electrode separated by a nanogap; and a plurality of first aptamer probes attached to said substrate in said nanogap. In certain embodiments, the first aptamer probes are double-stranded nucleic acids and have the same nucleic acid sequence. In certain other embodiments, the first aptamer probes comprise: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; and wherein each of said first aptamer probes has the same nucleic acid sequence.

In yet another embodiment, the invention is directed to systems, comprising: a device described herein; and an electrical reading device for interrogating said device; wherein said electrical reading device is optionally portable.

In one embodiment, the invention is directed to methods for detecting hybridization of a target, comprising: providing a device, comprising: a thermally responsive, electrically insulating substrate; at least one heating element; and a first detecting unit, comprising: a first electrode and a second electrode separated by a nanogap; and a plurality of first aptamer probes attached to said substrate in said nanogap; providing a solution comprising said target under hybridizing conditions; wherein said target is a protein (such as biomarkers, environmental samples, bioterrorism agent like virus and bacteria, and contaminants) or a cell (such as a tumor cell, especially a circulating tumor cell (CTC)); and wherein said target hybridizes at least some of said first aptamer probes; applying a voltage drop across said electrodes; and measuring a change in conductivity, resistivity, capacitance, or impedance across said electrodes at known locations to determine perfect complementarity of said target to said first aptamer probes.

In another aspect, methods of detecting tumor cells are described herein. In some embodiments, a method of detecting tumor cells comprises contacting a plurality of cells with a substrate of a device described herein. In some cases, the device comprises a substrate surface and a plurality of first aptamer probes attached to the substrate surface. Moreover, a method of detecting tumor cells described herein can further comprise contacting a plurality of cells with the plurality of first aptamer probes attached to the substrate surface; adhering one or more of the plurality of cells to the substrate surface; and measuring a non-uniformity parameter, a Hausdorff distance, a change in the number of pseudopods, and/or a shape of at least one adhered cell. Moreover, in some instances, such a method further comprises using the non-uniformity parameter, Hausdorff distance, change in the number of pseudopods, and/or shape of the adhered cell to identify the adhered cell as a tumor cell or a non-tumor cell.

Devices

In one embodiment, the invention is directed to devices, comprising: a thermally responsive, electrically insulating substrate; at least one heating element; and a first detecting unit, comprising: a first electrode and a second electrode separated by a nanogap; and a plurality of first aptamer probes attached to said substrate in said nanogap. In certain embodiments, the first aptamer probes are double-stranded nucleic acids and have the same nucleic acid sequence. In certain other embodiments, the first aptamer probes comprise: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; and wherein each of said first aptamer probes has the same nucleic acid sequence.

In certain embodiments, including those involving arrays, the device further comprises: a plurality of second detecting units, comprising: a first electrode and a second electrode separated by a nanogap; and a plurality of second aptamer probes attached to said substrate in said nanogap. In certain embodiments where the target is a protein, the second aptamer probes are double-stranded nucleic acids and have the same nucleic acid sequence; wherein said second aptamer probes are the same or different from said first aptamer probes in said first detecting unit; and wherein said second aptamer probes are the same or different from other second aptamer probes in said plurality of second detecting units. In certain embodiments where the target is a cell, each of said second aptamer probes comprises: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; wherein said second aptamer probes are the same or different from said first aptamer probes in said first detecting unit; and wherein said second aptamer probes are the same or different from other second aptamer probes in said plurality of second detecting units.

In certain embodiments, the device further comprises: a plurality of microfluidic channels; and an optional cover.

In certain embodiments of the device, the first detecting unit is located on the surface of said substrate.

In certain embodiments of the device, said at least one heating element is located in a first layer; and said first electrode and said second electrodes are located in a second layer.

The device may be fabricated as a single layer or, preferably, as multiple layer, using standard and advanced silicon fabrication techniques. In preferred embodiments, there are two functional layers. The first layer has heating elements, preferably embedded heating nano-plates. The second layer has electrical nano-electrodes.

Standard complementary metal-oxide-semiconductor (CMOS) processes may be used to create an array of detecting units on a single wafer for multiple nucleic acid detection with printed circuit board (PCB) data acquisition and analysis capability.

The design of the chip gives an array of detecting units in which hundreds ($n^2$) of interaction sites may be addressed using a few (2n) probing pads. The probing pads in turn are addressed and controlled using sensitive electronics and software in the manner that pixels in a thin film transistor (TFT) television. This provides an integrated system with on-chip circuitry for data gathering, storage, and analysis. Suitable techniques for addressing the interaction sites at the electrodes in the array are described in the following references, which are incorporated herein by reference in their entirety: A. Hassibi and T. H. Lee, *IEEE Sensors Journal*, 6(6), 1380-1388, (2006); W. F. Aerts, S. Verlaak, and P. Heremans, IEEE Transactions on Electron Devices, 49(12), 2124-2130, (2002); and A. Hassibi, "Integrated Microarrays" Section in *Electrical Engineering*. 2005, Stanford University: Palo Alto, Calif. p. 141.

Substrate

The devices of the invention include a thermally responsive, electrically insulating substrate. The substrate is preferably flat but may take on a variety of alternative surface configurations. For example, the substrate may contain raised or depressed regions on which the probes are located. The substrate and its surface preferably form a rigid support on which the probes can be attached. For instance, the substrate may be any thermally responsive, electrically insulating materials. Suitable substrates include, but are not limited to, functionalized glass, Si, Ge, GaAs, GaP, $SiO_2$, $SiN_4$, modified silicon, polydimethylsiloxane (PDMS), or any one of a wide variety of gels or polymers such as (poly)tetrafluoroethylene, (poly)vinylidenedifluoride, polystyrene, polycarbonate, polypropylene, or combinations thereof. The substrate may be deposited by chemical vapor deposition. Other substrate materials and deposition methods will be readily apparent to those of skill in the art upon review of this disclosure. In a preferred embodiment, the substrate is flat glass or silica with a silicon dioxide layer grown on the surface to provide electrical insulation.

In certain embodiments, the substrate is nano-textured. Three-dimensionally nano-texturing of the substrate provides a higher probability of capturing and isolating proteins and/or cells, such as tumor cells, from solution, thereby aiding in the development of cytological tools for circulating tumor cells (CTC) detection, for example. In certain preferred embodiments, the substrate is nano-textured PDMS.

The aptamer probes useful in the devices, systems, and methods of the invention are attached to the surface of the chip. In one embodiment, the chip is first cleaned, for example, using oxygen plasma at 200 W in $Ar+O_2$. This treatment also makes the surface hydrophilic. Surface functionalization of the chips may be done in a nitrogen glove box with controlled temperature, as described in S. M. Iqbal, D. Akin, and R. Bashir, *Nature Nanotechnology*, 2(4), 243-248 (2007), incorporated herein by reference. For example, on a clean chip, a self-assembled monolayer (SAM) of 3-aminopropyltrimethoxysilane (APTMS) (5% solution in 95% ethanol) is reacted with the hydroxyls on the surface to provide silane functionality to the surface of the chip. Next, the silane-functionalized surface is reacted with p-phenylene diisothiocyanate (PDITC)(dissolved in dimethylformamide containing 10% pyridine) as a bifunctional linker. Finally, the chip is immersed in a solution containing the hairpin loop oligonucleotide probes. Once attached, the probe molecule may be heat-cycled in buffer, such as TrisEDTA (TE) buffer, multiple times to ensure that all molecules form the requisite hairpin loop structures. To deactivate the unreacted surface-bound isothiocyanate groups, the chips may be immersed in a blocking solution, such as 50 mM 6-amino-1-hexanol and 150 nM DPEA in dimethylformamide (DMF) for 2 hours after which the substrate is sequentially washed with, for example, DMF, acetone, deionized water, and dried in a stream of nitrogen.

Heating Elements

In certain embodiments, the heating element is embedded in said substrate. FIGS. 4A and 4B show one embodiment where the heating elements are embedded in the substrate.

The heating elements useful in the devices, systems, and methods of the invention may comprise any material suitable for preparing electrodes, including but not limited to, gold, silver, titanium, copper, and combinations thereof.

Figure 1B:
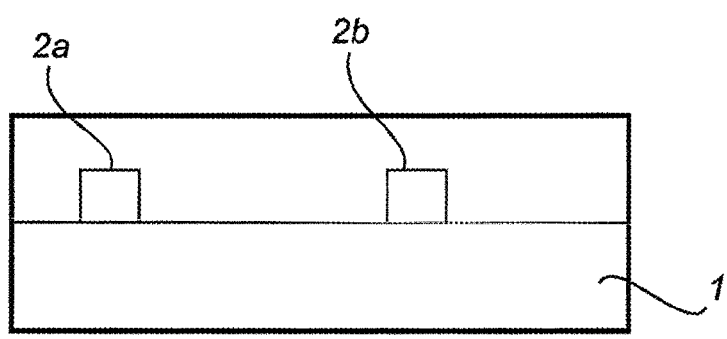
FIG. 1B is a side view of the metal nanoplates as heating elements 2a, 2b embedded on the silicon dioxide chip 1, shown in FIG. 1A.
Figure 2:
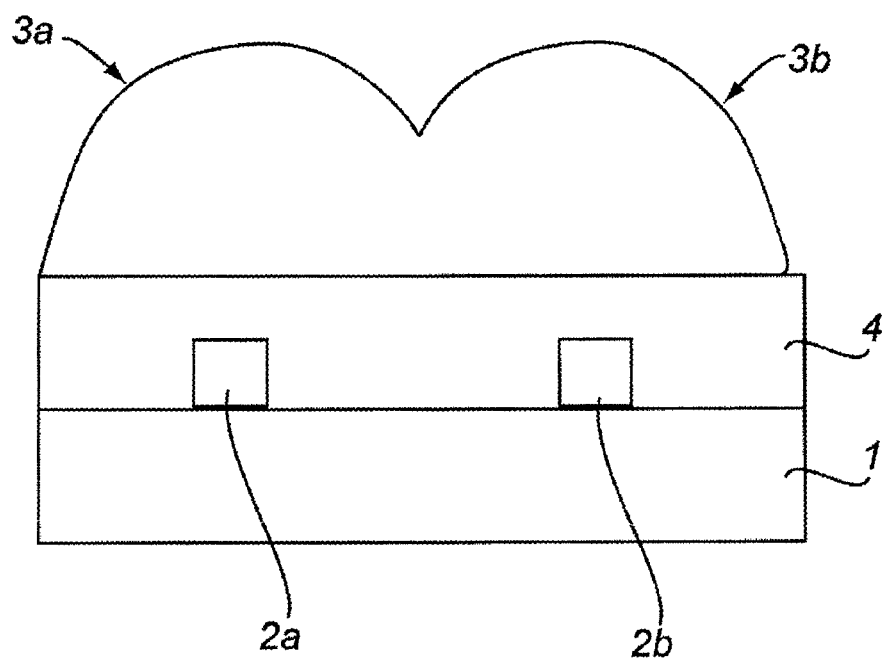
FIG. 2 is a side view of metal nanoplates as heating elements 2a, 2b embedded on silicon dioxide chip 1 showing typical temperature gradients 3a, 3b for each heating element 2a, 2b.

In certain embodiments, the devices of the invention have an array of heating elements. The heating elements are metal nanoplate heater elements 2a, 2b embedded on silicon dioxide chip 1, as shown in FIG. 1A and FIG. 1B. The heating elements may be fabricated using standard lithography and can provide precise control of temperature fields, as described in A. Jain, K. D. Ness, H. A. Fishman, and K. E. Goodson, *Microtechnology in Medicine and Biology*, 2005, 3$^{rd}$ IEEE/EMBS Special Topic Conference on 2005: 398-399, incorporated herein by reference. FIG. 2 shows typical temperature gradients from individual nanoplates 2a, 2b. The individual heating elements may be addressed in groups to enable temperature cycling for various operations of the device, including, but not limited to, focusing of oligonucleotide targets toward the nanogap between the sets of electrodes 5a, 5b, melting of double stranded oligonucleotide targets (without melting and denaturing the hairpin loop oligonucleotide probes causing loss of sensitivity against mismatches), and recycling of the oligonucleotide probes.

Figure 3A:
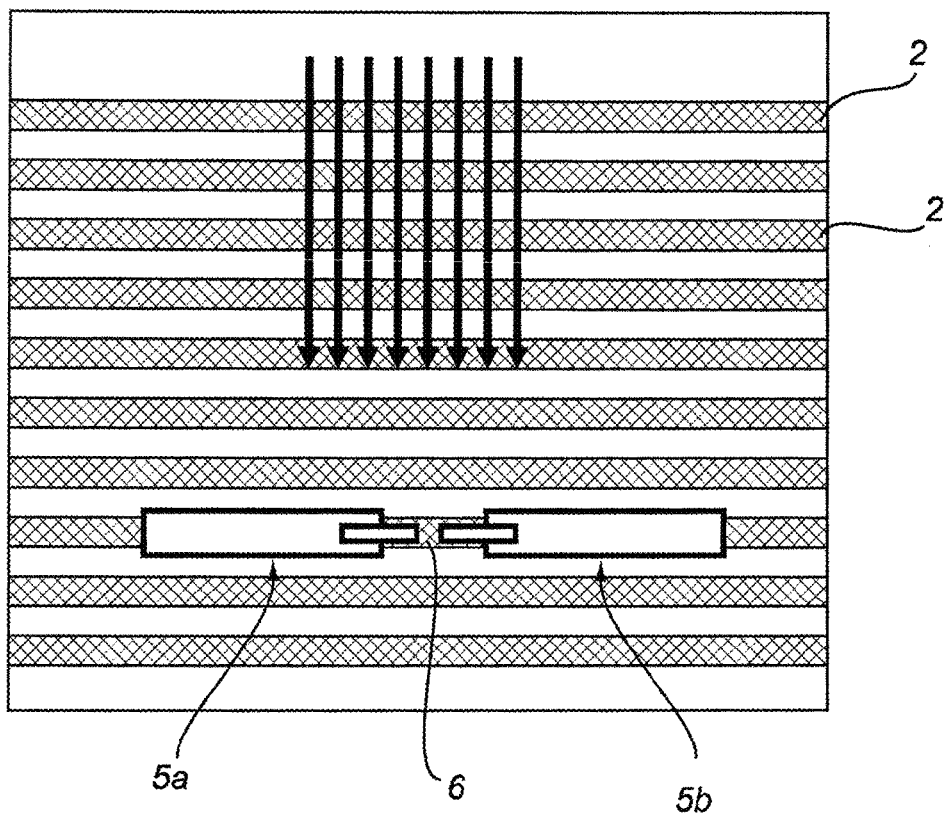
FIG. 3A is a top view of metal nanoplates as heating elements 2a, 2b embedded on a silicon dioxide chip 1 with nanogap electrodes 5a, 5b using a temperature gradient to focus or move target molecules 10 toward the nanogap electrodes 5a, 5b.
Figure 3B:
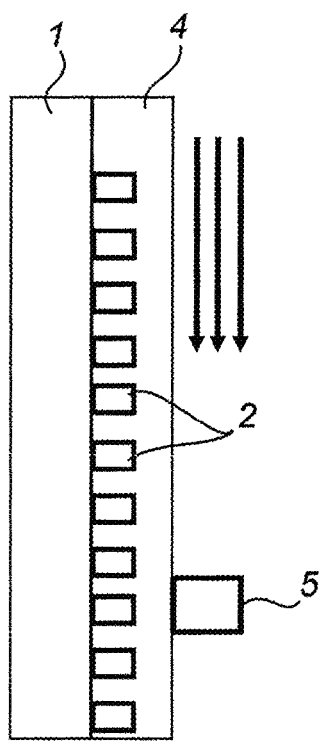
FIG. 3B is a side view of metal nanoplates as heating elements 2a, 2b embedded on a silicon dioxide chip 1 with nanogap electrodes 5a, 5b showing the movement of the buffer solution containing the oligonucleotide target molecules 10 toward the nanogap electrodes 5a, 5b.

In operation as shown in FIGS. 3A and 3B, a solution containing at least one buffer and the double-stranded oligonucleotide (DNA, cDNA, or RNA fragment) is flowed into the denaturation chambers (not shown) from the microfluidic channel (not shown) at a temperature gradient at least as high as the melting temperature ($T_m$) of the double-stranded oligonucleotide target before being carried over the nanogap of the electrodes. The black arrows indicate the flow of the solution.

The embedded heating elements serve multiple purposes, including: on-chip/device denaturing of the double-stranded oligonucleotide target molecules, removal of secondary structures of cDNA, competitive capture with the surface-bound oligonucleotide probe; recycling capability of the device for the next batch of target solution by denaturing the probe-target duplex; and temperature gradient focusing to concentrate the solution containing the oligonucleotide target at the nanogap of the electrodes.

The heating elements may be covered in a thermally-responsive but electrically-insulating material layer, such as silicon dioxide, deposited, for example, by chemical vapor deposition (CVD).

Electrodes and Nanogap

In certain embodiments, the first and second electrodes comprise a metal selected from the group consisting of gold, silver, titanium, copper, or a combination thereof.

Figure 5A:
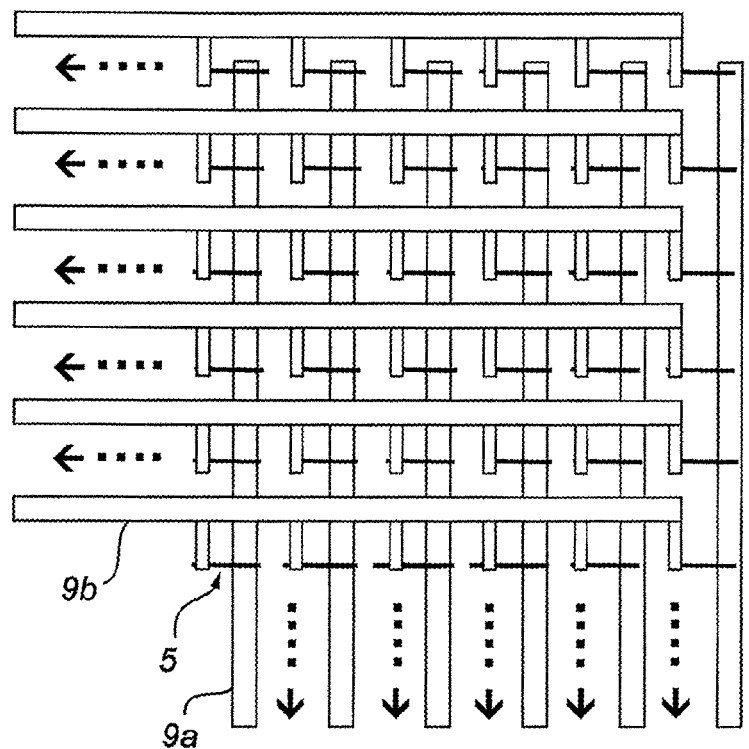
FIG. 5A is a top view of one embodiment showing two bus lines 9a, 9b used to address the individual set of electrodes 5a, 5b with a nanogap 6 fabricated with nanoimprint lithography. Arrows indicate the extension of similar structures to cover the whole chip area.

Nanoimprint lithography may be used to fabricate the electrodes with the nanogaps. The electrodes may formed into an array where each nanogap is individually addressed with metal lines (bus-bars), preferably running at right angles. Each mutually-insulated intersection of the addressing lines contacts one nanogap electrode pair that serves as the binding and sensing site of the probe-target hybridization. The bus lines may be fabricated in two layers with electrical isolation between the two layers achieved by chemical vapor deposition (CVD) of silicon nitride. FIG. 5A is a top view of one embodiment showing two bus lines 9a, 9b used to address the individual set of electrodes 5a, 5b with a nanogap 6 fabricated with nanoimprint lithography. Arrows indicate the extension of similar structures to cover the whole chip area. In certain embodiments, microfluidic channels run exactly on top of the nanogap electrodes, thus reducing any cross-talk between probe and target molecules of successive rows.

Figure 5B:
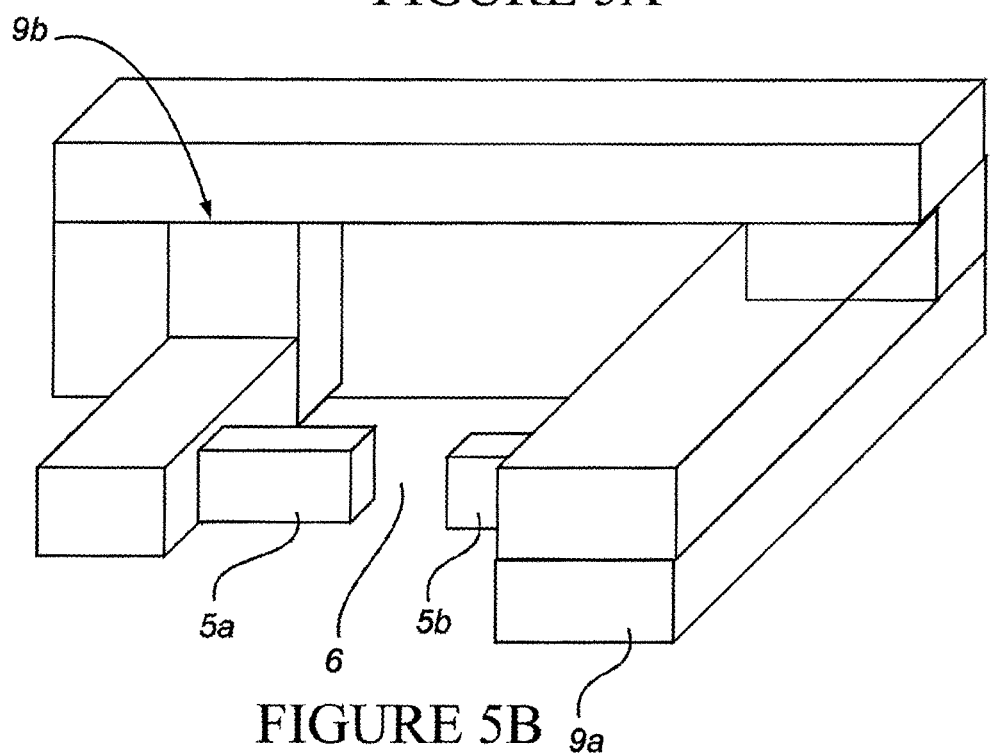
FIG. 5B is a blown up schematic (not to scale) of FIG. 5A showing the individual set of electrodes 5a, 5b with a nanogap 6, one electrode addressing/measuring bus 9a covered with silicon nitride and the other electrode addressing/measuring bus 9b. Oligonucleotide probe molecules (not shown) are attached to the chip in the nanogap 6 between the electrodes 5a, 5b.

FIG. 5B is a blown up schematic (not to scale) of FIG. 5A showing the individual set of electrodes 5a, 5b with a nanogap 6, one electrode addressing/measuring bus 9a covered with silicon nitride and the other electrode addressing/ measuring bus 9b. Oligonucleotide probe molecules (not shown) are attached to the chip in the nanogap 6 between the electrodes 5a, 5b. This three-dimensional structure is adjacent to and aligned with embedded nanoplate heating elements discussed previously. The structure is covered with microfluidic channels. The electrical isolation may be achieved by sequential and automated measurement of each pair of electrodes. In preferred embodiments, the use of chemical vapor deposition (CVD) silicon dioxide results in a rough surface which facilitates the covalent attachment of the oligonucleotide probes to the surface of the substrate, thereby permits an increased density of probes in the nanogap.

In certain embodiments, nanopatterns may be made on an oxidized silicon wafer using e-beam lithography (EBL). The EBL patterns may be used to fabricate the stamp for the nanoelectrode fabrication. The EBL patterns may be used to remove silicon dioxide and then silicon from the non-patterned areas using deep reactive ion etching (DRIE). Silicon dioxide acts as a hard mask during the process, resulting is a high aspect ratio nano-scale linear island features in silicon having the same dimensions as required the nanogap electrodes. The wafer may act as a stamping mask for NIL. In NIL, a polymer layer is spun on the wafer and a stamping wafer is compressed on the polymer to transfer the pattern. One stamp can be used multiple times and one stamping takes a few minutes to transfer the nano-scale patterns in the polymer. Standard lift-off process may be carried out to create the metal lines at the nanoscale from these stamp-defined patterns. In certain embodiments of the lift-off process, metal stays only in the NIL transferred nanoelectrode structure and the remainder of the metal lifts off in an ultra-sonicator assisted solvent soak. The first layer of addressing electrodes/bus may then be using standard optical lithography aligned to the nano-scale metal lines. The second layer of metal lines/bus may be deposited after CVD deposition of silicon nitride and reactive ion etch opening of small micron sized windows in the silicon nitride above the nanogap electrodes.

The use of three-dimensional interaction volume and interfacing space addresses the challenges of selectivity, high-yield fabrication, and sensitivity. Such three-dimensionality provides a means of not only improving selectivity by filtering unwanted species, but also allows reduced signal-to-noise ratios relative to what is attainable on planar substrates. The nanoelectrodes employed in the devices of the invention enable the majority of the electric field to interact with the biomolecules, resulting in highly sensitive detection.

Figure 7:
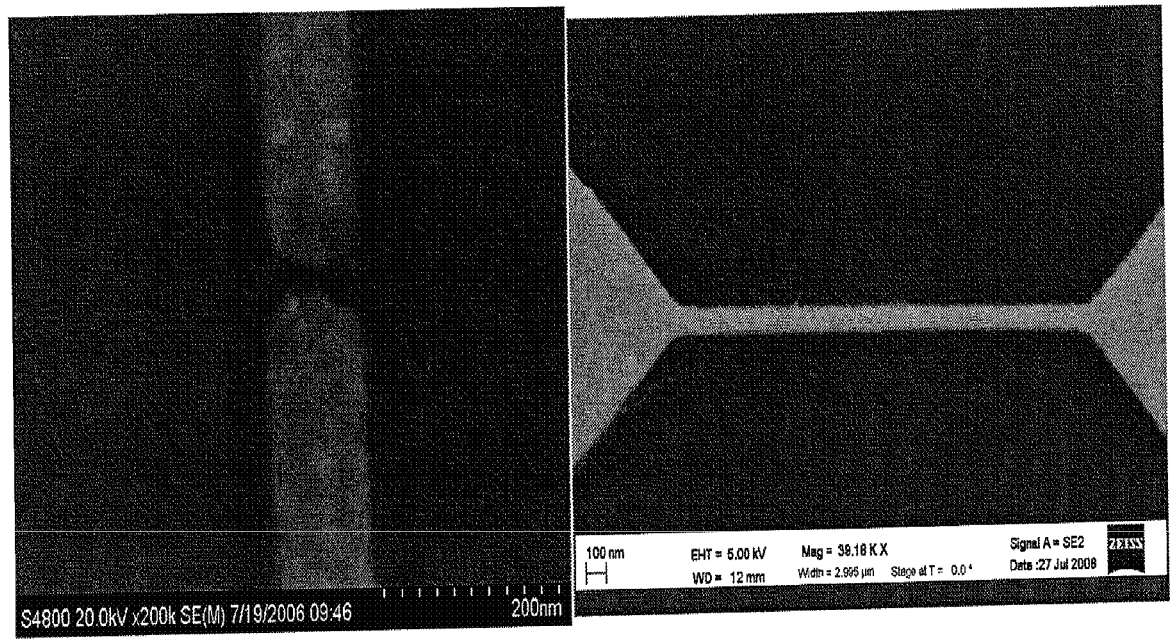
FIG. 7 shows the gold electrodes with a nanogap prior to attachment of the hairpin loop probes of one embodiment of the invention.

Different methods may be used to fabricate the nanogap between a set of electrodes. A break junction may be prepared from an already fabricated electrode by, for example, a mechanically controlled break junction process or an electromigration break junction process. In certain preferred embodiments, wherein said nanogap is formed by focused ion beam scratching followed by electromigration. FIG. 7 shows an scanning electron micrograph of a set of electrodes of gold with a nanogap.

In certain embodiments, the nanogap is about 10 nm to about 500 nm.

A break junction is the discontinuity or a nanoscale gap in a seemingly continuous structure. The most common visualization of a break junction is a gap formed in a thin metal strip by various methods. The nanoscale gap in the metal strip is the area of interest where the molecule is placed to make electrical contacts.

A mechanically-controlled break junction process is a process where a narrow bridge of metal is suspended above a flexible substrate. By bending the substrate, the metal bridge can be broken, and the distance between the ends can be controllably adjusted, with increments of much less than a pico meter.

To create a break junction using electromigration, an external electric field applied to a circuit causes large current density in the wires that connect the components. The electrons in a metal move under the influence of the large current density and if there is a charged defect in the metal, the momentum transfers from the conduction electrons to such a defect. As the momentum exchange becomes larger, a force is built up causing the mass movement of the atoms away from the defect causing breakdown of the metal at that point. In break junction, the break usually occurs in the constricted part of the metal in a controllable and self-limiting fashion. Normally, the breaking process consistently produces two metallic electrodes at typical separations.

There are several techniques to fabricate break junctions, well known in the art. Almost all of them follow the conventional process of thin film deposition, lithography and etching on oxidized silicon wafers. Suitable techniques include those disclosed in the following references, which are incorporated herein by reference in their entirety: Park, H., et al., *Applied Physics Letters,* 75: 301-303 (1999); Zhou, C., et al., *Applied Physics Letters,* 67: 1160-1162 (1995); Bezryadin, A. and C. Dekker, *Journal of Vacuum Science & Technology B: Microelectronics and Nanometer Structures,* 15: 793-799 (1997); and Bezryadin, A., C. Dekker, and G. Schmid, *Applied Physics Letters,* 71: 1273-1275 (1997).

Fabrication of controlled nano-gap electrodes is another efficient method of trapping the oligonucleotide probes. This method also follows the same procedure of integrating single or double strand DNA into a circuit using metal electrodes to perform conductivity measurements. The separation between the electrodes must be small in accordance with the length nucleic acid molecules used.

In certain embodiments, a 7-bit addressing scheme with multiplexer circuits may be used in conjunction with an analog signal for the biasing of the sensing/measurement block at the nanogap. An external clock may be used on the mounting printed circuit board to provide the measurement frequency. The clock enables the input biasing across the sensing/measurement block. The current or conductance in response to the bias is measured at the shared output electrode and may be normalized and co-related with the preceding and following data gathered from the same sensing/measurement block.

In certain embodiments, the invention is directed to methods of forming a metallic nano-scale break junction on a chip, comprising: forming on said chip a metal line, preferably having a thickness of less than about 5 μm and a width less than about 5 μm; bombarding said metal line with a focused-ion beam to form a thinned section in said metal line; and applying current to said metal line sufficient to cause electromigration in said thinned section of said metal line. In preferred embodiments, the metal line is formed using photolithography.

Probes

The probes useful in the invention are aptamers. Aptamers of the present invention can be obtained by SELEX (Systematic Evolution of Ligands by EXponential enrichment) method, commonly used for obtaining aptamers. First, a certain template DNA is synthesized that contains an appropriate length of random sequence flanked by two arbitrary primer sequences. This template DNA is amplified by PCR (Polymerase Chain Reaction) to obtain a randomized DNA aptamer pool. Next, the randomized DNA aptamer pool is associated with a target substance, and then DNAs not bound to the target substance are removed, and DNA aptamers bound to the target substance are extracted. The resultant DNA aptamers are amplified by PCR using the primer sequences, wherein the PCR is performed under the presence of 5 to 8 mM of Mg2+ for lowering replication accuracy and causing a mutation to be introduced more easily to obtain a further DNA aptamer pool that contains new DNA aptamers that would not be present in the DNA aptamer pool before performing the association with the target substance. The new DNA aptamers may have a stronger binding strength, that is, evolved DNA aptamers may be generated. A series of procedures explained above is repeated for 5 to 15 rounds with a pool of the evolved DNA aptamers to obtain DNA aptamers being able to specifically bind to the target substance. The resultant DNA aptamer pool after the final round is cloned and sequenced as usually performed by those skilled in the art. The procedures such as synthesis of template DNA and PCR in the SELEX process and cloning and sequencing are performed by methods commonly used by those skilled in the art. The aptamers of the present invention can be chemically synthesized by methods commonly used by those skilled in the art based on the determined sequence. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In certain embodiments where the target is a protein, the first aptamer probes are double-stranded nucleic acids and have the same nucleic acid sequence.

In certain embodiments where the target is a whole cell, each of said first aptamer probes comprises: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; and wherein each of said first aptamer probes has the same nucleic acid sequence. In certain embodiments, each of said first aptamer probes comprises: a spacer having about one nucleotide base to about 20 nucleotide bases; a nucleotide loop having about 3 nucleotide bases to about 100 nucleotide bases; and a base pair stem having about 3 nucleotide base pairs to about 20 nucleotide base pairs. In certain embodiments, each of said first aptamer probes comprises: a spacer having about 3 nucleotide bases; a nucleotide loop having about 12 nucleotide bases; and a base pair stem having about 6 nucleotide base pairs.

In certain embodiments, the aptamer probes are covalently attached to said substrate.

In one embodiment, the aptamer probes are amine-modified to permit covalent attachment to the substrate. In certain embodiments, there is direct attachment of the oligonucleotide probe through a silane, such as, for example, (3-glycidyloxypropyl)trimethoxysilane). In other embodiments, there is attachment through a homo-bifunctional layer, such as, for example, 1,4-phenylene diisothiocyanate, on top of a silane, such as, for example, 3-aminopropyltrimethoxysilane.

The selection of probes and their organization in an array depends upon the use to which the biological chip will be put. In one embodiment, the chips are used to sequence or re-sequence nucleic acid molecules, or compare their sequence to a reference molecule. Re-sequencing nucleic acid molecules involves determining whether a particular molecule has any deviations from the sequence of reference molecule.

In typical diagnostic applications, a solution containing one or more targets to be identified (i.e., samples from patients) contacts the probe array. The targets will bind or hybridize with complementary probe sequences. Accordingly, the probes will be selected to have sequences directed to (i.e., having at least some complementarity with) the target sequences to be detected, e.g., human or pathogen sequences. Accordingly, locations at which targets hybridize with complimentary probes can be identified by locating the electrical current in an electrode set. Based on the locations of the electrodes where hybridization occurs, information regarding the target sequences can be extracted. The existence of a mutation may be determined by comparing the target sequence with the wild type.

Individual probe sequence may be designed to detect known single mutations. However, the invention is not limited to methods of detecting known single mutations, but may be used to identify the sequence of any desired target.

The aptamer probes may be immobilized on the substrate between the electrodes using the surface chemistry described by the techniques described in M. Manning, S. Harvey, P. Galvin, and G. Redmond, *Materials Science and Engineering*, C 23, 347 (2003), incorporated herein by reference.

In certain embodiments, the aptamer probes form a self-assembled monolayer between the electrodes.

The aptamer probes may be directed to and located in the gaps between a particular set(s) of electrodes by electrostatic trapping, i.e., energizing a particular set(s) of electrodes, preferably using alternating current, to direct the probes (which are charged) to the gaps. Different oligonucleotide probes, referred herein as "second aptamer probes," may be localized at their respective electrodes by providing the second aptamer probes and sequentially energizing the desired set(s) of electrodes to direct and localize the second oligonucleotide probes in the appropriate nanogap(s). This procedure may be repeated until all of the different aptamer probes are directed to and located in the nanogap(s) between their desired set(s) of electrodes.

Micro Fluidic Channels

Figure 6:
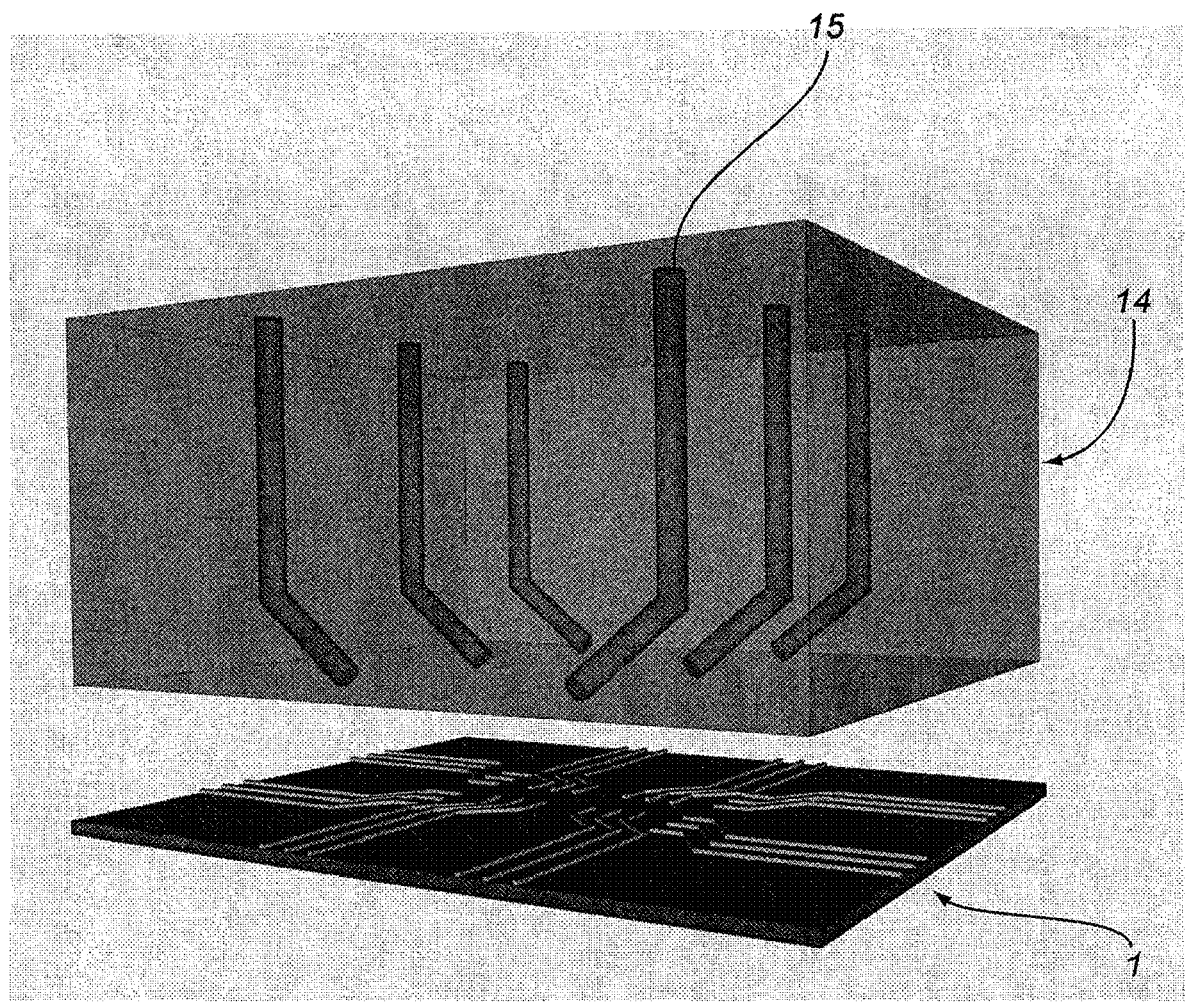
FIG. 6 is a schematic diagram showing one embodiment of the invention where a chip and a cover block with microchannels for fluid handling are shown.

Assays on biological arrays generally include contacting a probe array with a sample under the selected reaction conditions, optionally washing the well to remove unreacted molecules, and analyzing the biological array for evidence of reaction between target molecules and the probe molecules. These steps involve handling fluids. Microfluidic channels 15 may be used to deliver the liquids to the test sites, such as the one shown in FIG. 6 made from any suitable solid material, such as polydimethylsiloxane. The methods of this invention automate these steps so as to allow multiple assays to be performed concurrently. Accordingly, this invention employs automated fluid handling systems for concurrently performing the assay steps in each of the test wells. Fluid handling allows uniform treatment of samples in the test sites. Microtiter robotic and fluid-handling devices are available commercially, for example, from Tecan AG.

The device may be introduced into a holder in the fluid-handling device. This robotic device may be programmed to set appropriate reaction conditions, such as temperature, add samples to the device, incubate the test samples for an appropriate time, remove unreacted samples, wash the wells, add substrates as appropriate and perform detection assays. The particulars of the reaction conditions depend upon the purpose of the assay. For example, in a sequencing assay involving aptamer hybridization, standard hybridization conditions are chosen. However, the assay may involve testing whether a sample contains target molecules that react to a probe under a specified set of reaction conditions. In this case, the reaction conditions are chosen accordingly.

Systems

In other aspects, the invention is directed to systems, comprising: a device described herein; and an electrical reading device for interrogating said device described herein. In certain preferred embodiments, said electrical reading device is portable.

Preferably, the optional linker further comprises a hydrocarbon moiety attached to the cyclic disulfide. Suitable hydrocarbons are available commercially, and are attached to the cyclic disulfides. Preferably the hydrocarbon moiety is a steroid residue. Oligonucleotide-nanoparticle conjugates prepared using linkers comprising a steroid residue attached to a cyclic disulfide are stable to thiols (e.g., dithiothreitol used in polymerase chain reaction (PCR) solutions) as compared to conjugates prepared using alkanethiols or acyclic disulfides as the linker. This stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

Electrical Reader

Suitable electrical reading devices include any device for low power printed circuit board electronics capable of measuring either sequentially or in parallel a small change in conductivity, resistivity, capacitance, or impedance in a picoampere range. The Agilent 4155C semiconductor parameter analyzer and the Agilent 4156C semiconductor parameter analyzer are examples of suitable devices.

Methods

The invention provides a nanotechnology-based low-power, rapid, inexpensive, recyclable, and sensitive electrical detection device, system, and method of sub-femtomolar concentrations of proteins and cells, with no external sample preparation or labeling or other chemical modification of the sample. The biosensors of the invention may be used in wide variety of applications requiring sensitive target detection, including, but not limited to, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

In another aspect, the invention is directed to methods for detecting hybridization of a target, comprising: providing a device, comprising: a thermally responsive, electrically insulating substrate; at least one heating element; and a first detecting unit, comprising: a first electrode and a second electrode separated by a nanogap; and a plurality of first aptamer probes attached to said substrate in said nanogap; providing a solution comprising said target under hybridizing conditions; wherein said target is a protein or a cell; and wherein said target hybridizes at least some of said first aptamer probes; applying a voltage drop across said electrodes; and measuring a change in conductivity, resistivity, capacitance, or impedance across said electrodes at known locations to determine perfect complementarity of said target to said first aptamer probes.

In certain embodiments, the methods further comprise: washing to remove unhybridized components from said detecting unit.

In certain embodiments, the methods further comprise: heating said device to remove said hybridized targets and said hybridized nanoparticle reporter conjugates from said probe to permit recycling of said detecting unit.

In certain embodiments, the methods further comprise: heating a solution comprising double stranded oligonucleotide target to form said solution comprising single-stranded oligonucleotide target.

In certain embodiments, the methods further comprise: forming a temperature gradient to focus said single stranded oligonucleotide target at said detecting unit.

In certain embodiments, the methods further comprise: reversing the polarity of said voltage drop to remove unbound components or nonspecifically bound components from said detecting unit.

The methods of the invention may be used to quantify the level of oligonucleotides or polypeptides. For example, the change in conductance (or other electrical characteristic) between nanogaps is direct function of the number of specific binding events between nanogaps. The number of nanoparticles is a direct function of the number of specific binding events. Thus, the change of conductivity (or other electrical characteristic) can be directly correlated to the quantity of specific binding between the proteins or cells present in the sample and the aptamer probes.

In certain embodiments, the methods further comprise: providing, in addition to said first detecting unit, a plurality of additional detecting units, each additional detecting unit comprising: a first electrode and a second electrode separated by a nanogap; and a plurality of second oligonucleotide probes attached to said substrate in said nanogap; wherein said second oligonucleotide probes are in a hairpin loop formation and have the same nucleic acid sequence; and wherein said second oligonucleotide probes comprise an optional spacer, a loop, and a stem region, said stem region being double-stranded; wherein said second oligonucleotide probes are the same or different from said first oligonucleotides in said first detecting unit; and wherein said second oligonucleotide probes are the same or different from other second oligonucleotide probes in said plurality of second detecting units; providing a plurality of at least one second nanoparticle reporter conjugates under hybridizing conditions; wherein said second nanoparticle reporter conjugates comprise at least one nanoparticle and an oligonucleotide complementary to at least a portion of said stem of said second oligonucleotide probes; wherein said second nanoparticle reporter conjugates are the same or different from said first nanoparticle reporter conjugates; wherein said second nanoparticle reporter conjugates are the same or different from said other second nanoparticle reporter conjugates; wherein said measuring step is carried out in parallel or sequentially for said first detecting unit and said plurality of said additional detecting units.

In certain embodiments wherein said target is a protein target, the first aptamer probes are single-stranded or double-stranded nucleic acids and have the same nucleic acid sequence. The protein target may be optionally tagged with a nanoparticle selected from the group consisting of a metal, semiconductor, magnetic colloidal particle, or a combination thereof.

In certain embodiments wherein said target is a cell target; each of said first aptamer probes comprising: a first nucleic acid portion in a hairpin loop formation; wherein said first nucleic acid portion comprise a spacer, a loop, and a stem region, said stem region being double-stranded; and a second nucleic acid portion in a linear formation; wherein said second nucleic acid portion is single stranded and is attached to said substrate; and wherein said second nucleic acid portion is complementary to at least a portion of said spacer in said first nucleic acid portion; and wherein each of said first aptamer probes has the same nucleic acid sequence.

In certain embodiments, said voltage drop is applied as direct current. In other embodiments, said voltage drop is applied as alternating current and the alternating current impedance measured.

In certain embodiments, said measuring step measures an increase in conductivity across said electrodes at known locations to determine perfect specific binding of said protein or cell target to said first aptamer probes.

In certain embodiments, the method may optionally include the step of reversibly exchanging an imino proton in each base pair of the first aptamer probes with a metal ion selected from the group consisting of gold ion, silver ion, platinum ion, and copper ion. The reversible exchanging of an imino proton in each base pair may be carried out as described in A. Rakitin, Aich, P., Papadopoulos, C., Kobzar, Yu., Vedeneev, A. S., Lee, J. S., J. M. Xu, *Phys. Rev. Lett.*, 86(16), 3670-3673, (2001), which is incorporated herein by reference.

In certain embodiments, the method may optionally include the step of vectorially depositing silver on the double stranded nucleic acid sequence of the aptamer probes. In certain embodiments of this method, the vectorially depositing step comprises: ion exchanging silver ions on said double stranded aptamer sequence; reducing said silver ions; and developing silver aggregates on said double stranded nucleic acid sequence; as described in E. Braun, Y. Eichen, U. Sivan, and G. Ben-Yoseph, *Nature*, 391(6669), 775-778, (1998), incorporated herein by reference.

The methods of this invention will find particular use wherever high through-put of samples is required. The clinical setting requires performing the same test on many patient samples. The automated methods of this invention lend themselves to these uses when the test is one appropriately performed on a biological chip. For example, a DNA array can determine the particular strain of a pathogenic organism based on characteristic DNA sequences of the strain. The advanced techniques based on these assays now can be introduced into the clinic. Fluid samples from several patients are introduced into the test wells of a biological chip plate and the assays are performed concurrently.

In some embodiments, it may be desirable to perform multiple tests on multiple patient samples concurrently. According to such embodiments, rows (or columns) of the microtiter plate will contain probe arrays for diagnosis of a particular disease or trait. For example, one row might contain probe arrays designed for a particular cancer, while other rows contain probe arrays for another cancer. Patient samples are then introduced into respective columns (or rows) of the microtiter plate. For example, one column may be used to introduce samples from patient "one," another column for patient "two" etc. Accordingly, multiple diagnostic tests may be performed on multiple patients in parallel. In still further embodiments, multiple patient samples are introduced into a single well. In a particular well indicator the presence of a genetic disease or other characteristic, each patient sample is then individually processed to identify which patient exhibits that disease or trait. For relatively rarely occurring characteristics, further order-of-magnitude efficiency may be obtained according to this embodiment.

Particular assays that will find use in automation include those designed specifically to detect or identify particular variants of a pathogenic organism, such as HIV. Assays to detect or identify a human or animal gene are also contemplated. In one embodiment, the assay is the detection of a human gene variant that indicates existence of or predisposition to a genetic disease, either from acquired or inherited mutations in an individual DNA. These include genetic diseases such as cystic fibrosis, diabetes, and muscular dystrophy, as well as diseases such as cancer (the P53 gene is relevant to some cancers), as disclosed in U.S. Pat. No. 5,837,832.

Methods of detecting tumor cells and distinguishing tumor cells from non-tumor cells are also described herein. Thus, the present disclosure provides a mechanism for the early detection of cancer. Tumors start shedding cancer cells in the blood stream very early in the disease. These metastatic tumor cells may or may not form secondary tumors at onset of a primary tumor but their presence in blood is not well-established. These cells are called circulating tumor cells (CTC) or rare cells. Their concentration is too low at early stages and thus it is a challenge to detect them. The shedding of CTCs starts long before clinical symptoms of cancer become evident. Thus, there is a need for simple, cheap, rapid, and non-invasive tests for cancer that can be done as routine lab-work during annual or biannual physical check-ups. The present disclosure provides a method to check for and/or detect CTCs from blood as well as from simple body fluids like urine, saliva, and bladder wash. Moreover, the present disclosure provides a test that can be done in a simple clinical setup with minimal intervention or need of technicians for analysis or sample handling. Thus, in another aspect, improved methods of detecting cancer metathesis are described herein.

In some embodiments, a method of detecting tumor cells comprises providing a device described herein, wherein the device comprises a substrate surface and a plurality of first aptamer probes attached to the substrate surface. The method further comprises contacting a plurality of cells with the plurality of first aptamer probes attached to the substrate surface; adhering one or more of the plurality of cells to the substrate surface; and measuring a non-uniformity parameter, a Hausdorff distance, a change in the number of pseudopods, and/or a shape of at least one adhered cell. Additionally, in some cases, a method described herein further comprises using the non-uniformity parameter, Hausdorff distance, change in the number of pseudopods, and/or shape of the adhered cell to identify the adhered cell as a tumor cell or a non-tumor cell. Moreover, in some embodiments, the plurality of first aptamer probes can be at least partially replaced by a plurality of antibodies.

The substrate of a method described herein can comprises any substrate not inconsistent with the objectives of the present disclosure, including a substrate of a device described hereinabove. In some cases, the substrate surface is formed from glass, silicon, or a polymer. Other surfaces that can be functionalized with aptamers (or antibodies) may also be used. Further, in some instances, the plurality of first aptamer probes forms a uniform or substantially uniform coating on the substrate surface. A "uniform" coating can cover the entirety of the substrate surface. A "substantially uniform" coating can cover at least about 70%, at least about 80%, at least about 85%, at least about 90%, at least about 95%, or at least about 95% of the substrate surface. For example, in some embodiments, at least about 80% of the substrate surface is coated by the plurality of first aptamer probes.

Moreover, the aptamer probes can comprise any aptamer probes described hereinabove. In some cases, for instance, the plurality of first aptamer probes comprises an anti-EGFR aptamer.

In addition, the plurality of cells analyzed by a method described herein can comprise tumor cells, non-tumor cells, or a mixture of tumor cells and non-tumor cells. In some cases, tumor cells comprise CTCs. In some embodiments, tumor cells comprise breast cancer cells, cervical cancer cells, lung cancer cells, bladder cancer cells, ovarian cancer cells, esophageal cancer cells, head and/or neck cancer cells, kidney cancer cells, glioma cells, bladder cancer cells, pancreatic cancer cells, colon cancer cells, or a combination thereof.

Further, in some cases, contacting a plurality of cells with the plurality of first aptamer probes (or antibodies) comprises contacting a bodily fluid with the plurality of first aptamer probes (or antibodies). Any body fluid not inconsistent with the objectives of the present disclosure may be used. In some cases, for instance, the bodily fluid comprises blood, saliva, urine, or bladder wash.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1

The "break junction" provides a way to interrogate electrical transport properties of molecules. Selective probe molecules are immobilized between the contact structures with nanometer sized separation. Break junction fabrication was used, including focused ion beam (FIB) "scratching" followed by electromigration, producing elegant, rapid and controlled high-yield nano-manufacturing of break junctions at exact locations with very narrow distribution of the gaps (between electrodes). FIB was used to introduce defects in a lithographically defined metal line by scratching the line surface at specific location. The scratch results in high resistance at that particular scratched part and induced electromigration results in a break at that exact location. Gaps ranging between 100-200 nm have been reproducibly prepared. The break junctions were then functionalized with RNA aptamer molecules and are used to detect an important cancer biomarker Epidermal Growth Factor Receptor (EGFR). EGFR over-expression is known in several types of cancers like breast cancer, lung cancer, cervical cancer, bladder cancer, esophageal cancer, and ovarian cancer. The identification of EGFR as a common element of several cancer types and it being the most common oncogene emphasizes the implication of detecting EGFR at an earlier stage for early diagnosis and better treatment of cancer patients.

A. Method

Figure 8:
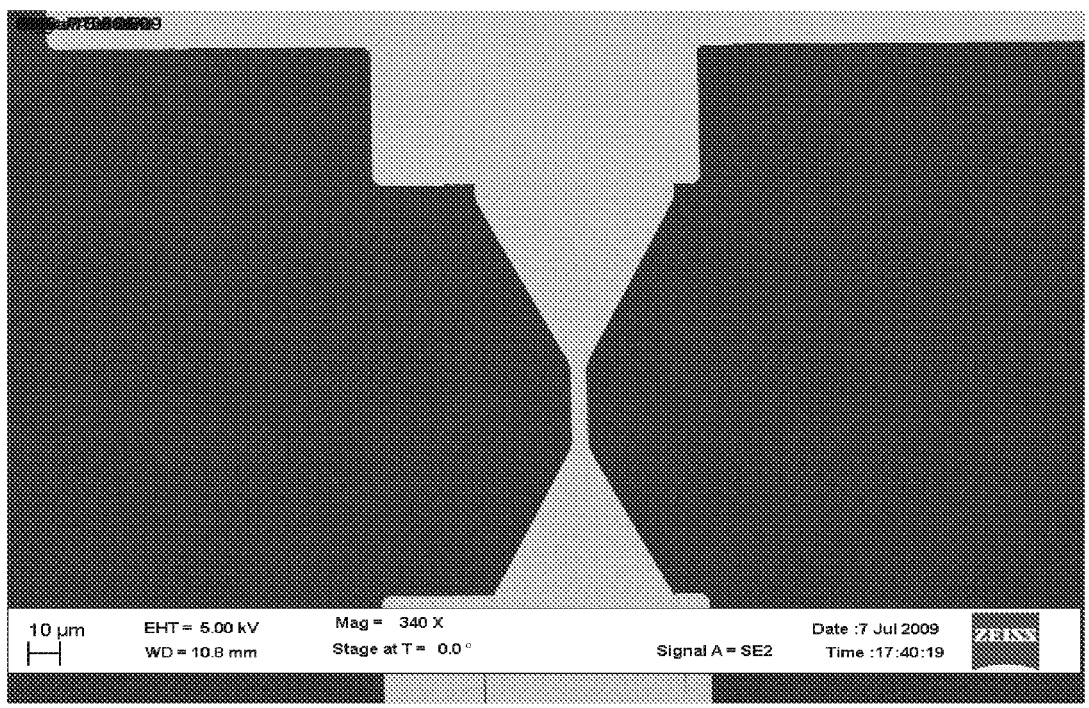
FIG. 8 shows a micrograph of the device of one embodiment of the invention after two-step photolithography and gold lift-off process.
Figure 9:
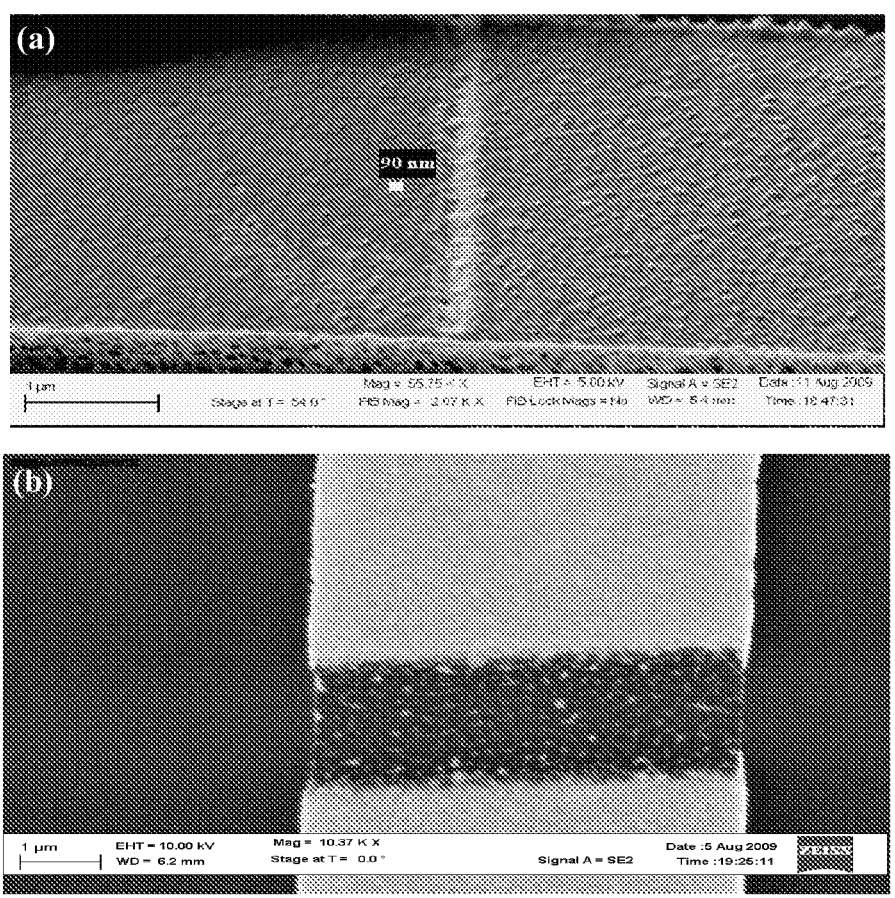
FIG. 9 shows a micrograph of a break-junction chip of one embodiment of the invention after FIB at different process conditions (a) at 30 KV applied voltage, 1 pA milling current and 30 secs of scratching time (b) at 30 KV applied voltage, 20 pA milling current and 120 secs of scratching time.
Figure 10:
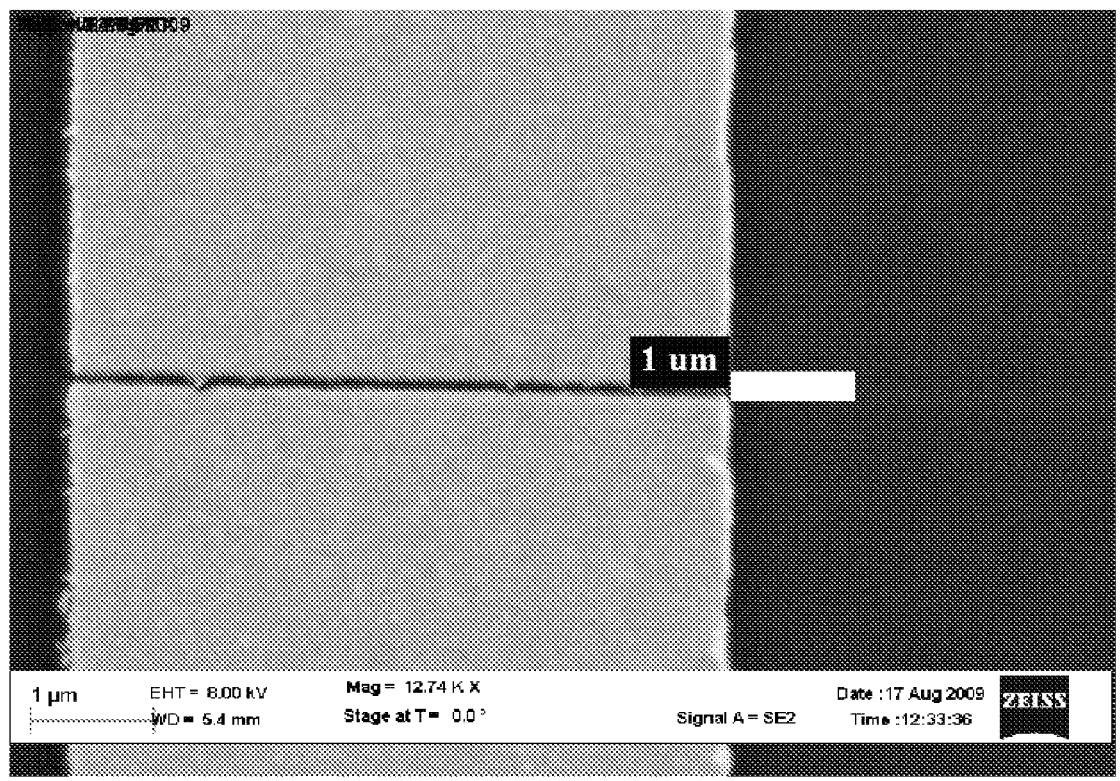
FIG. 10 shows an SEM micrograph of a representative break junction after electromigration of one embodiment of the invention.

The process comprises two-step photolithography for 3 micron lines and the probing pads (FIG. 8). FIB "scratching" was used to remove a thin layer of metal from the lines. The novelty lies in using optical lithography to define the lines, and instead of low-throughput e-beam writing of the full electrode features, FIB writes a 50 nm wide scratch, reducing time to fabricate and increasing throughput. The FIB process depends on applied acceleration voltage, milling current and scratching time. At higher milling current and scratching time, the entire gold layer got removed and also induced defects in $SiO_2$ layer beneath, rendering device un-usable. Secondly the higher milling current produced larger gaps (FIG. 9). FIB process was optimized for narrow break junctions. FIG. 10 shows micrograph of a representative break junction after electromigration. The electromigration results from the application of an external voltage which causes a large current density in the metal lines. When the drifting electrons encounter FIB induced defects, the momentum of the electrons is transferred to the defects which results in the build-up of a force that causes atoms to move away from the defect culminating in the break junction formation. We achieved >60% yield, in comparison to reported yield of <20% by electromigration-only.

The single stranded DNA (ssDNA) were immobilized on the chemically modified silicon dioxide ($SiO_2$) surface underneath the patterned break junctions. The selective RNA aptamers were hybridized with the surface bound ssDNA. After that, the chips were incubated in EGFR buffer solution to capture the protein.

B. Analysis

Figure 11:
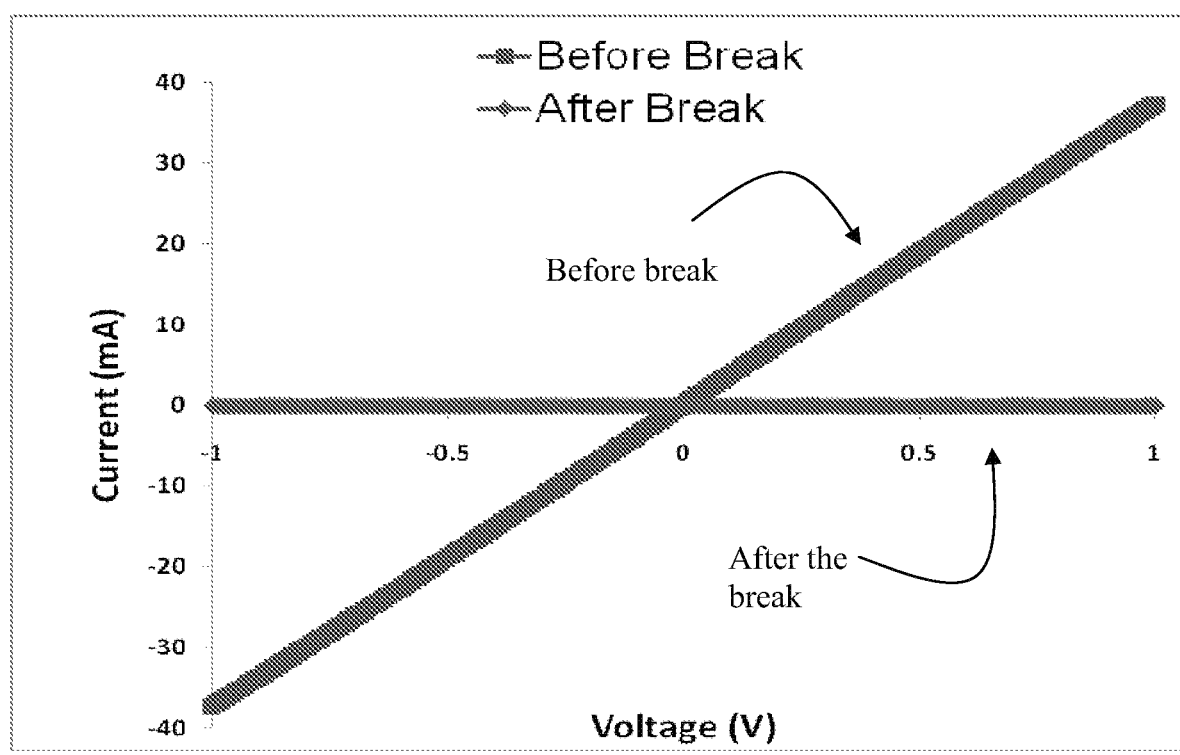
FIG. 11 shows I-V data comparing current through the junction before and after the break.
Figure 12:
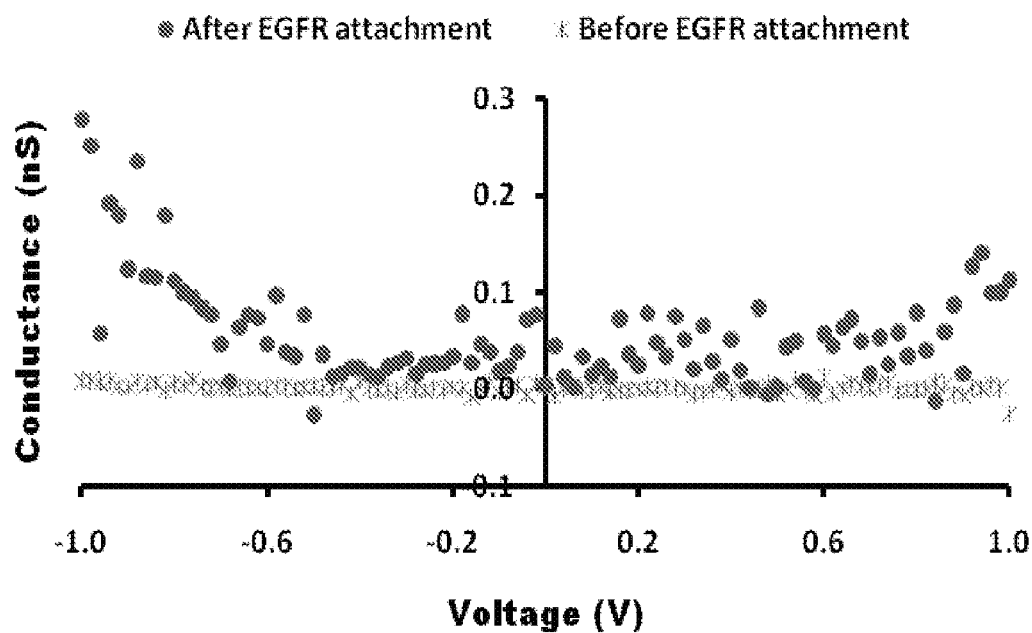
FIG. 12 compares G-V data for a specific break junction before and after the capture of EGFR protein using anti-EGFR aptamer represents a remarkable increase in electrical conductance.
Figure 13:
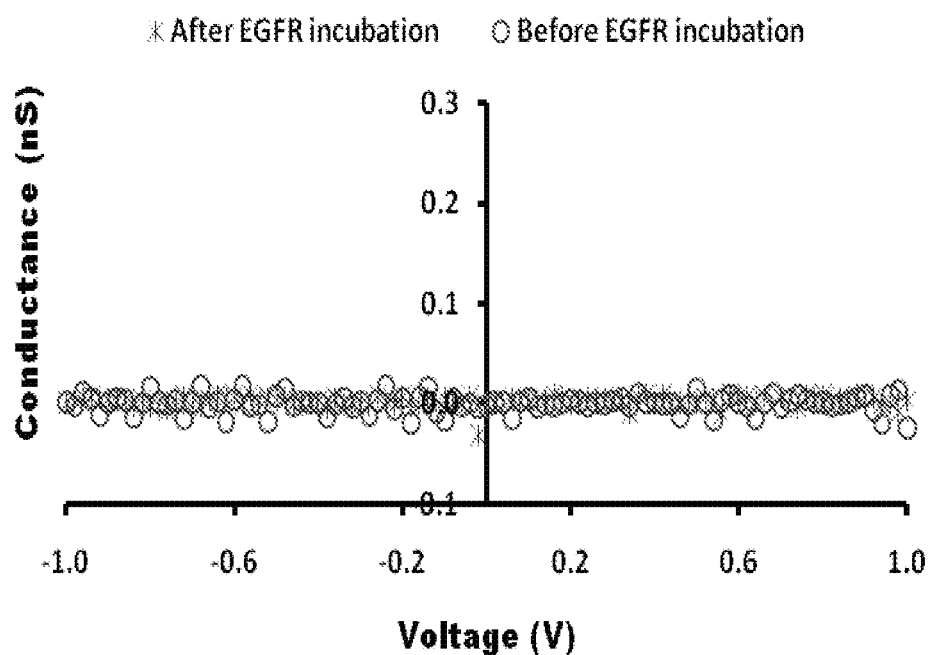
FIG. 13 comparises G-V data for a control break junction before and after the same surface functionlization minus anti-EGFR aptamers shows no change in conducatnce depicting no capture of EGFR proteins.

Current-Voltage (I-V) measurements of break junctions were done before and after FIB scratch, and after electromigration using Agilent 4155C Semiconductor Parameter Analyzer. Following the scratch, a ramping voltage was applied and a sudden drop was seen in the current, representing the complete break, and noticed from complete loss of conductivity (FIG. 11). Once EGFR was selectively captured between the electrodes, increase in the conductivity through the devices was noticed due to the conducting behavior of proteins that bridge the nanogap between the metal electrodes (FIG. 12). The selectivity of the anti-EGFR RNA aptamer to the cancer biomarker was revealed using control chips with no aptamers. The Conductance-Voltage (G-V) data from −1 to 1 V across the electrodes did not show significant change in electrical conductance after EGFR incubation (FIG. 13).

Figure 14:
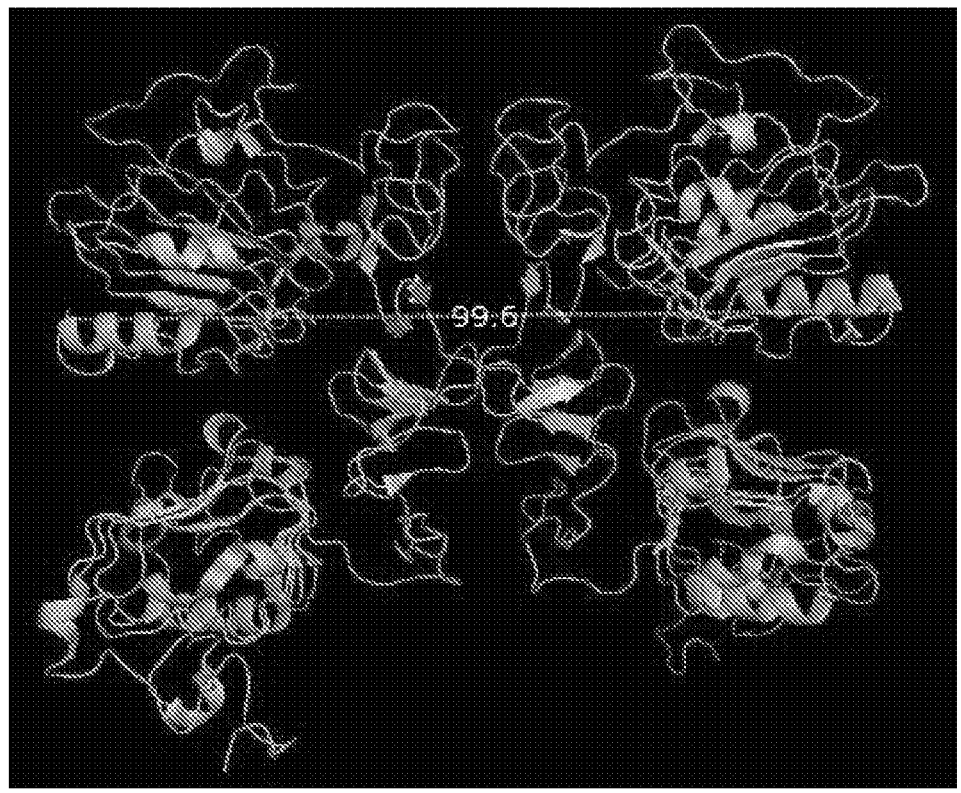
FIG. 14 shows the crystal structure of the extra-cellular region of human EGFR. The measurements (in angstroms) represent the widest points of the structure: (a) Front view, (b) Bottom view. Images are made with PyMOL 1.2.8 (evaluation version).
Figure 14:
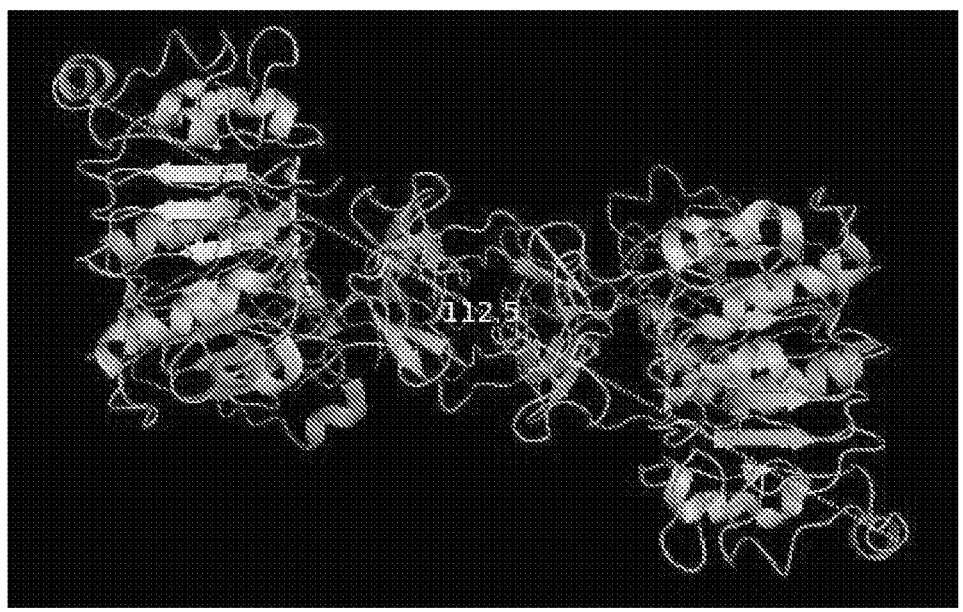

The aptamers are essentially DNA or RNA molecules that are iteratively selected for their specific binding with nucleic acids, proteins, and small organic compounds. Apart from their natural exclusion against biofouling, aptamers can be chemically synthesized, and can be labeled/loaded with various reporters/payload. The aptamers are also stable at various salinity, temperature and surface functionalizations unlike antibody functionalization of devices. Anti-EGFR aptamers have been previously used for the isolation and enrichment of cancer cells. In the current context, the electrical detection of EGFR, selectively captured with surface-bound anti-EGFR aptamer, provides another early diagnosis modality against cancer. EGFR is a large, monomeric, modular glycoprotein with its dimensions on the order of tens of angstroms (FIG. 14). It is expected that the protein structure would expand when it binds to the probe aptamer via its extracellular ligand binding domain. This provides a low demand on the break junction size stringency; proteins (biomarkers or others) even with the break junctions that are larger than just a few nanometers may be detected.

In other words, protein detection does not require sub-10 nm dimensions of break junctions as made with e-beam lithography. Thus, break junctions have come a long way from simple electronic signature studies of atoms/molecules to the detection of highly complex molecules like medically-relevant proteins.

Example 2

A. Materials

The chemicals used were 3'-aminopropyltrimethoxy-silane (APTMS); 1,4-phenylene diisothiocyanate (PDITC); N,N-dimethylformamide (DMF); 1,2-dichloroethane; N,N-diisopropylethylamine (DPEA); 6-amino-1-hexanol; and methanol. Autoclaved de-ionized water (DIW) was used to make the buffer solutions. The chemicals were purchased from Sigma-Aldrich (Saint Louis, Mo.). The 3'-amino modified DNA strands were purchased from Alpha DNA (Montreal, Quebec). The DNA binding domain from the *Bombyx mori* retrotransposon protein R2Bm was prepared. The zinc finger and myb motif of the R2Bm protein binds to a specific dsDNA sequence (5'-CTTAAGGTAGCAAATGC-CTCGTC-3') (SEQ ID NO:6) within the gene coding for the large ribosomal subunit.

B. Method

The reported work consists of three major parts that were carried out in parallel: a) Fabrication of the CMOS chip; b) $SiO_2$ surface preparation, modification and attachment of dsDNA on the Chip; c) Binding between protein and DNA and optical/electrical detection.

a) Fabrication of the CMOS Chip:

Chips were fabricated in two steps of lithography. On the first layers Ti/Au (Thickness 50 Å/150 Å) metal pads 500 nm apart were made using e-beam lithography. Metal lift-off resulted in well-defined structures. In the second step, optical lithography was used to fabricate probing pads to contact the thin film electrodes. The chips were partially fabricated at Birck Nanotechnology Center (Purdue University), Nanotechnology Core Facility (University of Illinois at Chicago) and Nanotechnology Research and Teaching Facility (University of Texas at Arlington). The e-beam lithography was done by xlith (Ulm, Germany).

b) Surface Modification and Attachment of dsDNA:

The silicon chip was cleaned using UV Ozone plasma system. This also resulted in hydrophilic $SiO_2$ surface. The attachment chemistry was performed in a nitrogen glovebox in a controlled environment. Briefly, the chips were silanized in a 3% APTMS solution (made with 19:1 methanol-DIW solution) for over 12 hours. The chips were then cured at 110° C. for 15 minutes. These were then washed with methanol, DIW and dried with nitrogen gas. The chips were then immediately immersed in a DMF solution containing 10% pyridine and 1 mM PDITC overnight. After this, the chips were sequentially washed with DMF and 1,2-dichloroethane and dried under nitrogen gas. The dsDNA sequence solution was prepared at a concentration of 1 pmole/μl and chips were immersed in it immediately. The chips were incubated at 37° C. overnight in order to facilitate the covalent attachment of the 3'-amino modified dsDNA with the PDITC cross linker molecules. The chips were again washed with DIW, methanol and dried under nitrogen. The unbound reactive groups from PDITC were deactivated by immersing the chips in a solution of 50 mM 6-amino-1-hexanol and 150 mM DPEA in DMF for 24 hours. The chips were then washed with DMF, acetone, DIW and dried with nitrogen gas.

In order to confirm the surface modification, Energy-dispersive X-ray spectroscopy (EDAX), contact angle and ellipsometry measurements were carried out at every step. The presence of dsDNA immobilized on the silicon surface was confirmed by fluorescence measurements of Acridine Orange stain at 525 nm wavelength using, using Zeiss Confocal Microscope.

c) Binding Between Protein and DNA:

The dsDNA used in these experiments was a 23 base-pair (bp) fragment of the ribosome gene that corresponds to the binding site of the R2Bm derived polypeptide. In order to confirm that the purified R2Bm polypeptide is capable of binding to the short dsDNA, an electrophoretic mobility shift assay (EMSA) was run.

Chips with covalently attached dsDNA were then incubated with 2.8 fmole/μl of R2Bm polypeptide for 30 minutes in binding buffer (50 mM Tris-HCl pH 8.0, 100 mM NaCl, 5 mM $MgCl_2$). The presence of the protein on the chip was initially confirmed by optical detection of fluorescent Sypro Ruby Protein Blot stain at 488 nm wavelength. The fluorescence intensity analysis was done with ImageJ software. The presence of protein bound to the dsDNA was also detected electrically by direct current electrical measurements.

C. Results

The EDAX analysis was used to identify the elemental composition of the silicon surface as the different modifications were added. The data in TABLE I show the elemental increase in Carbon and Nitrogen after dsDNA immobilization. Control chips without dsDNA showed no change in carbon and nitrogen.

TABLE I

EDAX Analysis - Weight % of Significant Elements on Chips with and without Modifications

|  | C | N | O |
|---|---|---|---|
| Clean Chip | 0.2 | 8.2 | 320.4 |
| PDITC | 7.3 | 9.1 | 329.2 |
| DNA | 10.7 | 25.8 | 391.4 |

The contact angle measurements showed the silicon surface becoming hydrophilic after plasma treatment and later less hydrophilic when functionalized with APTMS and PDITC. This showed that the surface of silicon chip was hydroxyl (—OH) rich after plasma etching. Functionalization with APTMS/PDITC reduced available —OH groups on the surface and thus showed reduced hydrophilicity. This also proved that OH bonds were used up in effective covalent attachment of silane.

The ellipsometry measurements gave the thickness of the self-assembled monolayers (SAM) of silane modification as shown in TABLE II. The difference in the two thicknesses is around ~10 nm. Reaction conditions like temperature, silane concentration, nature of the aminosilane, solvent type, incubation time and more importantly, the amount of adsorbed water, all contribute to the reproducibility of the final structure of the adsorbed aminosilane layer. Our functionalization setup carefully maintained these conditions resulting in reproducible results.

TABLE II

Ellipsometry Measurements (in nm)

|  | Thickness | SD |
|---|---|---|
| Silicon dioxide | 1203.66 | 2.18 |
| APTMS | 1213.35 | 7.32 |

Figure 15:
FIG. 15 is a fluorescence image of dsDNA stained with Acridine Orange on the surface of CMOS chip. Acridine Orange fluoresces green when it interacts with dsDNA.

The presence of dsDNA immobilized on the silicon surface was confirmed by Acridine Orange (FIG. 15). Acridine Orange gives a green fluorescence when it interacts with dsDNA. The Acridine Orange stain bears a positive charge and binds electrostatically with the dsDNA. Electrostatic interactions with non-specific polyanions is avoided by using a very low concentration of the stain (0.2% v/v) and by including other cations like $Mg^{2+}$, $Na^+$ in the buffer solution that would compete for the binding with the dsDNA. Thus, the Acridine Orange stain fluorescence obtained could be taken as a conclusive result of the covalent attachment of dsDNA on CMOS chip surface.

Figure 16:
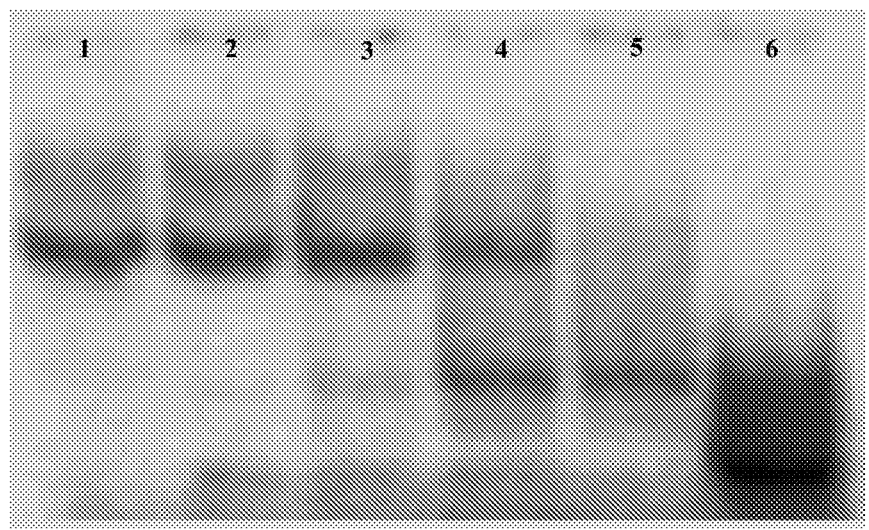
FIG. 16 shows the results of EMSA PAGE gel. The first 4 lanes (from L to R) 8.4 pmole, 2.8 pmole, 0.84 pmole, and 0.28 pmole protein, respectively, of R2Bm protein bound to 1 pM of dsDNA. The last two lanes are dsDNA and ssDNA, respectively, in the absence of protein.
Figure 17:
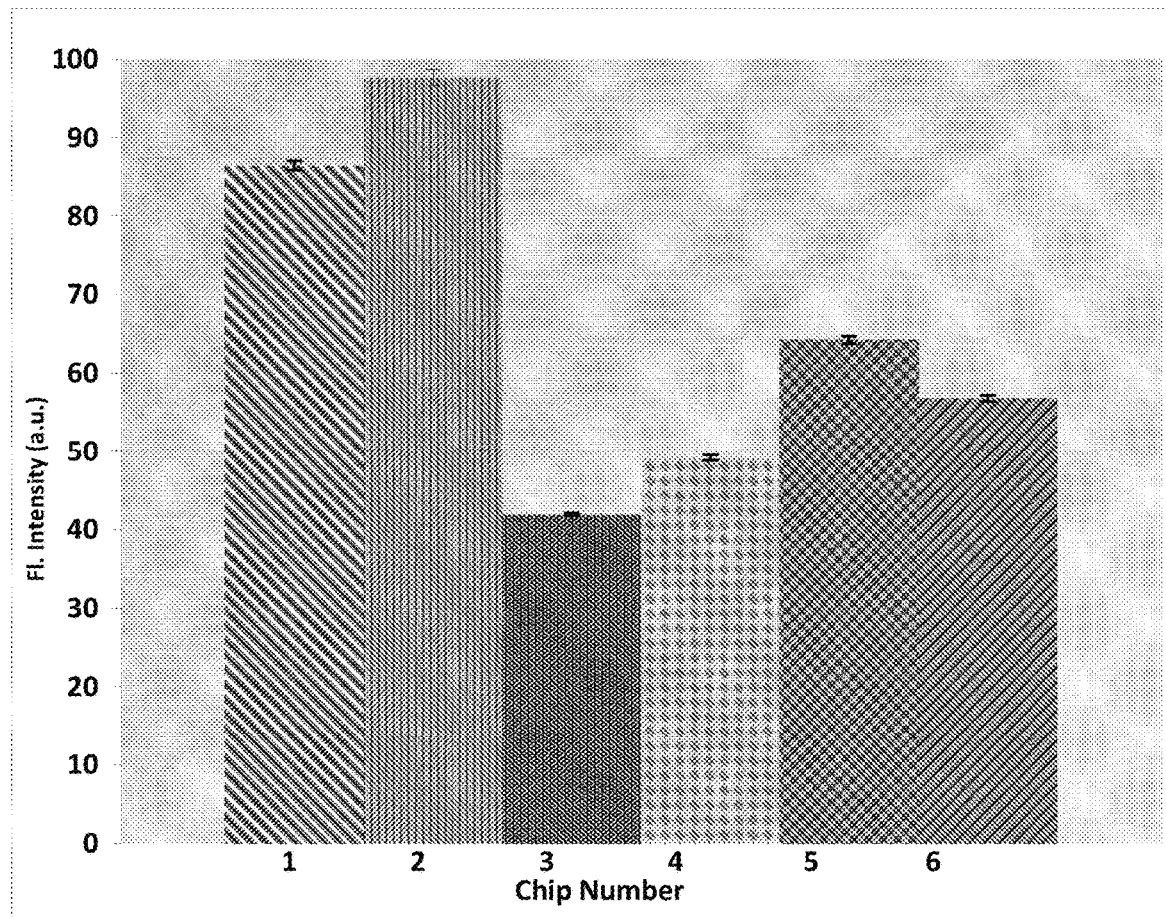
FIG. 17 shows Sypro stain intensity measurements on chips with the following surface modifications: Chip 1 and 2: DNA & protein attached on chip; Chip 3: Only DNA immobilized on chip; Chip 4: Only protein on chip (No DNA); Chip 5: Only APTMS modification on chip surface; Chip 6: Piranha cleaned chip surface (no biomolecule). These results are averages of 10 chips (n=10).

Prior to functionalizing the chips, the polypeptide binding to the 23 bp dsDNA fragment was confirmed using EMSA—a polyacrylamide gel electrophoresis based method to detect protein-DNA interactions (FIG. 16). Importantly, the peptide binding to the DNA was seen on the functionalized chip; FIG. 17 shows the data for the protein stain Sypro Ruby confirming polypeptide binding to dsDNA on chip. The Sypro Ruby stain is a ruthenium based stain that detects the amino acids lysine, Arginine, and histidine.

Figure 18:
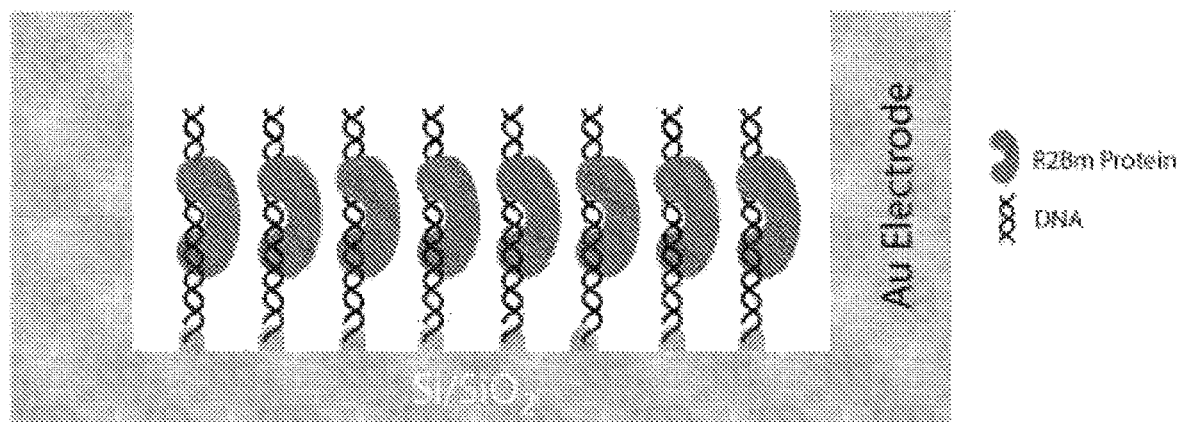
FIG. 18 is a schematic diagram of the attachment of dsDNA and protein on the proteomic biochip on one embodiment of the invention.
Figure 19:
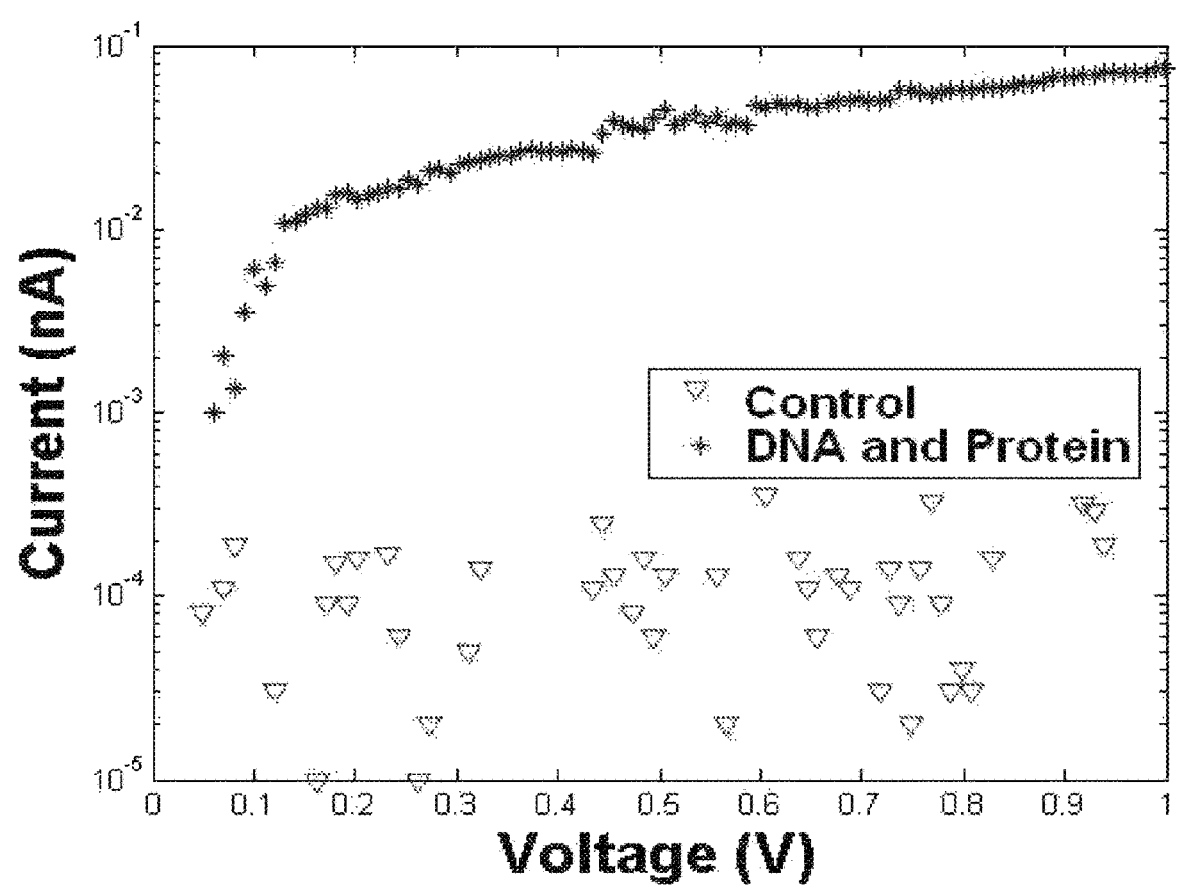
FIG. 19 shows I-V measurements comparing current measured between metal nano-electrodes. Control data is red triangles with no surface bound dsDNA and protein molecules. The blue stars show I-V data for the chip with the DNA and the protein immobilized on its surface.
Figure 20:
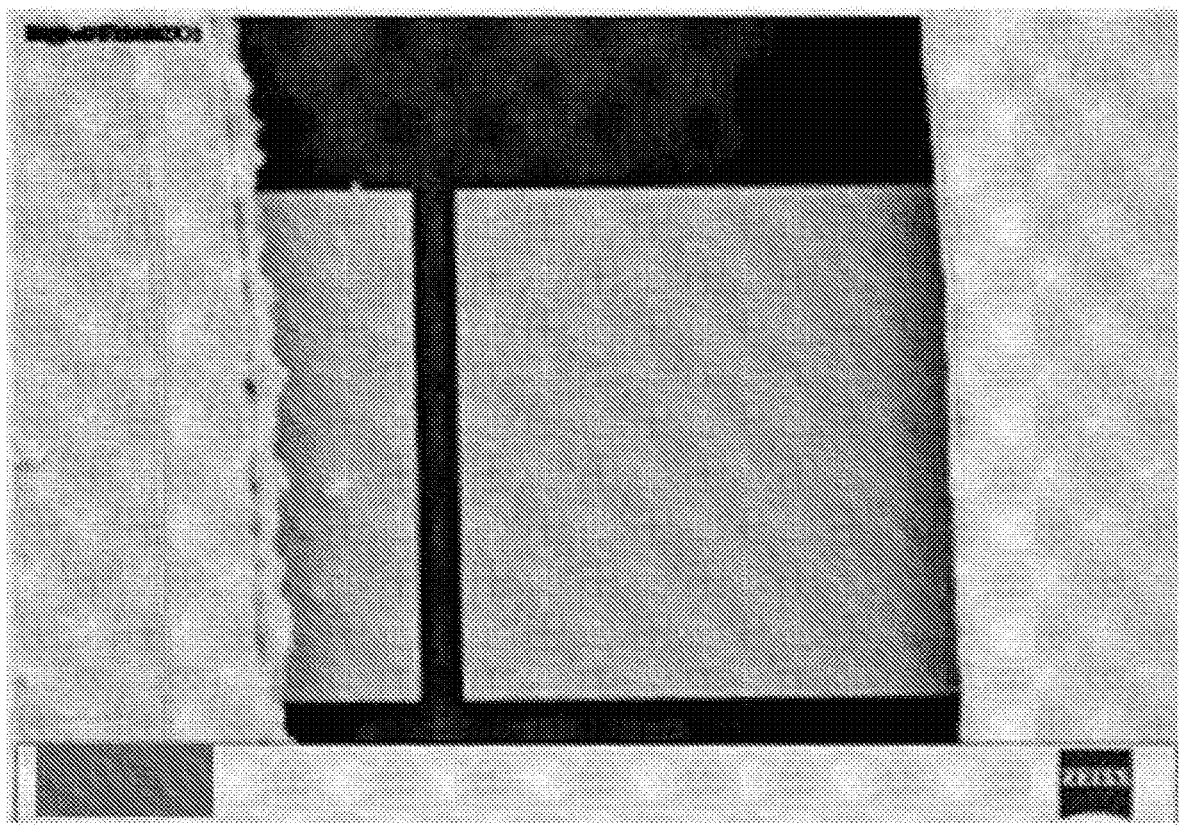
FIG. 20 is an SEM micrograph of the pads. Scale bar: 2 µm.

Once the dsDNA immobilization on silicon chips and selective DNA-protein binding was verified with stains, the dsDNA and protein detection was done on nano-electrode CMOS chip, without any staining. FIG. 18 shows a schematic of the surface bound dsDNA and protein bound to dsDNA between nano-electrodes. FIG. 20 shows an SEM micrograph of the nano-electrodes. The current-voltage (I-V) measurements were performed using Agilent Semiconductor Parameter Analyzer (4155C) on a probe station. A chip without any biomolecules was used a control. The I-V data was recorded from −1 V to +1 V across the metal electrodes 500 nm apart. The I-V data showed linear trend after the capture of proteins on surface immobilized dsDNA. The yield of devices was 20%, which can be substantially increased by using electrodes with lesser separation or by tagging the protein molecule with conducting nanoparticles, e.g. of gold. The I-V data showed a linear trend indicating conducting behavior of the protein. The control chip showed open circuit behavior before and after the functionalization (triangles in FIG. 19). The resistances of the devices after protein capture ranged from few ohms to GΩ, indicating a varying number of proteins bridging the gaps between the electrodes.

A CMOS chip is presented, with electronic recognition of selective protein. The selectivity is achieved by using a dsDNA fragment. The I-V measurements are carried out to detect the capture of the protein. Works describing the capture of folate binding protein using antibodies as the capturing agent report sensitivities such as 130 ng/ml by Surface Plasmon Resonance; 1.5 ng/ml by Quartz Crystal Microbalance; 5-100 ng/ml by Enzyme-Linked Immunosorbent Assay (ELISA) and 50 pg/ml by optical diffraction. Using DNA as the capturing agent, there is a detection capability down to 0.28 pmol (less than a pg/ml) of a protein. Such framework can be easily extended to carry out data acquisition, analysis and decision making on-board the same chip. This new approach is named Proteomic ("protein"+ "electronic") Biochip. With the advent of so called "Omics" revolution, diseases can be defined at both the molecular and the genomic/protein network levels, and proteomic chips can be used to detect disease linked protein biomarkers to speed up diagnosis and therapy. The application of the chips could also be extended to environmental sample analysis as well, such as in bioterrorism to identify dangerous virus or bacteria or to identify contaminants in food and water, etc. Samples from suspect fluids or tissues can be electrically tested for the presence of important biomolecules.

Example 3

Materials and Methods

A. Materials

All chemicals were obtained from Sigma-Aldrich (St. Louis, Mo.) unless otherwise noted.

B. Aptamer Preparation

The anti-EGFR modified RNA aptamer was isolated by iteratively selecting binding species against purified human EGFR from a pool that spanned a 62 nucleotide random region. A high affinity ($K_d$=2.4 nM) anti-EGFR aptamer and a non-functional, scrambled counterpart were extended with a capture sequence. The capture sequence did not disrupt aptamer structures but was used as a hybridization handle for binding with probes immobilized on surface.

The sequences for the extended anti-EGFR aptamer, mutant aptamer, and relevant capture oligonucleotides were:

```
anti-EGFR aptamer
                                               (SEQ ID NO: 1)
(5'-GGC GCU CCG ACC UUA GUC UCU GUG CCG CUA UAA

UGC ACG GAU UUA AUC GCC GUA GAA AAG CAU GUC AAA

GCC GGA ACC GUG UAG CAC AGC AGA GAA UUA AAU GCC

CGC CAU GAC CAG-3');

mutant aptamer
                                               (SEQ ID NO: 2)
(5'-GGC GCU CCG ACC UUA GUC UCU GUU CCC ACA UCA

UGC ACA AGG ACA AUU CUG UGC AUC CAA GGA GGA GUU

CUC GGA ACC GUG UAG CAC AGC AGA GAA UUA AAU GCC

CGC CAU GAC CAG-3');

modified capture oligonucleotide
                                               (SEQ ID NO: 7)
(5'-amine-CTG GTC ATG CGC GGC ATT TAA TTC-3'
or
                                               (SEQ ID NO: 8)
(5'-6FAM-CTG GTC ATG CGC GGC ATT TAA TTC-3').
```

The extension sequence is underlined.

The anti-EGFR aptamer was prepared by transcribing a double-stranded DNA template using Durascribe kits from Epicentre (Madison, Wis.). The DNA template was PCR-amplified, ethanol precipitated, and mixed with reaction buffer, DTT, ATP, GTP, 2' F-CTP, 2' F-UTP, and a mutant T7 polymerase for 10 hours at 37° C. The DNA template was then degraded with DNase treatment for 30 min at 37° C. Aptamer was purified on an 8% denaturing PAGE. The band for the aptamer was visualized by UV shadowing, and the aptamer was excised and eluted in 0.3 M NaAc (pH 5.2) overnight at 37° C. followed by ethanol precipitation. The pellet was dissolved in water, and the concentration of aptamer was measured on a NanoDrop spectrophotometer (Thermo Scientific, Wilmington, Del., USA). The aptamer was modified by extending the DNA template at its 3' end with a 24 nt sequence tag, and then hybridizing the transcribed, extended aptamer with a complementary DNA oligonucleotide (referred to as capture oligonucleotide) labeled with 6-FAM or an amine at its 5' end.

C. Preparation of Anti-EGFR Aptamer/Antibody Functionalized Substrates

The glass slides, used as substrates, were cut into 4×4 mm$^2$ pieces and cleaned in piranha solution ($H_2O_2$:$H_2SO_4$ in a 1:3 ratio) for 10 minutes at 90° C. After rinsing with deionized water (DI water) and drying in nitrogen flow, the glass substrates were immersed in a 19:1 (v/v) methanol:DI water solution containing 3% APTMS for 30 minutes at room temperature. The substrates were then sequentially rinsed with methanol and DI water and cured at 120° C. for 30 minutes. Silanized substrates were then immersed in a dimethylformamide (DMF) solution containing 10% pyridine and 1 mM phenyldiisothiocyanate (PDITC) for 2 hours. Each substrate was then washed sequentially with DMF and 1,2-dichloroethane and dried under a stream of nitrogen. The DNA capture probes with an amine group modification at the 5' end were prepared at 10 μM concentration in DI water with 1% (v/v) N,N-diisopropylethylamine (DIPEA). A volume of 5 μl of DNA solution was placed on each substrate and allowed to incubate in a humidity chamber at 37° C. overnight. Each substrate was then sequentially washed with methanol and diethylpyrocarbonate (DEPC) treated DI water (0.02% v/v). The functionalized surface was then deactivated by capping unreacted PDITC moieties by immersion in 50 mM 6-amino-1-hexanol and 150 mM DIPEA in DMF for 5 hours. Each device was then sequentially rinsed with DMF, methanol and DEPC-treated DI water. The incubator was cleaned with RNase-free and DEPC-treated DI water three times. A volume of 5 μl anti-EGFR RNA aptamer at 1 μM concentration was placed on each substrate in 1× annealing buffer (10 mM pH 8.0 Tris, 1 mM pH 8.0 EDTA, 100 mM NaCl). After 2 hours of hybridization at 37° C., substrates were washed with 1× annealing buffer and DEPC treated DI water for 5 minutes. The negative control devices were hybridized with mutant aptamer using the same protocol. The substrates were placed in 1× (pH 7.5) phosphate buffered saline (PBS) with 5 mM magnesium chloride and kept at −20° C. for one week or used immediately. A 100 μg/ml EGFR antibody solution was placed on the glass substrates, and incubated at 37° C. for 1 hour. Then the substrates were blocked with BSA (10 mg/ml) solution for 20 min and washed thoroughly with PBS, and placed in PBS solution.

D. Genetic Engineering, Isolation and Characterization of EGFR Over-Expressed Mouse Derived Tumor Cells (Ink4a/Arf−/−EGFRvIII Neural Stem Cells)

Embryonic (E13.5) neural stem cells (NSC) were isolated from Ink4a/Arf−/− embryo brain, maintained under standard neuro sphere culture conditions and were infected with a retrovirus expressing the mutant EGFRvIII receptor. The tumorigenicity of these cells have been extensively characterized. The Ink4a/Arf−/−EGFRvIII NSCs were also stably transduced with a lentivirus expressing monomeric-cherry (referred to as m-cherry) fluorescent protein, live-cell imaging and identification.

E. Isolation and Characterization of Human Glioblastoma (hGBM) Cells

Human glioblastoma samples were obtained from consenting patients at the University of Texas Southwestern Medical Center (Dallas, Tex., USA) with the approval of the Institutional Review Board. On average, specimens >50 mm$^3$ were placed into ice cold hank's buffered salt solution (HBBS) media immediately upon removal from the brain. Red blood cells were removed using lympholyte-M (CEDARLANE Labs, Burlington, N.C., USA). The hGBM tumor tissue was gently dissociated with papain and dispase (both 2%), triturated, and then labeled with a CD133/2 (293C3)-PE antibody (Miltenyi Biotec, Auburn, Calif., USA) and sorted with FACSCalibur machine (BD Biosciences, San Jose, Calif.). Both CD133 positive and negative cells were suspended in a chemically defined serum-free Dulbecco's modified Eagle's medium (DMEM)/F-12 medium, consisting of 20 ng/ml mouse EGF (Peprotech, Rocky Hill, N.J., USA), 20 ng/ml of bFGF (Peprotech, Rocky Hill, N.J., USA)), 1×B27 supplement (Invitrogen, Carlsbad, Calif., USA), 1× Insulin-Transferrin-Selenium-X (Invitrogen, Carlsbad, Calif., USA), 100 units/ml:100 μg/ml of Penicillin:Streptomycin (HyClone, Wilmington, Del., USA) and plated at a density of 3×10$^6$ live cells/60 mm plate. Both CD133 positive and negative fractions underwent clonal expansion and formed orthotopic tumors (data not shown). For all the experiments, the CD133 positive fraction, referred to as hGBM cells, was used. The hGBM cells were stably transduced with a lentivirus expressing m-cherry fluorescent protein.

F. Meninge Derived Primary Fibroblast

Rat derived primary meningeal fibroblasts were obtained from postnatal 3 day rat pups. Briefly, meninges were peeled from the cerebral cortices then processed by incubation for 30 minutes in 0.5% collagenase, 20 minutes in 0.06% trypsin/EDTA, and then triturated. Following trituration the cells were plated in T-75 tissue culture flasks in DMEM/F-12 medium containing 10% fetal bovine serum and allowed to grow for one week to confluence.

Results

A. Aptamer Binding to Cultured Tumor Cells

To demonstrate the selective binding of aptamer to tumor cells, the anti-EGFR aptamer, annealed with 6-FAM modified capture oligonucleotide, was incubated with tumor cells and fibroblasts, and interaction was measured as follows: The DNA capture probe labeled with 6-FAM was used as received (Alpha DNA, Montreal, Quebec, Canada). Equal amounts of anti-EGFR RNA aptamer and DNA capture probe were annealed by heating samples to 70° C. for 10 minutes and then slowly cooling to room temperature. Both mouse-derived tumor cells and primary fibroblasts were seeded into separate PDMS wells (8 mm diameter) and cultured for 48 hours. The RNA:DNA capture probe was incubated with cells at 37° C. for 30 minutes under 5% $CO_2$. After incubation, the cells were washed with 1×PBS 3 times, and stored in fresh sterilized 1×PBS for differential interference contrast (DIC) and fluorescence imaging. DIC data was used to image the cells and fluorescence imaging focused on aptamers. Mutant aptamer was also applied into the cells as a control, and all experimental procedures were the same as the anti-EGFR aptamer. The fluorescence images were taken using appropriate filters. The excitation and emission wavelength of 6-FAM is 492 and 517 nm respectively.

B. Tumor Cell Capture Using Anti-EGFR Aptamer/Antibody Substrates

In all experiments, the cell suspensions were centrifuged, the supernatants were removed, and sterilized and warmed 1×PBS solution (with 5 mM $MgCl_2$) was added to dilute the cells. About 50 µl of cell suspension in 1×PBS was placed on each substrate. The substrates were incubated for 30, 60, or 90 minutes at 37° C., and then washed with sterilized 1×PBS solution on a shaker (Boekel Scientific, Feasterville, Pa., USA) at 90 rpm for 6-10 minutes in orbital and reciprocal movements. The time of incubation was also studied for saturation effects. There was no difference seen in the results for the three different groups of 30, 60 and 90 minutes incubation. The buffer evaporation was seen for longer incubation. The subsequent incubations of cells were thus done for 30 minutes. For tumor specific isolation studies, the human GBM cells were mixed with fibroblasts in a 1:1 ratio. Mutant aptamer functionalized substrates were used as a control. The experiments of EGFR capture with antibodies follow exactly the same procedure.

C. Temporal Monitoring of Cellular Interaction Between Tumor Cells and Anti-EGFR Aptamers Functionalized on Substrates To visualize tumor cell capture via the anti-EGFR aptamer substrates, these were placed on a custom-designed neuro-optical microfluidic platform, and the interaction between tumor cells and surface grafted aptamers was monitored. Briefly, the substrates were placed on the platform which maintained 5% $CO_2$ at 37° C. and high humidity for live cell imaging. The cellular interaction between cells and anti-EGFR aptamer surfaces were closely monitored using an inverted microscope (63×: DIC). Images were taken after every 30 seconds, and the interaction was monitored for 30 minutes. The tumor cells were also seeded on the control substrates (with mutant aptamer) and the interaction was closely monitored in a similar manner.

D. Quantification and Statistical Analysis

For analysis, 5 representative images were taken from each substrate. The images were analyzed with Image-Pro Plus software. The total number of captured cells and their relevant diameters on the surface were counted automatically, and the cell densities were calculated. In order to show the diameter of tumor cells on aptamer grafted substrates, the data was sorted into 6 groups based on cell sizes (from 20 µm to the maximum; 5 µm interval) and relevant percentages were obtained.

Discussion

The use of microfluidic devices to isolate rare tumor cells is of great importance. The capture of tumor cells requires the affinity recognition of specific biomarkers. The challenge is to efficiently isolate small number of tumor cells from a much larger pool of normal cells. Aptamers may prove to be uniquely useful for lab-on-chip devices because of their high and specific affinities for analytes, and the versatility of conjugation and labeling inherent in their chemical synthesis. Before the RNA aptamer substrates to identify and isolate EGFR over-expressed cancer cells were used, the specific binding between mouse-derived tumor cells and the anti-EGFR aptamers was confirmed.

A. Aptamer-Binding to Mouse-Derived Tumor Cells

Figure 21:
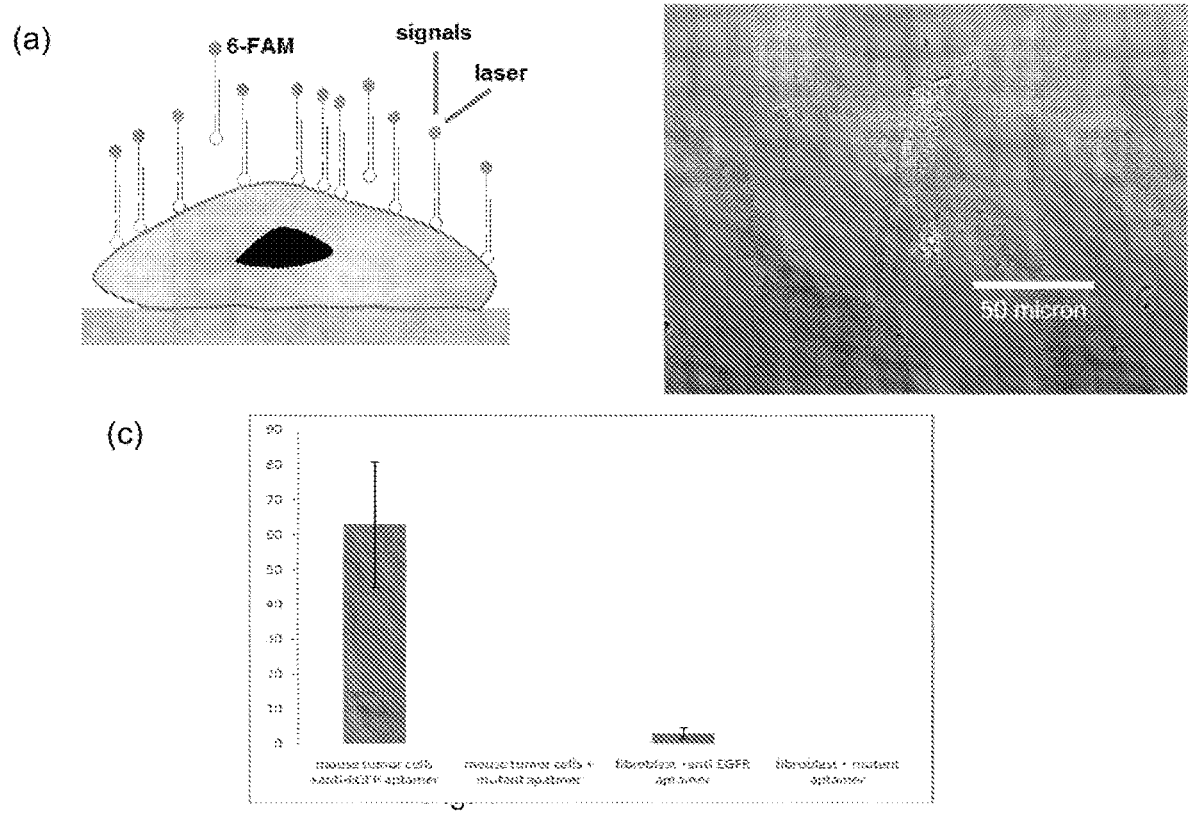
FIG. 21 shows Anti-EGFR aptamer binding to the cultured mouse derived tumor cell. The RNA aptamer was annealed to 6-FAM modified DNA capture probe. The RNA aptamer-DNA probe complex was allowed to interact and bind to mouse-derived tumor cells at 37° C. for 30 minutes in 5% $CO_2$. After binding, the cells were washed with 1×PBS three times. (a) shows schematic depicting mouse derived cell bound with aptamer complex; (b) shows overlaid fluorescent and DIC images. The green fluorescent shows the cell-bound aptamer molecules; (c) shows average fluorescence intensity of each group.

The capture oligonucleotides modified with 6-FAM dye were hybridized to the anti-EGFR and mutant (as control) aptamers and specific binding to cultured mouse-derived tumor cells was observed (FIG. 21(a)). An additional control for specificity was to incubate the anti-EGFR aptamer with a non-cognate cell, primary fibroblasts. After washing, green fluorescence was observed only with the mouse-derived tumor cell surface incubated with the labeled anti-EGFR aptamers (FIG. 21(b)). The controls included: (i) mutant aptamer incubated with mouse-derived tumor cells; (ii) anti-EGFR aptamer with fibroblast; and (iii) mutant aptamer with fibroblasts. The fluorescence intensity data are shown in FIG. 21(c). Similar results were obtained for hGBM cells. This showed the specific binding of anti-EGFR aptamer with tumor cells.

B. Capture and Morphological Characteristics of Mouse Derived Tumor Cells which Over-Express EGFR The functionalization of the substrates yields a homobifunctional layer of PDITC that can be used to immobilize any amine-modified molecules. An amine-bearing capture oligonucleotide was conjugated to the surface, and in turn allowed the capture of the extended aptamer. The capping of un-reacted PDITC end-groups ensured that non-specific adsorption of aptamer did not occur. The use of capture oligonucleotides for the construction of lab-on-chip devices has many advantages: it demonstrates a generalized approach to capture any functional nucleic acid, a distinct advantage relative to the use of proteins; it increases the distance between the substrate surface and the aptamer, alleviating the effects of steric and/or electrostatic hindrance that may come from surface tethering; and it increases the radius of gyration of the aptamer, thereby potentially increasing reactivity. This also resulted into very distinct behavior of cells when interacting with aptamers (discussed later).

Figure 22:
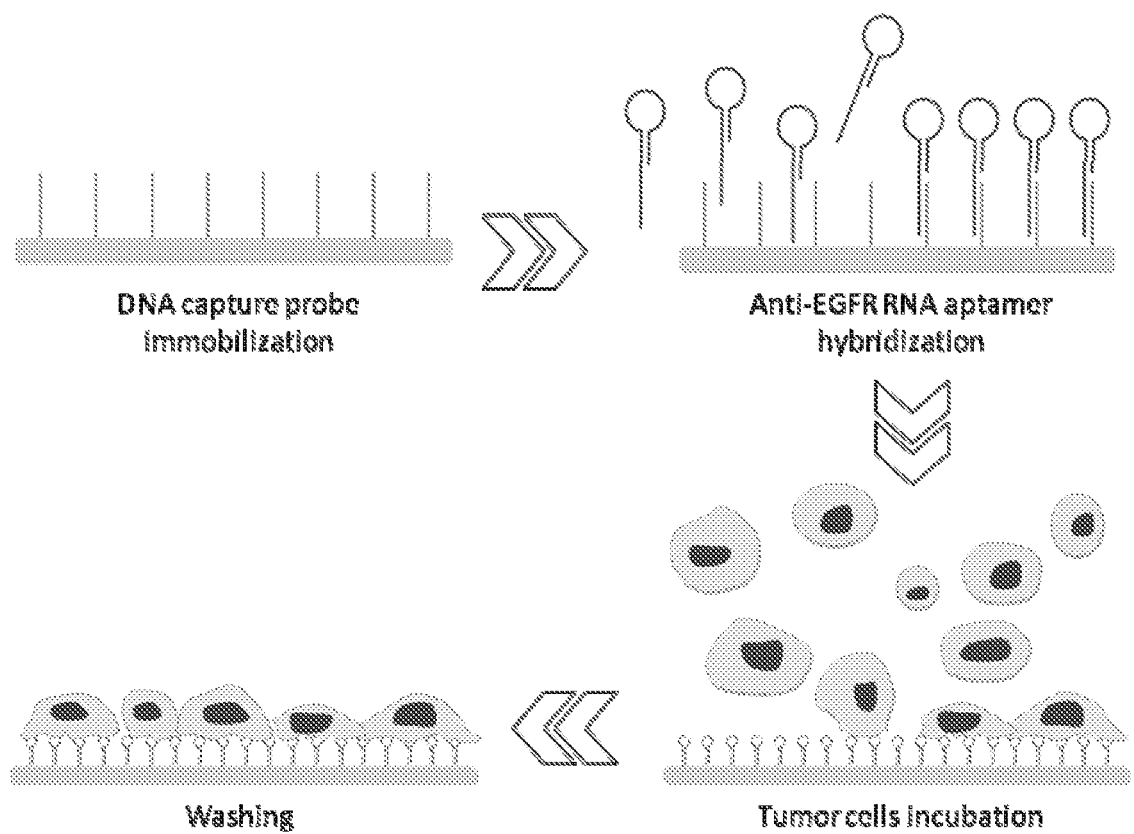
FIG. 22 is a schematic diagram showing steps of experiments. The amine-modified DNA capture probes were first immobilized on the glass substrates. After hybridization with 1 µM anti-EGFR RNA aptamer at 37° C. for 2 hours, substrates were incubated with tumor cells at 37° C. for 30 minutes. After incubation the substrates were washed with 1×PBS for 8 minutes.

Genetically engineered mouse glioma cells were incubated on the aptamer substrates and washed with warmed 1×PBS (FIG. 22). Significantly high numbers of the mouse-derived EGFR over-expressed tumor cells were seen bound to the anti-EGFR aptamer functionalized surfaces (Avg: 392 cells/$mm^2$, Max: 831 cells/$mm^2$, Min: 284 cells/$mm^2$, S.D.: 143.3), with an isolation efficiency of 62.32%. Almost none of the cells were captured on the mutant aptamer functionalized control substrates (Avg: 7 cells/mm², Max: 11 cells/mm², Min: 0 cells/mm², S.D.: 2.8) (FIG. 3).

These results reveal an additional, important feature of the use of nucleic acids on lab-on-chip devices. Nucleic acids may provide a passivation layer that minimizes non-specific adsorption. The hydrophilic surface and electrostatic repulsion may have prevented any non-selective physical adsorption of the cells on mutant aptamer substrates. The density and amount of sialylation on cancer cells surface is known to be higher than normal ones. Carboxyl groups from sialic acid cause a net negative surface charge on cancer cells. The repulsion between negatively charged cells and the negative charges from the surface functionalized aptamer can be another putative reason for the lack of non-specific adsorption. On the other hand, the cancer cells that could selectively interact and bind to the aptamer got captured on the surface, even in the presence of above-stated competing forces. The use of capture oligonucleotides thus has the advantage of reducing non-specific binding or adsorption, adding to the selectivity of the substrates. The use of DNA to covalently immobilize aptamers thus provides a robust passivation of the surface that provides functionality and selectivity while screening effects of surface charges.

Figure 23:
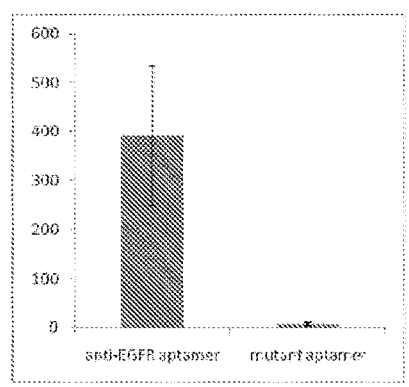
FIG. 23 shows the density and size ranges of captured cells. Devices were incubated with mouse derived tumor cells and washed with 1×PBS. (a) Plot shows average tumor cell density on 12 anti-EGFR aptamer substrates (Avg: 392 cells/m, Max: 831 cells/mm$^2$, Min: 284 cells/mm$^2$, S.D: 143.3) and on 12 control substrates with mutant aptamer (Avg: 7 cells/mm$^2$, Max: 11 cells/mm$^2$, Min: 0 cells/mm$^2$, S.D: 2.8), *$P<0.01$; (b) Plot shows distribution of the diameters of tumor cells on 12 anti-EGFR aptamer substrates; (c) and (d) shows representative tumor cells on mutant aptamer (c) and anti-EGFR aptamer grafted surfaces (d).
Figure 23:
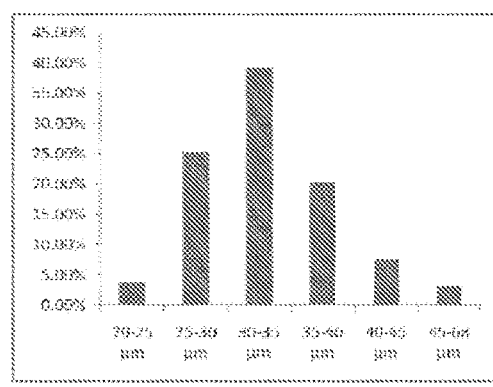
Figure 23:
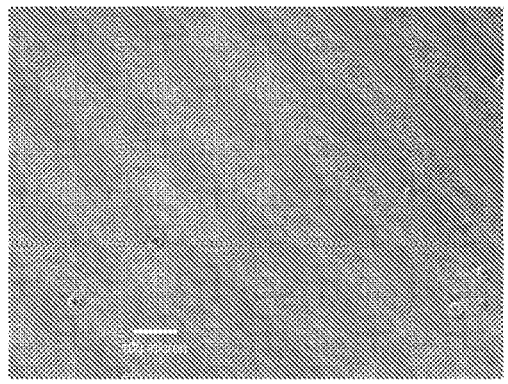
Figure 23:
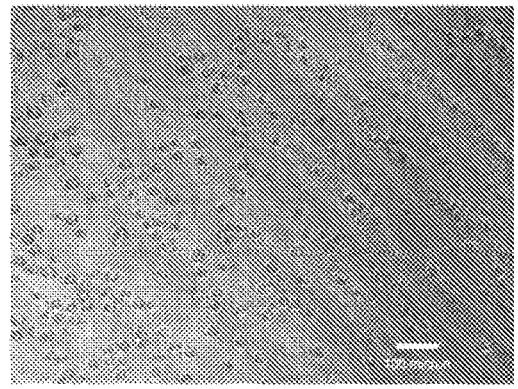

The density and diameters of captured cells showed distinct behavior on the anti-EGFR and mutant aptamer substrates (FIG. 23). On average there were ~392 cancer cells captured per mm² on 12 anti-EGFR aptamer substrates (S.D: 143.3), with the size ranges depicted in FIG. 23(b). Interestingly ~70% of the captured cells had diameters above 30 μm, whereas the size of these cells in suspension ranged between 25-30 μm. This indicates that cancer cells were spreading on the anti-EGFR aptamer substrates. This can serve as a novel and important phenomenon that can be a discriminating factor in cytological studies for the confirmation of the captured tumor cells.

C. Capture of hGBM Cells

EGFR expression level on hGBM cells was lower (approximately 50%) compared to the genetically mouse glioma cells (level verified by western blot, data not shown). Despite the relative lower EGFR expression level, large number of hGBM cells was captured by the anti-EGFR aptamer functionalized substrates. These cells did not bind to mutant aptamer control substrates (FIG. 24).

Figure 24:
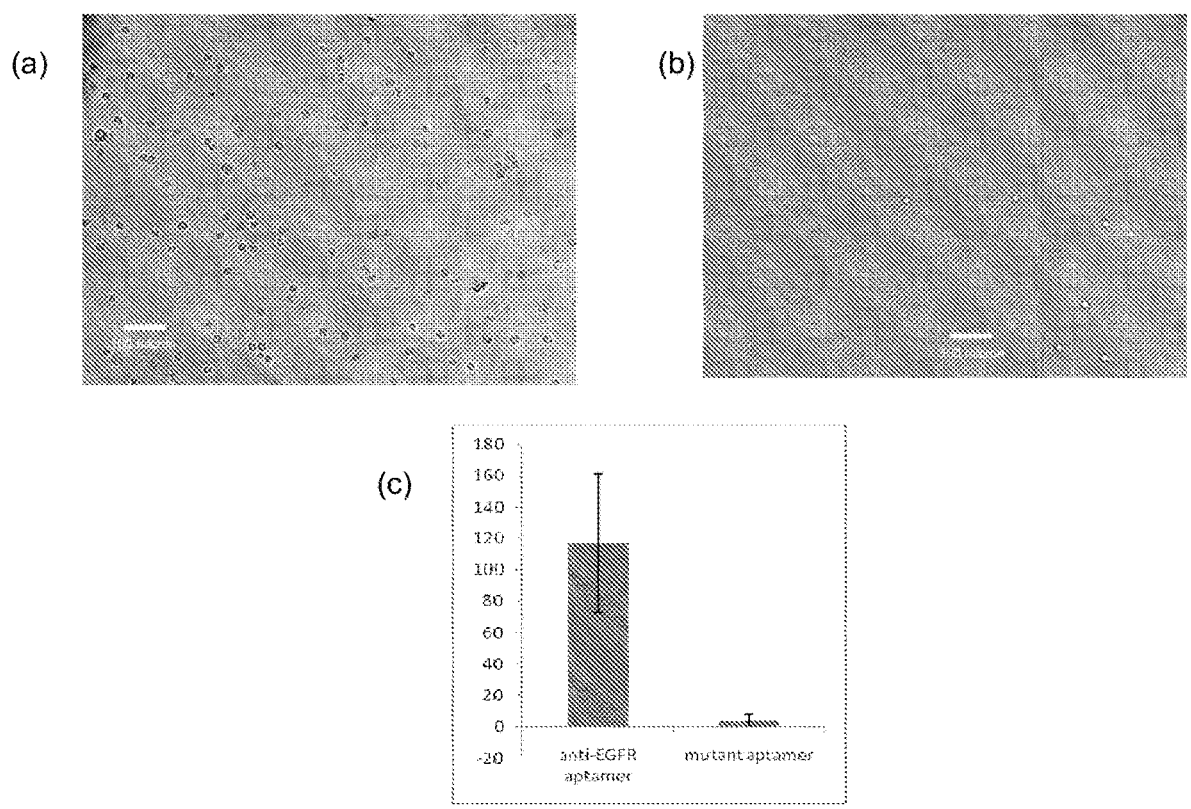
FIG. 24 shows human GBM cells on the substrates. Devices were incubated with hGBM and washed with PBS. The hGBM cells captured on (a) the anti-EGFR aptamer substrate and (b) mutant aptamer control substrate. (c) Plot shows average hGBM cells density on 12 anti-EGFR aptamer substrates (Avg: 117 cells/mm$^2$, Max: 228 cells/mm$^2$, Min: 56 cells/mm$^2$, S.D: 44.4) and on 12 control substrates with mutant aptamer (Avg: 4 cells/mm$^2$, Max: 13 cells/mm$^2$, Min: 0 cells/mm$^2$, S.D: 4.1) (*$P<0.01$).

FIG. 24 shows the clear difference in the number and cell shapes of hGBM cells on anti-EGFR and mutant aptamer substrates. Along with difference in the numbers of captured cells, the shapes of the cells bound with aptamers and adsorbed on mutant aptamer surfaces were also quite different (discussed later). Analysis of 12 substrates showed that on average 117 hGBM cells were captured per mm² on anti-EGFR aptamer substrate (S.D: 44.4, max and min of 228 and 56 cells/mm², respectively), with isolation efficiency of 38.74%. In the control mutant substrate group average density of 4 cells/mm² was seen (S.D: 4.1, max and min densities of 13 and 0 cells/mm² respectively). In comparison to the mouse derived tumor cells, fewer number of captured hGBM cells than that for mouse-derived tumor cells (discussed in previous section) can be explained in terms of overly high number of EFGR that were genetically engineered in mouse derived tumor cells. The decreased density of captured hGBM cells was thus as expected.

D. Isolation of Cancer Cells from Cell Mixture

Figure 25:
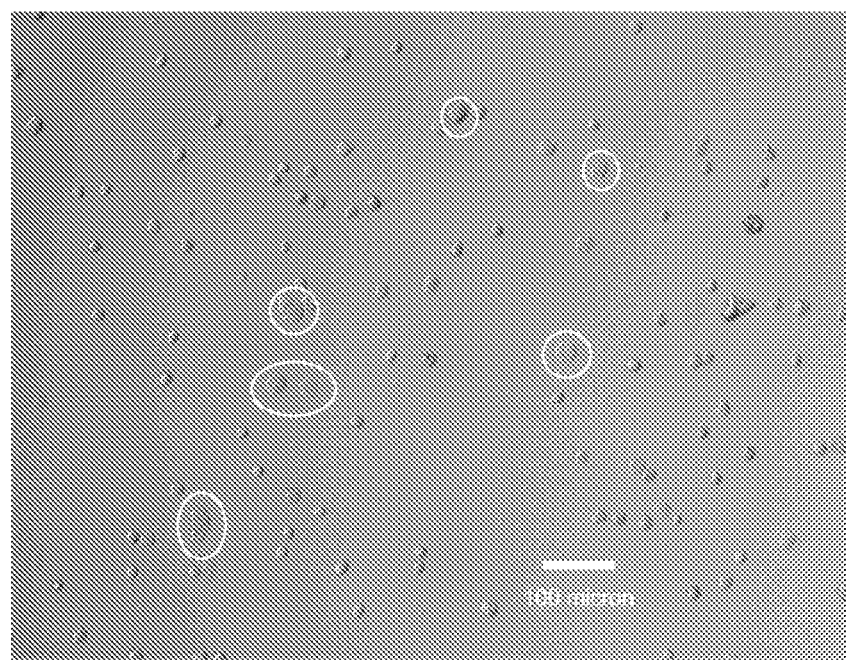
FIG. 25 shows the hGBM cells and fibroblast on the substrate surfaces. Substrates were incubated with mixture of hGBM and fibroblast and washed with PBS. (a) and (b) are DIC and fluorescent images respectively from same position. The circles in (a) indicate a few fibroblasts that were captured and cannot be seen in (b).
Figure 25:
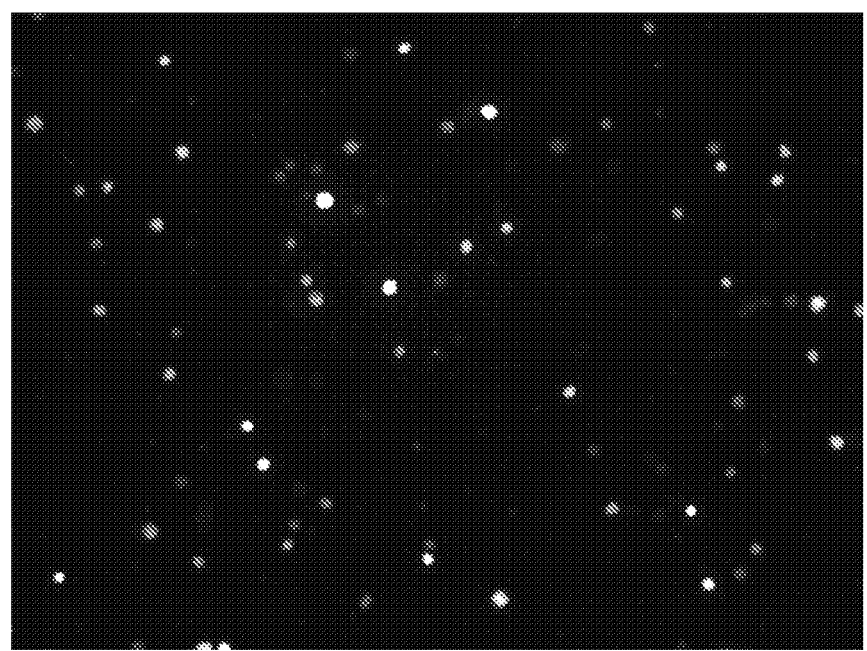

In above two experiments (mouse-derived tumor cells and primary hGBM cells), it was confirmed that the anti-EGFR aptamer functionalized substrates could capture significantly more tumor cells as compared to that with the mutant aptamer. Towards the application of aptamer functionalized substrates in isolating tumor cells and study their behavior, a cell mixture was used. A mixture of hGBM and fibroblast cells was prepared in a ratio of 1:1. The substrates were incubated in the mixture, washed and the results were imaged. In parallel experiments, only hGBM cells were incubated with substrates. Both DIC and fluorescent images were taken (FIGS. 25(a) and 25(b)). In hGBM-only surfaces, the fluorescent intensities were not uniform when DIC and fluorescent images were overlaid (hGBM cells were modified to expressed m-cherry fluorescent protein for clear differentiation). There were about 16.7% cells from 12 substrates (189 out of 1133 cells, Average: ~16, S.D: 5.1) that did not show any fluorescence. The data from the mixture group showed no fluorescence from about 27.5% cells from 12 substrates (378 out of 1376 cells, Average: 31.5, S.D: 6.8). The cells that did not show up in fluorescence images included captured hGBM and non-specifically bound fibroblast cells. The difference of the two percentages, as a first order approximation, shows that on average about 10.8% captured cells were fibroblasts. Thus the anti-EGFR aptamer substrates can selectively isolate and enrich a 1:1 mixture suspension of fibroblasts and cancer cells to 1:8.24 on the surface. In EGFR antibody substrates control group, the ratio of captured fibroblasts and cancer cells was 1:2.77. The specificity of aptamer and antibody on cancer cell isolation was thus 94.82% and 68.81% respectively. The results show aptamer has higher specificity. In a practical scenario, as a lower limit, the aptamer grafted substrates can enrich the amount of cancer cells by an order from the concentration in the solution. In a cyclic iteration application, a sample can be run for multiple times over the substrates to increase the capture efficiency. It may be important to note here that "mean capture yield" using Anti-EpCAM antibodies has been shown to be ~65%.

E. Shape and Size of Cancer Cells on Functionalized Substrates

Figure 26:
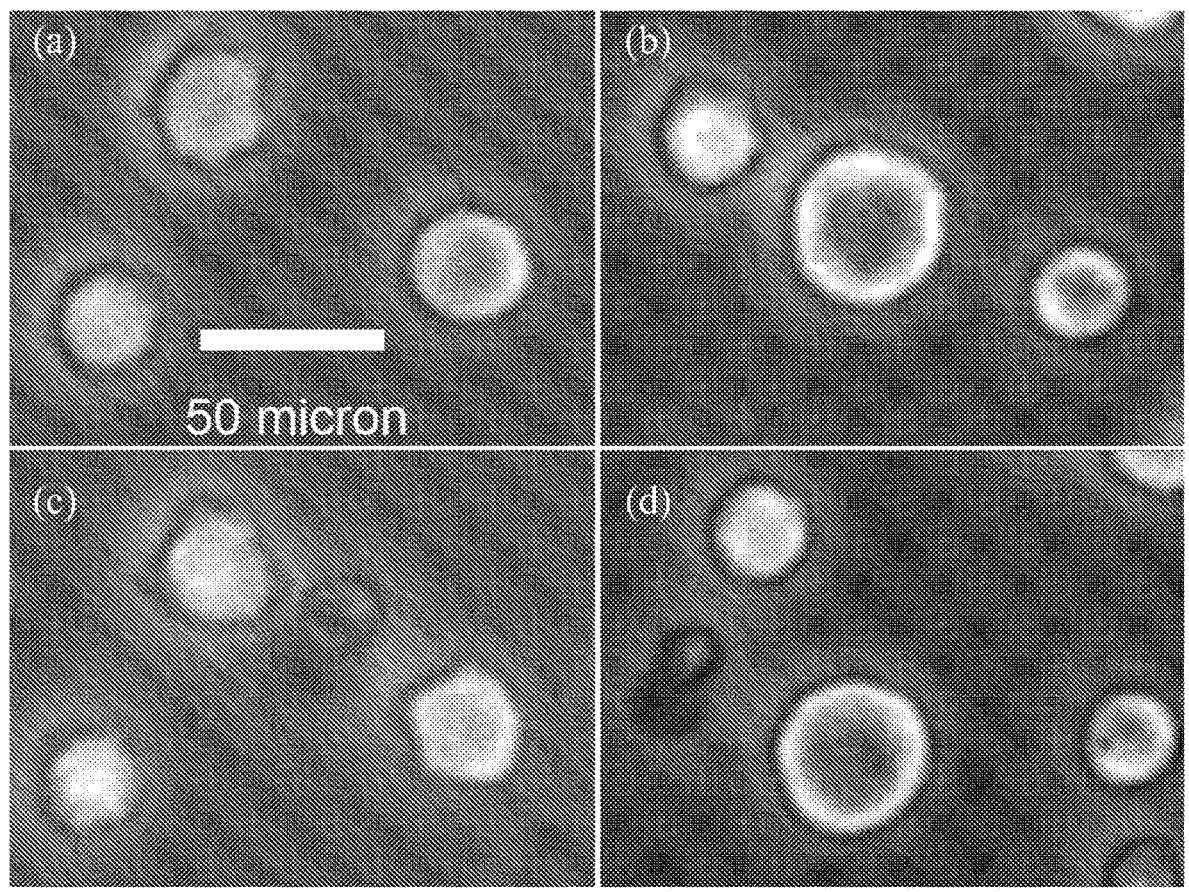
FIG. 26 shows the changes in shapes of mouse-derived tumor cells. (a) and (c) were taken 3 minutes after seeding the cells on the anti-EGFR and mutant aptamer substrates, respectively. (c) and (d) were taken 30 minutes later on the anti-EGFR and mutant aptamer substrates, respectively. (a) to (c) shows the change of cell shapes on the anti-EGFR aptamer grafted surface in 30 minutes. (b) to (d) shows no changes in cell shape cells on mutant aptamer substrates.

In all the experiments, the cell shapes and sizes showed a distinct behavior: fibroblast altered their fusiform, stellar or irregular shape to spherical. The fibroblast cells have normal EGFR expression on their cell membrane but the amount of EGFRs are far less than those for hGBM or mouse derived tumor cells. To bind with anti-EGFR aptamer the cells altered their shape to decrease their surface area to increase the EGFR density that would come in contact with the surface bound aptamer. The temporal images of mouse-derived tumor cells also showed changes in cell shapes from spherical in suspension to semi-elliptical and flat on the aptamer-grafted surfaces. The possible reason between different cell behavior on surface maybe a result of different elasticity that is known to be different in cancer cells. The EGFR over-expressed cells were re-shaping to cover as large of an area as possible. Temporal imaging also showed tumor cell growth and lots of activity on surfaces. FIGS. 26(a) and 26(c) were taken at the beginning when mouse-derived tumor cells were seeded on the anti-EGFR and mutant aptamer surfaces, and FIGS. 26(c) and 26(d) were taken after 30 minutes. Changes in cells shapes and flatness are evident in FIGS. 26(a) to 26(c) and from 26(b) to 26(d). The size of cells also became bigger, and many antennae formed during the incubation period on anti-EGFR aptamer substrates. The data shows that the tumor cells on the substrate surface had strong activity and were arbitrariliy changing their shape. In contrast, in FIGS. 26(c) and 26(d), where first, only much fewer cells did get capture on the mutant aptamer surfaces, and second, those too faced repulsion from the hydrophilic glass surface and the negative charges from the immobilized oligonucleotides. As a result, the cells had almost no change in their sizes during the 30 minutes. The data on hGBM cell shapes in FIG. 26(b) also show that cells on mutant aptamer substrates maintained globular shape as discussed above. The spreading and flatness of cancer cells on aptamer surfaces can be an important modality for detection, as an additional method to support histological findings and further identify tumor cells based on their physical behaviors. In addition, hGBM cells are diffusively infiltrative and current methods to define tumor margins for surgical resection, using MR imaging, are inadequate. Histological evidence suggests that tumor cells at the leading edge may express high levels of EGFR. It is possible, therefore, that freshly resected tumor could be enzymatically dissociated and captured on the anti-EGFR aptamer functionalized substrates, in real time, to better define tumor margins. Such information, thus, can help guide the extent of tumor resection as well. There is considerable evidence that the extent of resection is directly related to overall survival. Beyond the specific application for management of hGBM tumors, our findings are especially important given that enrichment of rare CTCs may be difficult for virtually any lab-on-chip device. The use of aptamers leads both to high passivation and the presentation of unique physical morphologies, and thus may be a novel first level detection step in point-of-care examination of CTCs.

Conclusions

It has been demonstrated that anti-EGFR RNA aptamer substrates can specifically recognize, capture and isolate cancer cells that are known to over-express EGFR. The aptamers selectively captured mouse derived tumor cells which after genetic modification over-expressed EGFR on the cell membrane. Aptamer substrates also specifically isolated human GBM cells from a mixture of fibroblasts. The isolation efficiency depended on strong binding between aptamer and the amount of EGFR expression on the cell membrane. The change in cell shape and cellular activity can serve as a novel way of identifying tumor cells. The substrates can also be used for identification and isolation of CTCs from peripheral blood, dramatically changing intervention and prognosis of metastasis.

Example 4

Materials and Methods

A. Materials

All chemicals were obtained from Sigma-Aldrich (St. Louis, Mo.) unless otherwise noted.

B. Aptamer Preparation

Purified human EGFR (R&D systems, Minneapolis, Minn.) was used for anti-EGFR RNA aptamer preparation via selecting binding species. The EGFR protein was purified from murine myeloma cells, and contained the extracellular domain of human EGFR (Leu25-Ser645) fused to the Fc domain of human lgG1 (Pro 100-Lys 330) via a peptide linker (IEGRMD). The anti-EGFR aptamer ($K_d$=2.4 nM) and a mutant aptamer were extended with a capture sequence. The extended capture sequence did not participate in aptamer hairpin structure but was used to immobilize aptamer on the substrate through duplex formation with substrate anchored probe. The sequences of the extended anti-EGFR aptamer, extended mutant aptamer, and substrate anchored probe were:

```
anti-EGFR aptamer
                                     (SEQ ID NO: 3)
(5'-GGC GCU CCG ACC UUA GUC UCU GUG CCG CUA UAA

UGC ACG GAU UUA AUC GCC GUA GAA AAG CAU GUC AAA

GCC GGA ACC GUG UAG CAC AGC AGA GAA UUA AAU GCC

CGC CAU GAC CAG-3');

mutant aptamer
                                     (SEQ ID NO: 4)
(5'-GGC GCU CCG ACC UUA GUC UCU GUU CCC ACA UCA

UGC ACA AGG ACA AUU CUG UGC AUC CAA GGA GGA GUU

CUC GGA ACC GUG UAG CAC AGC AGA GAA UUA AAU GCC

CGC CAU GAC CAG-3');

substrate anchored probe
                                     (SEQ ID NO: 5)
(5'-amine-CTG GTC ATG GCG GGC ATT TAA TTC-3').
```

The extended capture sequence is underlined. The aptamer was modified by extending the DNA template at its 3' end with a 24 nucleotide sequence tag, and then hybridizing the transcribed, extended aptamer with a complementary substrate anchored probe modified with an amine at its 5' end.

C. Preparation of Nano-Textured PDMS Substrates

Half gram of poly(lactic acid)/poly(glycolic acid) (PLGA; 50/50 wt %; 12-16.5×10$^3$ MW; Polysciences, Inc.) was dissolved in 8 ml of chloroform at 55° C. for 40 minutes. The solution was cast into glass petri dishes, allowed to sit overnight, and was put into a vacuum chamber (15 in Hg) for 2 days at room temperature. The solid PLGA polymers were treated with 10 N NaOH for 1 h to generate nanostructured surfaces, and further sterilized by soaking in ethanol for 24 h followed by exposure to UV light for 1 hour. SYLGARD 184 Silicon Elastomer (Dow Corning, Midland, Mich.) was mixed (10:1, wt/wt) with a silicon resin curing agent. The mixture was first placed in a vacuum chamber to remove all bubbles. The elastomer was then cast onto NaOH treated PLGA polymer surface, and was then allowed to cure for 48 h at room temperature. Finally, the PDMS was peeled from the PLGA. Before the surface modification, the PDMS substrates were immersed into DI water at 37° C. overnight to completely remove any residual PLGA.

D. SEM and AFM Characterization

Zeiss Supra 55 VP scanning electron microscope was used to qualitatively evaluate PDMS surface topography. Samples were sputter-coated with gold at room temperature and visualized at 100× magnification at 5 kV acceleration voltage. Surface topography was quantitatively evaluated using Dimension 5000 AFM. The changes in surface area and root mean square surface roughness were measured. Height images of PDMS samples were captured in the ambient air at 15-20% humidity at a tapping frequency of approximately 300 kHz. The analyzed field was 3 µm×3 µm at a scan rate of 1 Hz and 256 scanning lines.

E. Attachment of Anti-EGFR Aptamer on PDMS and Glass Substrates

The PDMS substrates and the glass slides were cut into 5×5 mm$^2$ pieces and cleaned with UV Ozone plasma and piranha solution ($H_2O_2$:$H_2SO_4$ in a 1:3 ratio) for 30 and 10 minutes respectively. After rinsing with deionized (DI) water and drying in nitrogen flow, the PDMS and glass substrates were immersed in 2% (v/v) of APTES and methanol solution for 30 min at room temperature. The substrates were then sequentially rinsed with methanol and DI water.

The amino groups on PDMS and glass substrates were converted to the isothiocyanate groups by introducing a 0.5% (v/v) thiophosgene solution in acetonitrile for 20 min at 40° C. The substrates were then washed with DI water and dried in a stream of nitrogen. The amino modified DNA capture probes were prepared at 30 μM concentration in 5 mM tris buffer with 50 mM NaCl. A volume of 5 μl of DNA solution was placed on each substrate and allowed to incubate in a humidity chamber at 37° C. overnight. Each substrate was then washed with DI water. Salmon sperm DNA was used for prehybridization to reduce RNA physical adsorption. A volume of 5 μl anti-EGFR RNA aptamer at 1 μM concentration was placed on each substrate in 1× annealing buffer (10 mM pH 8.0 Tris, 1 mM pH 8.0 EDTA, 100 mM NaCl). After 1 hour of hybridization at 37° C., substrates were washed with 1× annealing buffer and DI water for 5 minutes. The negative control devices were hybridized with mutant aptamer using the same protocol. The substrates were placed in 1× (pH 7.5) phosphate buffered saline (PBS) with 5 mM magnesium chloride and used immediately.

F. Contact Angle Measurements

Contact angles were measured on isothiocyanate group modified PDMS (with/without nano-texturing), unmodified PDMS (with/without nano-texturing), and glass (with/without isothiocyanate groups modification). A droplet of DI water was placed on the surface of the substrate at room temperature, and after 30 s, the contact angle was measured using a contact angle goniometer (NRL-100, Rame-Hart). Average of five measurements were utilized for each droplet.

G. Fluorescence Measurements of Fluorescamine

Surface modification was further confirmed by fluorescence measurements of fluorescamine. The density of surface-grafted amino groups from APTES was measured by fluorogenic derivatization reaction with fluorescamine. A mixture of 900 μl of 0.1% (w/v) fluorescamine dissolved in acetone, 150 μl of 0.1 M borate buffer and 1.91 ml DI water was made. After APTES modification, glass, PDMS and nanostructured PDMS samples were immersed into fluorescamine mixture solution for 5 min at room temperature. All samples were rinsed with acetone to remove the excessive reagents. The fluorescence measurements were taken at 390 nm wavelength using Zeiss Confocal Microscope. The fluorescence intensities were analyzed with ImageJ software.

H. Human Glioblastoma and Meninge Derived Primary Fibroblast Cells Culture

The hGBM cells were cultured in a chemically defined serum-free medium: Dulbecco's modified Eagle's (DMEM)/F-12 medium supplemented with, 20 ng/ml mouse EGF (Peprotech, Rocky Hill, N.J., USA), 20 ng/ml of bFGF (Peprotech, Rocky Hill, N.J., USA)), 1×B27 supplement (Invitrogen, Carlsbad, Calif., USA), 1× Insulin-Transferrin-Selenium-x (Invitrogen, Carlsbad, Calif., USA), Penicillin: Streptomycin (100 units/ml:100 μg/ml) (HyClone, Wilmington, Del., USA) and plated at a density of $3\times10^6$ live cells/60 mm plate. The hGBM cells were stably transduced with a lentivirus expressing m-cherry fluorescent protein. The primary rat meninge derived fibroblasts were plated in T-75 tissue culture flasks in DMEM/F-12 medium containing 10% fetal bovine serum.

I. Tumor Cell Capture on Substrates

The cell suspensions were centrifuged, the supernatants were removed. Sterilized and warmed 1×PBS solution (with 5 mM $MgCl_2$) was added to dilute the cells. About 500 μl of cell suspension in 1×PBS was placed on each substrate surface. The substrates were incubated for 30 minutes at 37° C., and then washed with sterilized 1×PBS on a shaker at 90 rpm for 15 minutes. For tumor specific isolation studies, the GBM cells were mixed with fibroblasts in a 1:1 ratio.

Results and Discussion

A. Surface Topography of Nano-Textured Polymers

Figure 27:
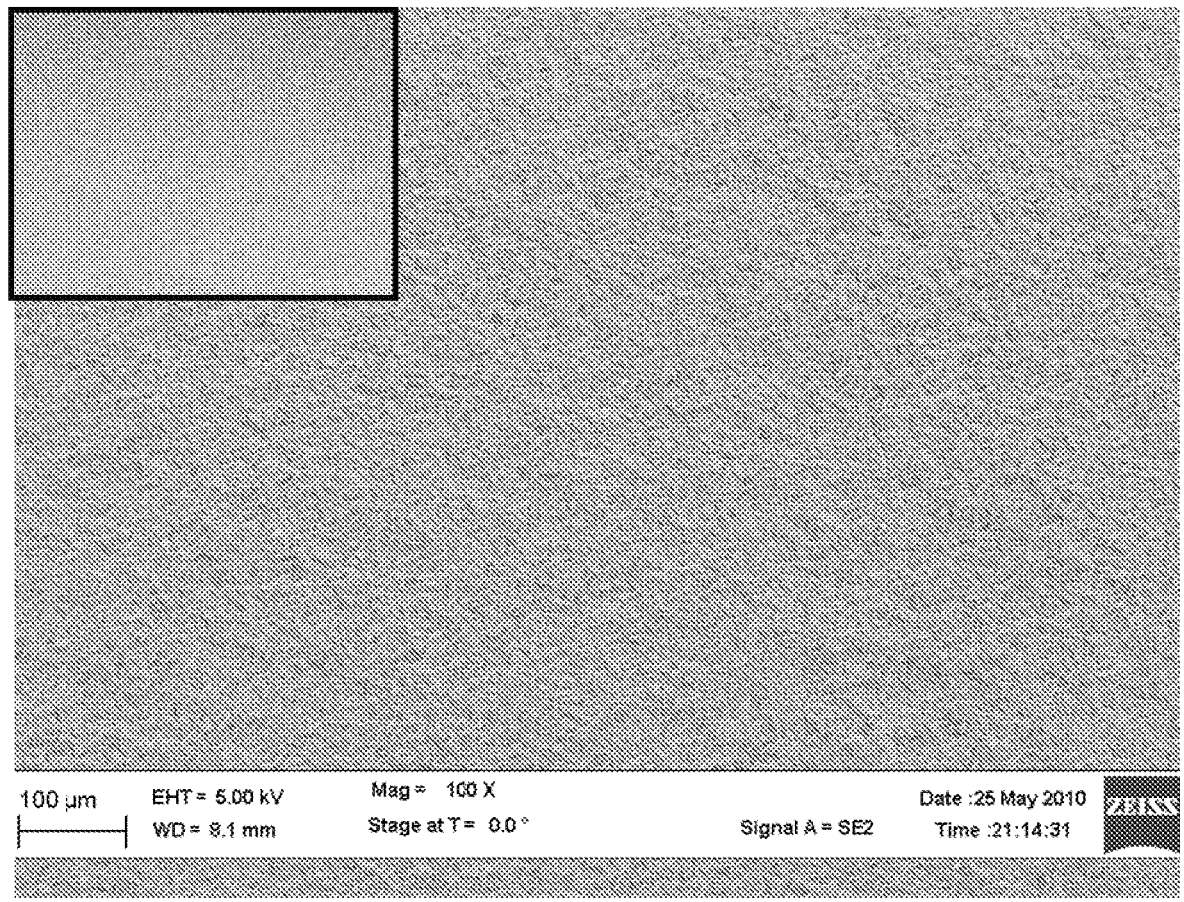
FIG. 27 shows SEM micrographs of NaOH treated and untreated PLGA surface (the inset is untreated one). The micrographs show that nano-textured PLGA has a higher degree of surface roughness.
Figure 28:
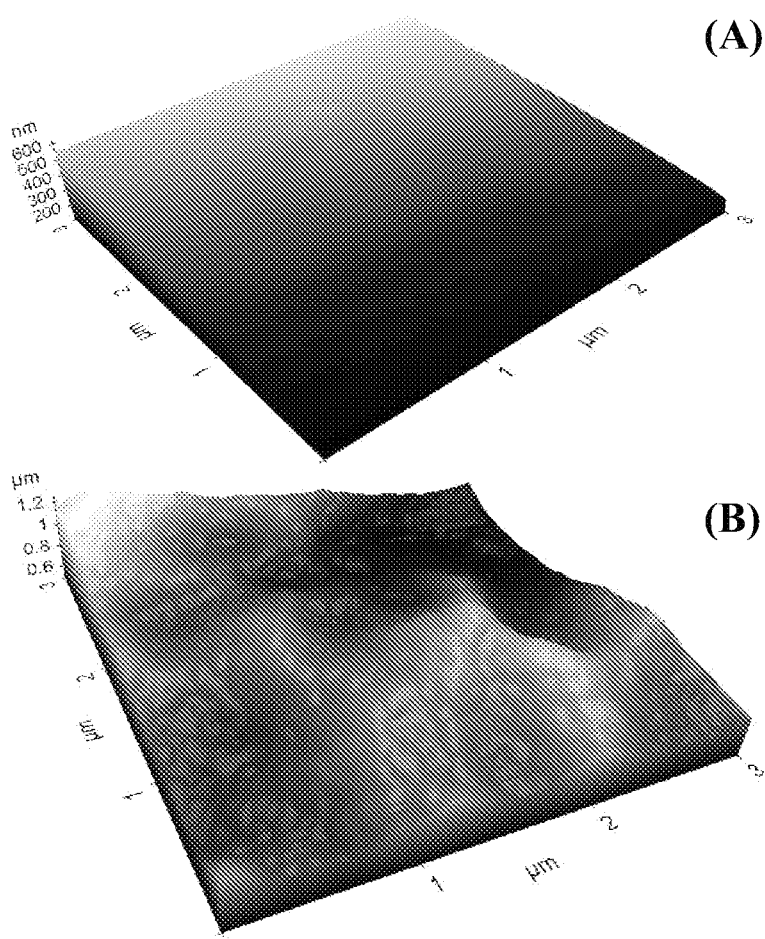
FIG. 28 shows PLGA surface roughness increased after NaOH etching. The AFM micrographs (3×3 µm$^2$) of (A) untreated PLGA; (B) after 10 N NaOH etching for 1 hour. The Surface roughness increased from 22 nm on untreated PLGA surface to 310 nm on nanostructured PLGA surface.

The effects of NaOH concentration and etching times have been previously characterized before. PLGA bulk surface was etched with 10 N NaOH for 1 h to generate nano-textured surface. SEM images of PLGA before and after NaOH etching showed different surface properties (FIG. 27). The untreated one (insert to FIG. 27) was smoother than the nano-textured surface. AFM was used to quantitatively analyze the average surface roughness. AFM micrographs of PLGA substrate showed that NaOH treatment resulted into nano-textured surfaces with an increase in surface roughness and surface area (FIG. 28). Surface roughness increased from 22 nm on untreated PLGA surface to 310 nm on nano structured PLGA surface.

The silanization and isothiocyanate molecule incubations were done for 30 and 20 min respectively. It is important to not to incubate the PDMS substrates for longer periods, as that may cause PDMS bulk to dissolve and swell. Solubility parameters of ethanol and acetone are 12.7 and 9.9 $cal^{1/2}$ $cm^{-3/2}$ respectively, and solvents that have a solubility parameter similar to that of PDMS (7.3 $cal^{1/2}$ $cm^{-3/2}$) generally swell PDMS more. Solubility parameters of methanol and acetonitrile are 14.5 and 11.9 $cal^{1/2}$ $cm^{-3/2}$ respectively, and the swelling ratios are 1.02 and 1.01 respectively, less than that of ethanol and acetone (1.06 and 1.04 respectively). That is why methanol and acetonitrile were used for surface modification. Further, although methanol and acetonitrile can completely dissolve PDMS, the process takes extremely long time. Even diisopropylamine, which has swelling ratio as high as 2.13, still need one month to completely dissolve the PDMS. So in these experiments, the swelling and dissolving factors were insignificant. After the surface modification, the surface roughness did not show any significant changes.

B. Contact Angle Measurements

The contact angle data of a water droplet is frequently used as a measure of the hydrophobicity of a surface. The contact angles of each substratem were measured. The average (n=10) contact angles and standard deviations are shown in TABLE III.

TABLE III

Contact angle measured immediately following substrate UV ozone treatment and chemical activation with PDITC, for each of the substrates employed in this study.

| Substrate Type | Base Substrate | with - |
|---|---|---|
| Glass | 46° ± 1° | 51° ± 1° |
| PDMS No Nano- | 11Table 2. Fluorescence intensity (a.u.) for glass, PDMS | 59° ± 2° |
| PDMS with | 144° ± 4° | 46° ± 3° |

After APTES and isothiocyanate group modification, all three types of substrates showed hydrophilic surfaces. The aptamer immobilization would further decrease the contact angle and making these substrates more hydrophilic. The hydrophilic surfaces are known to have lower protein and cell physical adsorption.

PDMS initially has methyl groups on both side of backbone; after UV ozone treatment, the methyl groups are substituted with hydroxyl groups. The residual methyl groups on the PDMS surface still contribute to the hydrophobicity, as a result, the PDMS surface contact angle is higher than that of glass surface even after APTES and isothiocyanate group modification (TABLE III). Due to increased surface roughness, the nano-textured PDMS substrate has the largest contact angle, but this decreased to a lowest number after APTES and isothiocyanate modification (from 144° to 46°). Due to higher surface roughness the standard deviation of nano-textured PDMS is also higher than that of other groups.

C. Fluorescence Measurements

Fluorescamine is intrinsically non-fluorescent, but its reaction with amino groups results into highly fluorescent derivatives. The relative amount of amino groups on different samples can be determined by comparing the fluorescence intensities of each sample. The average fluorescence intensities of three types of samples are shown in TABLE IV.

TABLE IV

Fluorescence intensity (a.u.) for glass, PDMS and nanostructured PDMS after APTES & fluorescamine modification

| Substrate Type | Fluorescence Intensity (a.u.) |
| --- | --- |
| Glass | 4.7 ± 1.5 |
| PDMS without Nanostructure | 52.7 ± 6.3 |
| PDMS with Nanostructure | 83.9 ± 14.1 |

Nano-textured PDMS shows the highest intensity. On a PDMS chain, two methyl groups can be replaced with hydroxyl groups during the plasma treatment, and the nano-texturing of the surface increases the effective surface area. As a result, the exposure of the surface of PDMS to UV ozone can generate a significantly higher number of hydroxyl groups compared to that on the plain PDMS or glass surface, and so, more amino groups can be introduced on the surface after silanization treatment. The amino group concentration has been shown to reach $4\times10^{-8}$ mol/cm$^2$, and UV ozone treatment can gradually increase the oxygen content percentage (almost 60%) with prolonged treatment. In brief, proper oxidization of PDMS surface can significantly increase the number of hydroxyl groups, and further increase the number of available amino groups from APTES and finally improve the total number of immobilized aptamers. Increased number of available aptamers on the surface is favorable for tumor cell isolation. The substrate anchored DNA probe density can be around 1 per 4-5 nm$^2$ on plane substrates, and higher probe density would decrease the space between 2 adjacent probes. The negative charges from the oligonucleotide functionalized surfaces further inhibit the aptamers from inserting into the spaces between probe molecules and reduce non-covalent adsorption on the surface. However, on nano-textured PDMS surfaces, the larger effective surface area increases the total number of aptamers and the density. It is worth noting that long UV ozone treatment (over 90 min) makes the PDMS stiffer and creates lots of tiny cracks on the surface. In this experiment, the PDMS surfaces were treated for just 30 minutes with UV ozone.

D. Isolation of hGBM Cells

Figure 29:
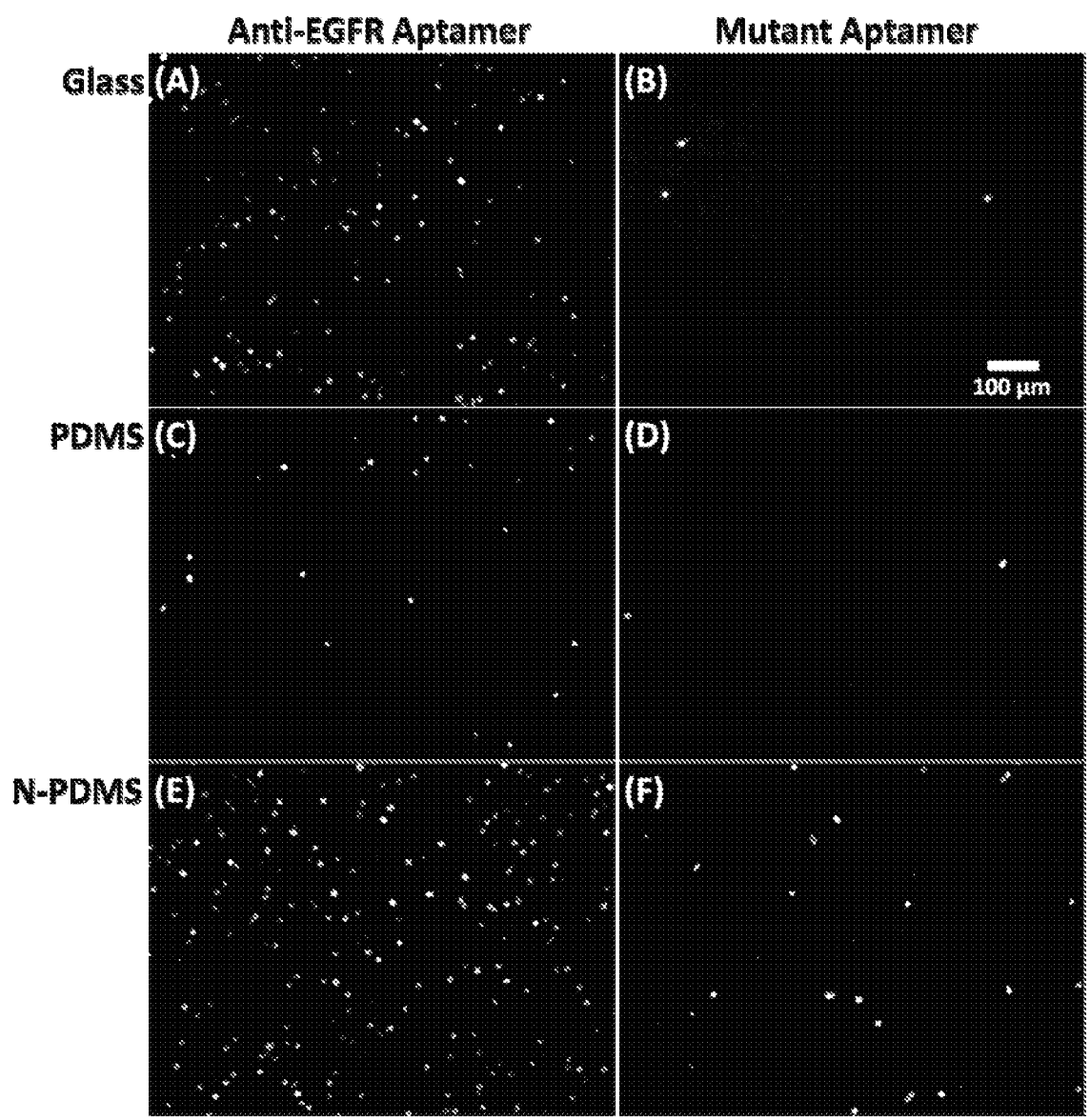
FIG. 29 shows human GBM cells on the anti-EGFR and mutant aptamer modified glass, PDMS and nano-textured PDMS substrates. Substrates were incubated with hGBM and washed with PBS. The hGBM cells densities (per mm$^2$) on the anti-EGFR aptamer modified (A) glass, (C) PDMS and (E) nano-textured PDMS substrates are 79.3 (S.D.: 11.5), 37.4 (S.D.: 10.1), and 149.6 (S.D.: 12.2) respectively; the cell densities on the mutant aptamer modified (B) glass, (D) PDMS and (F) nano-textured PDMS substrates are 2.2 (S.D.: 1.2), 0.6 (S.D.: 0.8), and 25.6 (S.D.: 6.2) respectively; (*$P<0.05$). (G) Plot shows average hGBM cells density on each type of substrate. The table in the inset depicts actual numbers of the plot.
Figure 29:
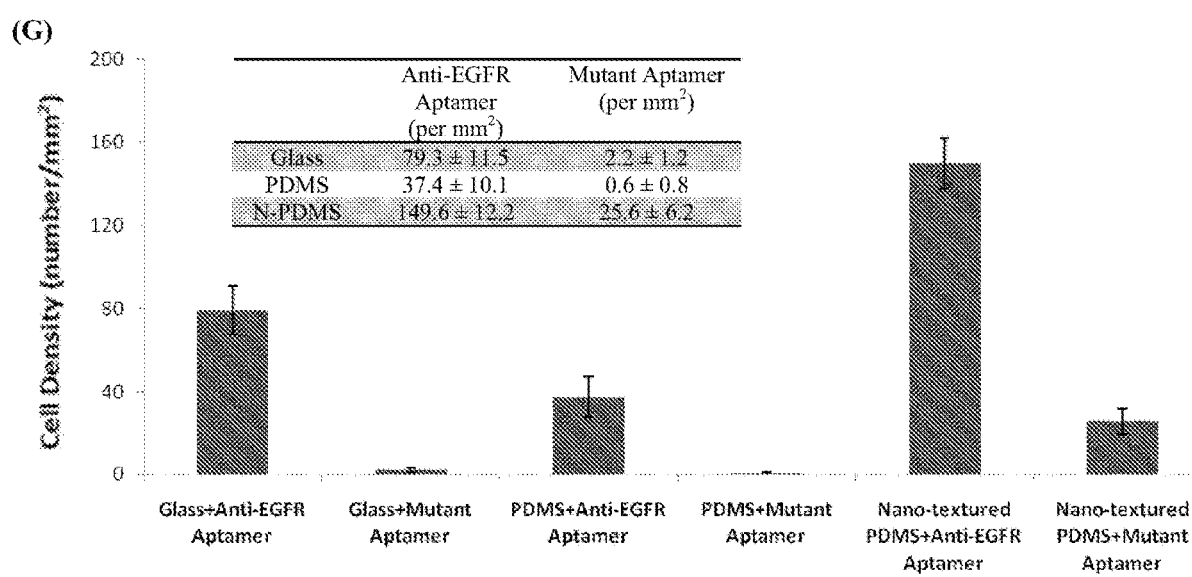
Figure 30:
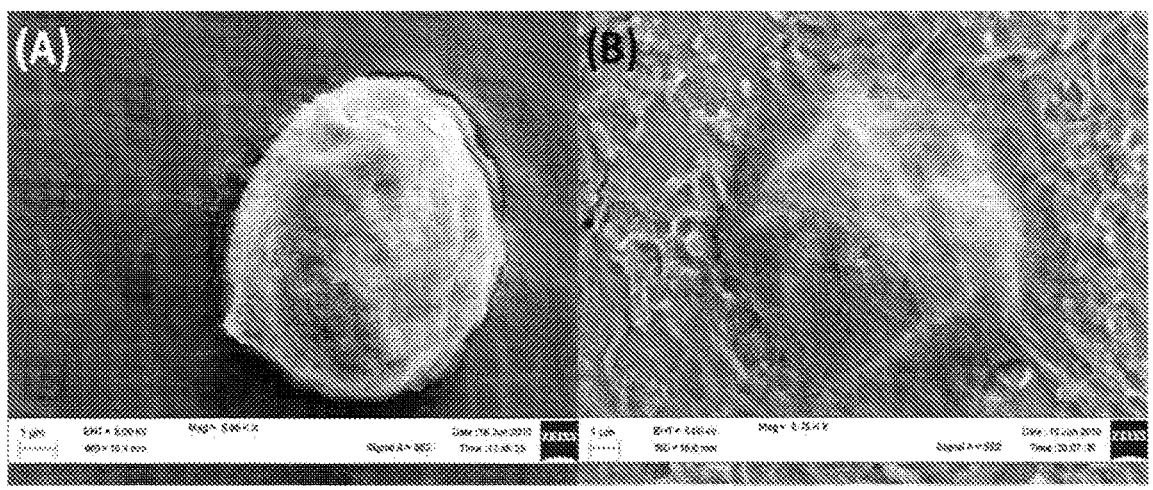
FIG. 30 shows SEM micrographs of captured tumor cell on (A) PDMS and (B) nano-textured PDMS substrate. Images show that cell can firmly attach on the rough surface which mimic the basement membrane structure. The scale bar is 1 µm. Cells were fixed in 4% paraformaldehyde for 3 h, and then the substrates were immersed into 20%, 30%, 50%, 70%, 85%, 95% and 100% (v/v) ethanol concentration gradient solution (15 min in each concentration). All substrates were lyophilized overnight.

FIG. 29 (A) to (F) depict representative images of the hGBM cells captured on glass, PDMS and nano-textured PDMS substrate with anti-EGFR or mutant aptamers. The average density of cells on substrates before washing was 400.9 per mm$^2$ (S.D.: 43.3). All substrates were washed with 1×PBS at 90 rpm for 15 min. Fluorescent images of cells on 10 substrates of each type were taken. The results are shown in FIG. 29 (G) plot. On average 149.6 hGBM cells were captured per mm$^2$ on anti-EGFR aptamer modified nano-textured PDMS substrate (S.D.: 12.2). On the other hand, 79.3 cells per mm$^2$ (S.D.: 11.5) and 37.4 per mm$^2$ (S.D.: 10.1) were captured on anti-EGFR aptamer modified glass and PDMS substrates respectively. There are four major factors which influence the cell capture: the available number of anti-EGFR aptamer molecules on the substrate; the EGFR density on the cell membrane; the affinity between the EGFR and aptamer; and the surface quality of the substrate. It is seen that available number of aptamer molecules is a direct function of surface nano-texturing. Cell isolation efficacy can be improved by increasing the affinity between surface bound aptamer and the over-expressed EGFR. In this case the higher affinity comes from nano-texturing which increases the quantity of aptamers on the surface. The fluorescamine analysis has demonstrated that the nano-textured PDMS can generate more hydroxyl groups after oxidization and therefore more amino groups from APTES can be attached on the surface after silanization. Thus, the density of immobilized anti-EGFR aptamer is increased. In addition, the nano-textured surface mimics the base membrane which facilitates cancer cell attachment. Thus, the number of captured cell on the nano-textured PDMS substrate is higher than other two groups. As discussed before, flat PDMS surface can also generate more hydroxyl groups after oxidization, and a few nanometer rough structuring can be achieved with long UV ozone treatment. However, on flat PDMS surface, even after chemical functionalization, it is still a major challenge to maintain cells on the surface, especially in long-term cell culture on PDMS, because stable cell-adhesive layer is not easy to form. Moreover, the generated hydroxyl groups undergo dehydration reaction and reform Si—O—Si bonds, and the high chain mobility pulls the hydrophobic methyl groups to the surface as well. These two factors can prohibit stable cell-adhesive layer formation. Thus the number of captured cells on PDMS surface is lower than that on glass and nano-textured PDMS surface. This can happen on nano-textured PDMS substrate also, however, the nano-texturing itself provides a trade-off by improving cell attachment and isolation. As the data shows, nano-textured surfaces show improved cancer cell isolation, but the non-specific cell attachment also increases. Increased surface area provides more sites not only for protein adsorption but also for focal contact adhesion sites used by cells to attach onto the surfaces. The nano-textured surfaces are thus better suited for overall cell adhesion goals. In the control group, cell density on mutant aptamer modified nano-textured PDMS substrate is 25.6 per mm$^2$ (S.D.: 6.2), almost 12 times higher than that on glass substrate. Obviously, the higher physical absorption decreases the isolation specificity, but it also significantly improves the detection sensitivity. In practical applications, the selection of material and surface structure depends on the competing goals of isolation sensitivity and specificity. FIG. 30 shows the captured cells on the PDMS and nano-textured PDMS surface. After 30 min incubation, hGBM cells can form pseudopods that indicate cells can firmly attach on the nano-textured PDMS surfaces. The same phenomenon is not seen on smooth PDMS surfaces.

F. Isolation of hGBM Cells from Cell Mixture

Figure 31:
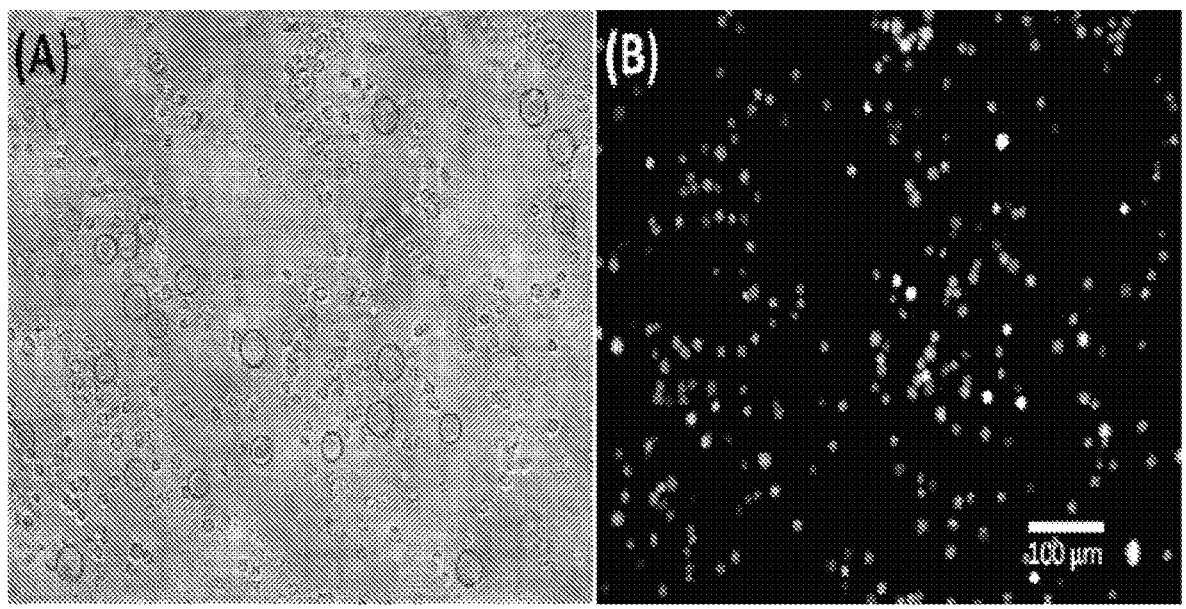
FIG. 31 shows the hGBM cells and fibroblast on the nano-textured PDMS substrates. Substrates were incubated with mixture of hGBM and fibroblast and washed with PBS. (A) and (B) are DIC and fluorescent images respectively from same position. The circles in (A) indicate a few fibroblasts that were captured and cannot be seen in (B).

A mixture of hGBM and fibroblast cells was prepared in a ratio of 1:1, the average cell density on the surface was 332.3 per mm$^2$ (S.D.: 23.6). The substrates were incubated in the cell mixture, washed and imaged. Both DIC and fluorescent images were taken (FIGS. 31(a) and 31(b)). There were about 18.4% hGBM cells from 10 substrates (S.D: 9.1) that did not show any fluorescence. The data from the mixture group showed no fluorescence from about 31% cells from 10 substrates (846 out of 2729 cells, Average: 58.8 per mm², S.D: 21.4). The cells that did not show up in fluorescence images included captured hGBM and non-specifically bound fibroblast cells. The difference of the two percentages, as a first order approximation, shows that on average about 15.4% captured cells were fibroblasts. Thus the anti-EGFR aptamer substrates can selectively isolate and enrich a 1:1 mixture suspension of fibroblasts and cancer cells to 1:5.5 on the surface. In comparison to the previous work on smooth glass substrate, the ratio of hGBM and fibroblast decreases from 1:8.24 (for glass) to 1:5.5 (for nano-textured PDMS). It indicates the nano-textured PDMS substrates also lead to more fibroblast cells attachment. In other works, decreased fibroblast adhesion on nano-textured PLGA substrate after culture was observed. The decreased attachment rate of vitronectin on more hydrophilic NaOH-treated PLGA surface was considered as the primary factor, because the vitronectin—rich PLGA surface is not favorable for fibroblast adhesion. Here, the surface with anti-EGFR aptamer was modified and the mixture cells was incubated for 30 minutes. In other words, it is not believed that vitronectin can effectively attach to the surface in short time and thus further decrease in fibroblast adsorption was expected. The increased number of fibroblasts could then be attributable to the nano-texturing and higher number of available aptamers on the surface which would also bind to the EGFR on fibroblasts' surfaces. Although the nano-textured PDMS substrate increased the attachment of fibroblast, in any case it still could specifically capture hGBM and improve the ratio from 1:1 to 1:5.5. The increased sensitivity decreases its specificity but the trade-off is to the advantage of isolating as many of the small number of cancer cells as possible. In practical applications, the selection of material and surface structure depends on the goals of isolation sensitivity or specificity.

Conclusions

It is demonstrated that anti-EGFR RNA aptamer modified nano-textured PDMS substrates can capture more hGBM cells compared to traditional smooth glass substrates; moreover, the nano-textured PDMS substrate can still specifically recognize, capture and isolate hGBM cells from a mixture of fibroblasts. The nano-textured surface simulates the basement membrane structure and can facilitate tumor cell isolation. This can have important implications for chip-based cancer cell isolation substrate selection.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Example 5

Figure 32:
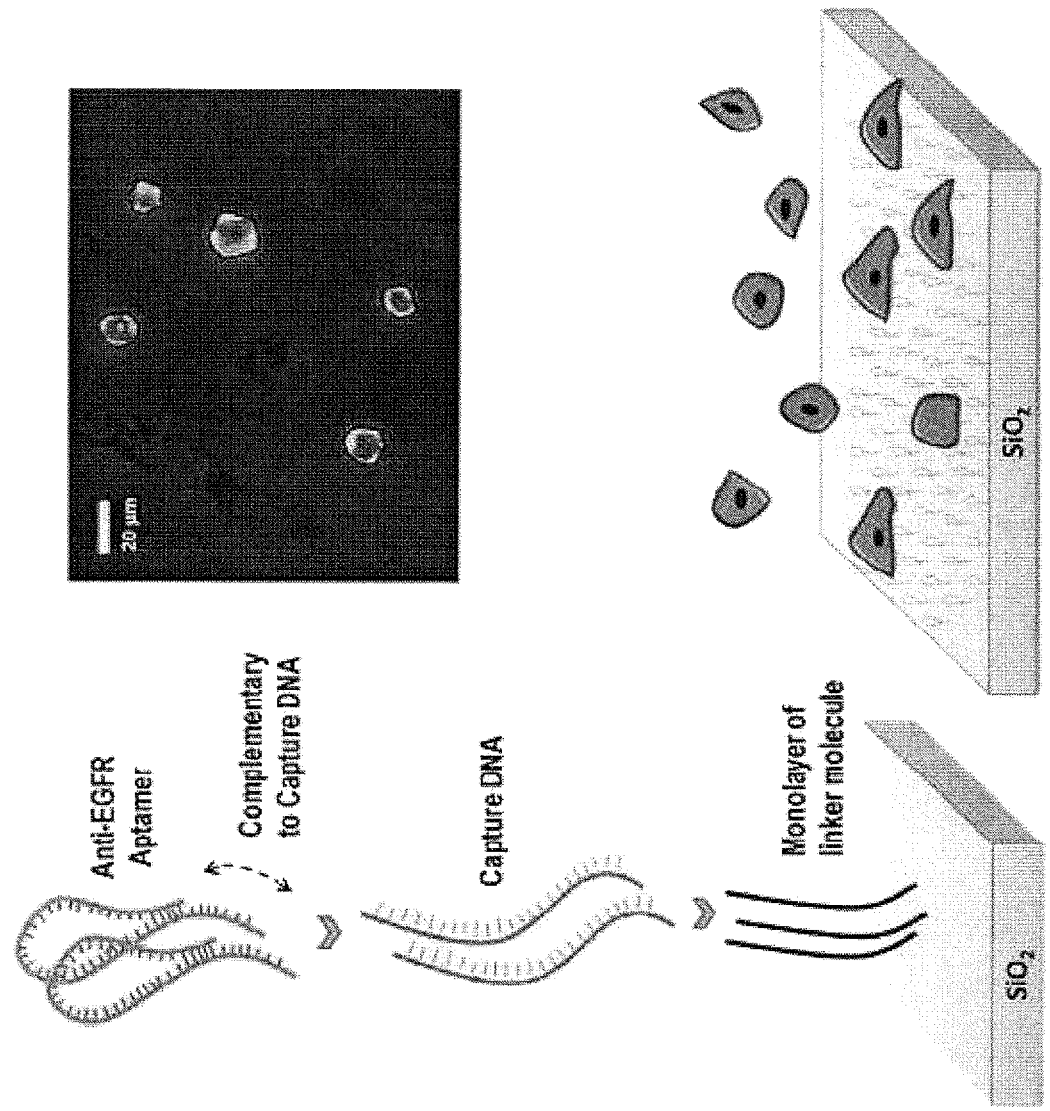
FIG. 32 illustrates steps of a method of detecting tumor cells according to one embodiment described herein.

In this Example, a cytological approach to identify cancer cells based on their dynamic behavior on functionalized surfaces is presented. Aptamers were used to selectively isolate human glioblastoma (hGBM) tumor cells on functionalized substrates (FIG. 32). The hGBM cells are known to overexpress epidermal growth factor receptors (EGFR) and these were specifically distinguished and isolated using anti-EGFR RNA aptamer. During the capture of hGBM cells by the surface-bound aptamers, the cells showed distinct morphological attributes, which were absent in normal cells. Several feature vectors were extracted based on transient morphological changes from the acquired temporal images during incubation. The comparison of the vectors from healthy and diseased cells showed distinctions between tumor and normal cells on the surface.

Methods

The hGBM cells and astrocytes were obtained from consenting patients at the University of Texas Southwestern Medical Center at Dallas, Tex. as per the approved Institutional Review Board (IRB) protocols. Astrocytes are glial cells from the same lineage as hGBM cells. Therefore, comparing hGBM with astrocytes for differentiating between tumor and normal healthy cells gives an accurate and precise comparison, while minimizing other factors that may affect results. Silicon dioxide (glass) surfaces were functionalized with RNA aptamers known to selectively bind to EGFR. Once cells were incubated, the cells got captured. Time lapsed images were taken using an optical microscope and recorded images were analyzed using software described further below. Conventional image processing along with contour detection were used to follow cell behavior. Quantitative data was extracted to compare between control and cancer cells.

A. Selection of Target: Specificity, Selectivity And Sensitivity

EGFRs are overexpressed on tumor cell surfaces with density ranging from 40,000 to 100,000 per cell. This upregulation of EGFR has been associated especially with lung cancer and glioblastoma. Another mutation of EGFR, known as EGFRvIII, has also been observed in lung and glio-carcinomas which was found responsible for cells' proliferative nature. Mutant EGFRvIII results in constant activation of the receptor causing the cells to undergo constant division and thus predisposing the individual to cancer. The EGFRvIII is characterized by a sequence deletion of exon 2-7 (amino acid 6-273). Both types of EGFRs are present on a tumor cell surface but the expression level and the density of the wild type EGFR is much lower (40,000 per cell) than the density of mutant EGFR (approximately a million per cell). It has been shown that anti-EGFR RNA aptamer binds specifically with both mouse derived wild type EGFR and mutant EGFRvIII. In fluorescence experiments that were done for testing the binding ability of the aptamer to EGFR and its variant, mouse glioma cells which were bound to anti-EGFR aptamer showed increased fluorescent activity (60 a.u.) when compared to fibroblast cells (5 a.u.).

A significant amount of mouse-derived tumor cells were captured with anti-EGFR aptamer modified capture substrate. The anti EGFR aptamers had a capturing efficiency (ratio of the number of captured cells to the total number of tumor cells) of 62%. When aptamer and antibody based tumor cell isolations were compared, it was observed that aptamers had higher specificity to tumor cells as compared to the antibodies. It has been shown that the specificity of aptamers on tumor cell capturing is 94.82% as compared to antibody's 68.81%. This specificity of the aptamer can be attributed to its ability to bind to the extracellular ligand-binding domain III of the receptor which is present in both wild type and mutant EGFR. The specific binding of the aptamers to the domain minimizes any chances of non-specific adsorption. Tumor cells have high density of sialylation on their surface as compared to surfaces of normal cells. Increased sialylation gives the tumor cell a net negative charge which is then intuitively repelled by the negative charge of the aptamer, further minimizing non-specific adsorption.

Aptamers selectivity and sensitivity was further improved by using capture oligonucleotide. The capture DNA covalently immobilizes the aptamer on the surface (functionalization). This DNA captures the aptamer, increases the distance between the aptamers and the substrate surface and minimizes any steric and electrostatic hindrance that may arise due to surface tethering. This also increases aptamer's radius of gyration, allowing increased reactivity.

B. Aptamer Preparation

The anti-EGFR aptamer sequence used in this Example was: 5'-GGC GCU CCG ACC UUA GUC UCU GUG CCG CUA UAA UGC ACG GAU UUA AUC GCC GUA GAA AAG CAU GUC AAA GCC GGA ACC GUG UAG CAC AGC AGA GAA UUA AAU GCC CGC CAU GAC CAG-3'. The sequence for mutant aptamer was 5'-GGC GCU CCG ACC UUA GUC UCU GUU CCC ACA UCA UGC ACA AGG ACA AUU CUG UGC AUC CAA GGA GGA GUU CUC GGA ACC GUG UAG CAC AGC AGA GAA UUA AAU GCC CGC CAU GAC CAG-3'; (the extended sequence used to bind to capture DNA is shown in italics). Substrate-anchored capture DNA probe had the sequence: 5'-amine-CTG GTC ATG GCG GGC ATT TAA TTC-3'.

C. Preparation of Anti-EGFR Aptamer Functionalized Substrates

Briefly, the aptamer binding protocol was as follows. First, glass slides were used as substrates and were cut into ~5×5 mm$^2$ pieces. Piranha solution ($H_2O_2$:$H_2SO_4$, 1:3) was used to clean the slides for 10 minutes. The slides were then rinsed with deionized (DI) water and dried in gentle nitrogen gas blow. After drying, the slides were placed for 30 minutes in methanol/DI water (19:1) and 3% APTMS solution. The glass substrates were then washed with DI water and methanol and incubated for 30 minutes at 120° C. A dimethylformamide (DMF) solution was then prepared using 10% pyridine and 1 mmol/L p-Phenylene diisothiocyanate (PDITC). The substrates were then immersed in the DMF solution for 5 hours at 45° C. The substrates were successively rinsed with DMF and 1,2-dichloroethane. After rinsing, the slides were then dried with nitrogen gas. A 30 μmol/L of capture DNA solution with a 5' end amine group was prepared using DI water with 1% N,N-Diisopropylethylamine (DIPEA). The 15 μL of the DNA solution was then placed on each glass substrate. The substrate was then incubated overnight in a humid chamber at 37° C. After incubation the substrates were successively washed with methanol and diethylpyrocarbonate (DEPC) treated DI water. To prevent any non-specific protein adsorption, unreacted PDITC moieties were then capped to deactivate the functional surfaces. This was done by immersing the glass slides for 5 hours in 150 mmol/L DIPEA in DMF and 50 mmol/L 6-amino-1-hexanol. Again, each substrate was sequentially washed with ethanol, DMF, and DEPC-treated DI water. RNase free and DEPC treated DI water was used to properly wash the incubator. In the incubator, a 5 μl of 1 μmol/L anti-EGFR RNA aptamer was placed on each substrate in the presence of 1× annealing buffer [10 mmol/L Tris (pH 8.0), 1 mmol/L EDTA (pH 8.0), 1 mmol/L NaCl]. After being subjected to 2 hours of hybridization at 37° C., substrates were then washed with 1× annealing buffer and DEPC-treated DI water for 5 minutes. A mutant aptamer using the same protocol was hybridized onto control substrates and used as a negative control device. Substrates were then used immediately or stored in 1×PBS (pH 7.5) with 5 mmol/L magnesium chloride solution until used.

D. Fluorescence Measurement

Immobilization of ssDNA and RNA aptamers on the glass surface was verified by fluorescence measurements of Acridine Orange (AO) stain at an excitation wavelength of 460 nm and an emission wavelength of 650 nm. The chip surfaces were prepared as described above and stained at different immobilization steps. In short, AO solution of concentration 2 mg/ml was prepared in sterilized DI water and the samples were completely immersed into it and kept on the shaker for 30 minutes. It was later washed thoroughly with DEPC water before fluorescence measurement. The fluorescence intensity was analyzed with ImageJ software.

E. Isolation and Characterization of hGBM Cells

The hGBM cells were readily placed in ice cold HBSS solution after being taken from the patient's brain. The specimens were, on average, larger than 50 mm$^3$. Lymphocyte-M (Cedarlane labs) was used to remove the red blood cells from the specimen. A solution of 2% papain and dispase was used to gently dissociate the intact hGBM cells, followed by gentle grinding (trituration). A FACS Calibur machine (BD Biosciences) was then used to sort out the cells. Clonal expansion and formation of orthotopic tumors was observed in both CD133+ and CD133− fractions. Cells from the CD133+ fraction were then used in the experiments.

F. Image Processing

Time lapsed optical micrographs were acquired at 30 second intervals using a Leica microscope with DFC295 color camera at 20× magnification. A moving stage microscope was used to image the entire chip. Cell density was measured using a hemocytometer and was optimized at 100,000 cells per milliliter to avoid cells attaching to each other. The images were saved at 4096×3072 resolutions in tiff format.

G. Image Segmentation

Each cell was cropped out using an image segmentation algorithm. The algorithm provided an approximation of the center of the cell body. Based on the image magnification of the microscope, a 200×200 pixel cropping was performed around the estimated center. This cropping kept a typical cell completely inside the frame. Images where two or more cells were seen clumped together were discarded. Less than 5% of images showed such clumping behavior of cells. The number of pixels was optimized to increase the speed as well as to retain the required information.

H. Contour Detection

Figure 33:
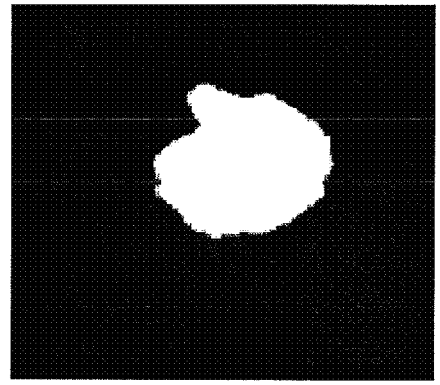
FIGS. 33-36 each illustrates a step of a method of detecting tumor cells according to one embodiment described herein.
Figure 33:
Figure 33:
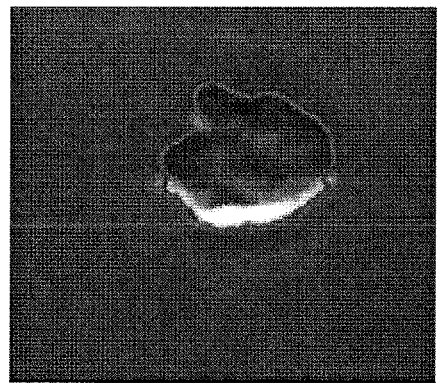
Figure 33:
Figure 33:
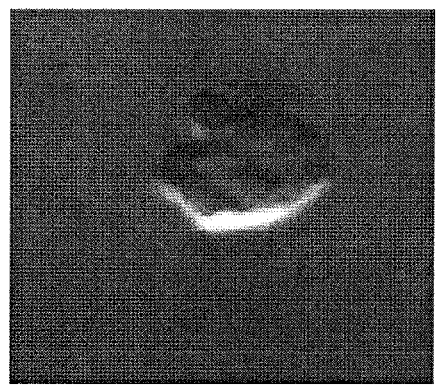

After initial Wiener filtering, contrast enhancement and smoothing, separated cell image contours were detected using "level set" algorithm, as described in Sethian, J. A. (1996) *Proceedings of the National Academy of Sciences* 93, 1591. Energy parameters were defined for each image and an initial contour was estimated. A recursive algorithm was developed to minimize the total energy in the equation. Minimum energy occurred at the cell membrane of the image where change in contrast from pixel to pixel became the largest. Contour image plot was then converted to binary format for further analysis. Binary morphological image processing functions 'erode' and 'dilate' were used to eliminate spurious pixels. The cellular region in the binary image was represented as white and the rest of the frame was represented as black (FIG. 33). This conversion made it suitable to statistically analyze the extracted data, without losing any important morphological information.

I. Feature Extraction

Figure 34:
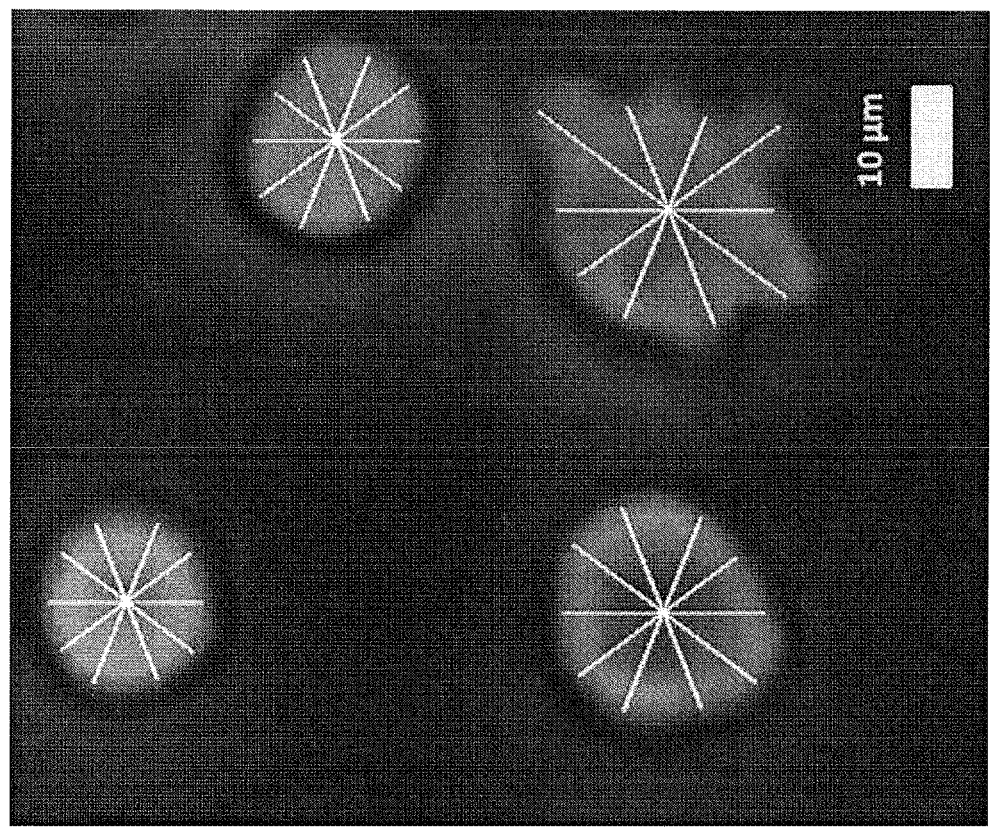

Centroids for all cells were determined by taking average pixel count in both horizontal and vertical directions. Cell membrane distance from the center was calculated at a resolution of 24 degrees (FIG. 34). A total of 15 radii were calculated for each cell. Resolution was optimized to maximize the differences in the radii. Too low a number would have missed important data, whereas more number of radii would have failed to amplify the differences between successive radii.

Cancer cells showed random shape changes after capture on the surface. The shapes changed from oval to elliptical, and then highly non-uniform shapes with multiple pseudopods emerged. The shape randomness was tracked from frame to frame for each cell. Non-uniformity of cells was calculated from the differential of two successive radii. For two successive radii, $r_n$ and $r_{n+1}$, the differential ($\Delta r$) was $\Delta r = r_n - r_{n+1}$. An empirical threshold was determined to amplify the differential (where the amplified differential is $\Delta r'$), and a non-uniformity parameter (N.U.) was then calculated. These steps are described by equations (1) to (3) below:

$$\Delta r_n = r_{n+1} - r_n; \quad (1)$$

$$\Delta r' = \begin{cases} 0 & \text{if } (\Delta r) < 9 \text{ pixels} \\ (\Delta r)^2 & \text{if } (\Delta r) > 9 \text{ pixels} \end{cases}; \text{ and} \quad (2)$$

$$\text{non-uniformity}(N.U) = \sum_{n=1}^{N-1} (\Delta r'). \quad (3)$$

"Hausdorff distance" is a standard measure to determine the variation from one image to another by calculating and comparing point-to-point distance between contours. Hausdorff distances between cells in two consecutive frames were thus measured based on pixel level information, as described in Huttenlocher et al. (1993) "Pattern Analysis and Machine Intelligence," *IEEE Transactions* on 15, 850-63. This approach calculated the maximum value among all minimum distances between any two possible point sets on the two cell membranes. A comparison was made frame by frame for healthy and cancerous cells.

Pseudopods were computationally defined as an extension of the membrane over a threshold multiplier of the average radius. Such extensions were calculated and tracked for a 360 degree rotation of radius for every frame. Cancer cells showed random extension and contraction of pseudopods, whereas normal cells remained still and did not show much activity. Hence change in number of pseudopods over time was an important discriminating factor in this context. The rate of change in number of pseudopods from frame to frame was thus calculated. An extension was considered a positive change and its contraction was counted as negative. Formation of pseudopods at different angles was measured and recorded to keep track of the cell wall changes.

Results and Discussion

Figure 35:
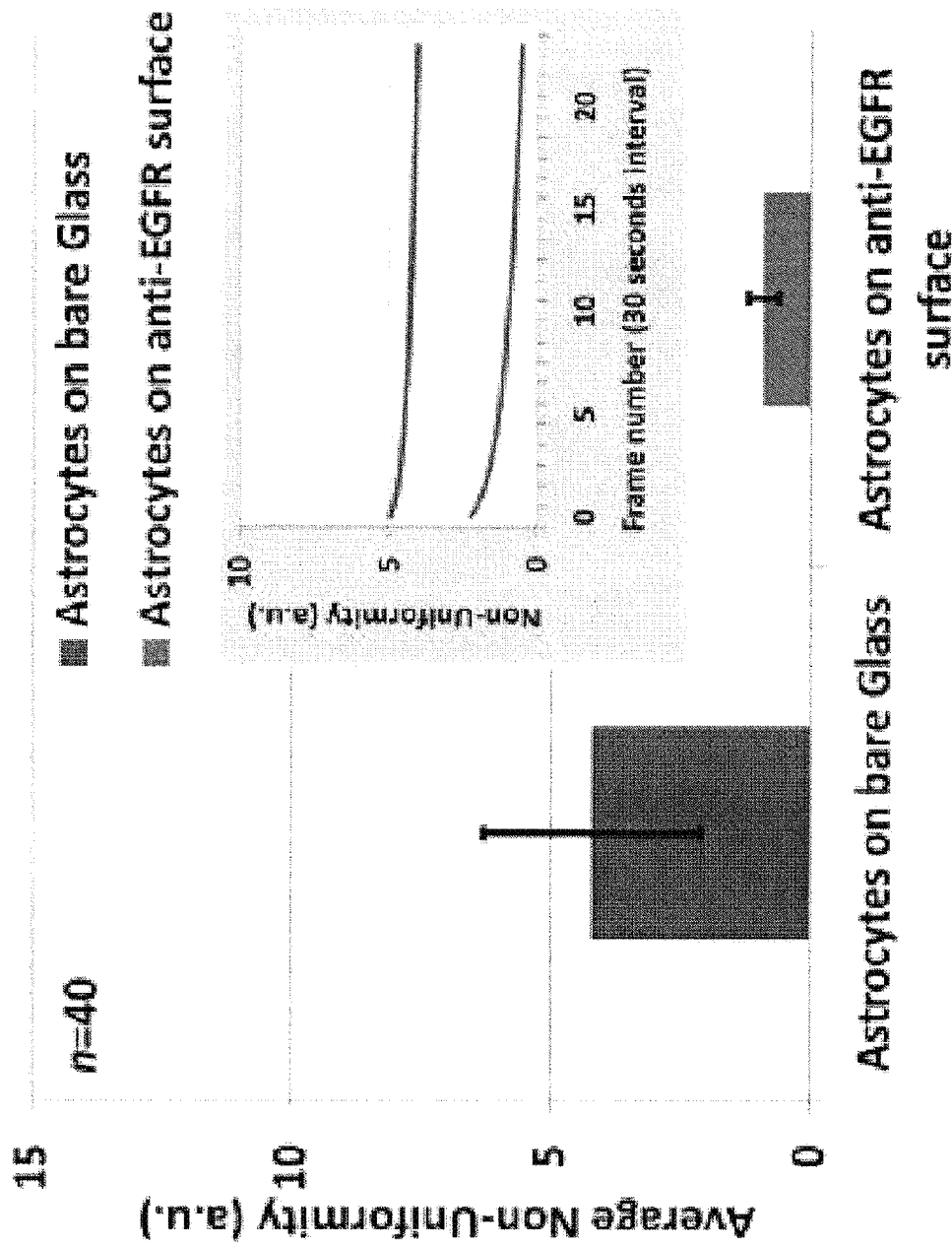

As described above, the RNA aptamers on the surface created a passive monolayer that inhibited regular cell-surface interaction through adhesion molecules. On bare glass, astrocytes indeed interact with the surface, though at a much reduced pace. A comparison of astrocytes cell-surface interaction on a piranha cleaned bare glass and a RNA functionalized glass substrate is presented in FIG. 35.

However, such surfaces may introduce non-specific cell activity and false detection. Because of the RNA monolayer, while the other modes of cell-surface interaction are disabled, only the complementary molecules on the cell membrane can possibly interact with the surface. Hence it can be important to ensure a uniform and dense monolayer to inhibit non-specific interaction. Binding of probe DNA and RNA to the substrate was verified through staining by acridine orange.

In all cases, before incubating on the substrates, cells were centrifuged and the supernatants were removed. Sterilized 1×PBS solution (with 5 mmol/L $MgCl_2$) was added to dilute the cells. The functionalized slides were placed in PDMS wells and 0.5 ml cell solution was placed on each substrate to make sure it was completely submerged. After 3-4 minutes of settling, images were captured at 30 seconds interval. The period was optimized to capture maximum activity and to minimize processing overhead. Tumor cells on the aptamer modified surfaces showed enhanced activities (shape changes with time, non-uniformity, and formation of pseudopods etc.) while attaching to the surface. All four kinds of samples (two anti-EGFR modified surfaces and two surfaces modified with mutant aptamers) were measured on the same day. The cells were taken out of the incubator and kept at 37° C. The experiment was done both inside and outside an incubation chamber, and negligible differences were observed during the short time of imaging. However, complete data acquisition process was done within 20 minutes to minimize artifacts from unwanted cell deaths.

After image acquisition, each cell image was separated out and contours were detected. On average, the time for such contour detection depended on a number of factors such as the microscope light and aperture size. These factors were optimized to enhance the edge contrast of the cells which resulted in more efficient and faster processing speed, as a lower number of computational iterations were needed. The algorithm could be tuned for computing either smoother surfaces of the binary images or faster processing speed. For rapid processing, the edges were kept slightly rough. The roughness eventually averaged out over the whole membrane and minimally affected the extracted data.

During the processing, most errors occurred due to limitations on the depth of field of the imaging microscope. When a pseudopod extended, the boundary of the pseudopod region went slightly out of focus and this created some distortions. Sequential images of 100 regions, each measuring the changes in the cell contours over time, were taken on a moving-stage microscope to ensure cell activity was recorded across the whole surface of the chip. The analysis of the 100 regions showed statistically different behavior between cancer and normal cells.

There were four combinations of cells and functionalized surfaces: (i) hGBM cells+anti-EGFR aptamer surface, (ii) Astrocytes+anti-EGFR aptamer surface, (iii) hGBM cells+mutant aptamer surface and (iv) Astrocytes+mutant aptamer surface. The last three combinations acted as controls for the experiments. Every cell in a frame was tracked and underwent image processing and data analysis. Non-uniformities and Hausdorff distances for the four combinations were calculated.

Figure 36:
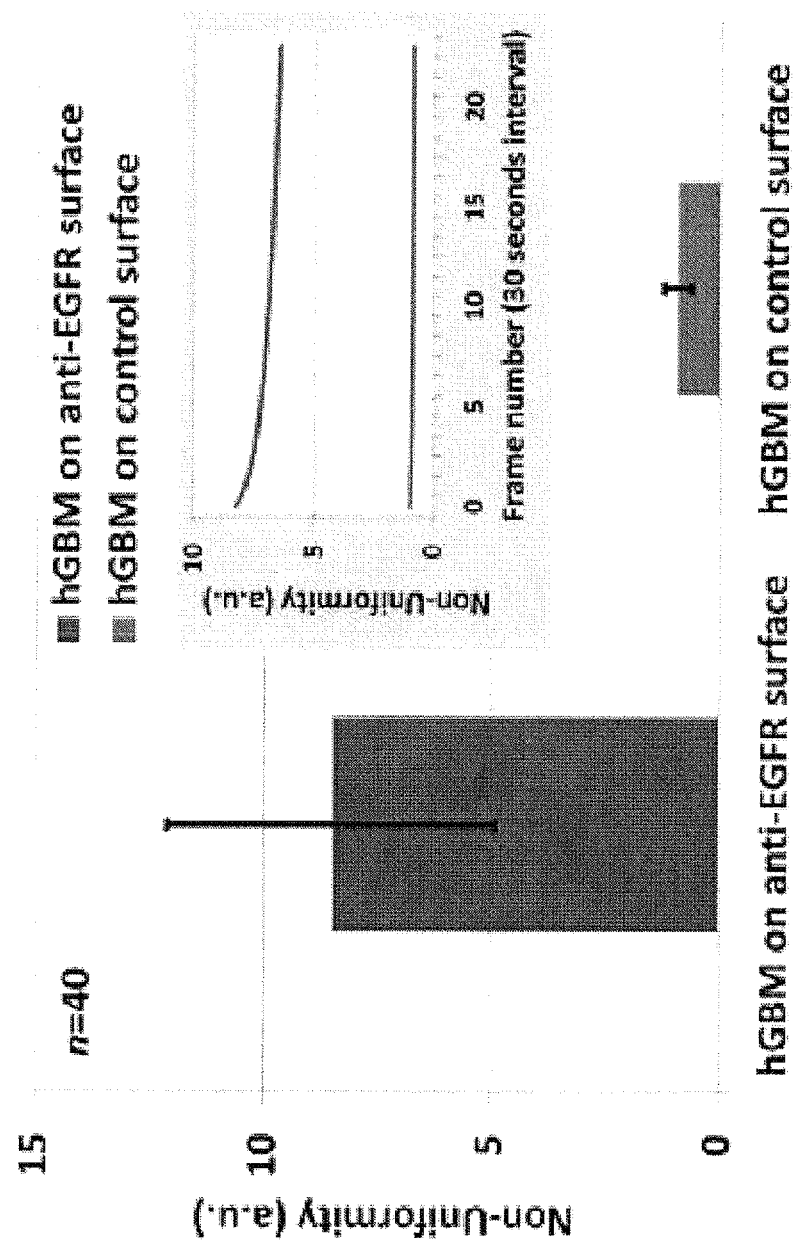

The hGBM cells on anti-EGFR aptamer surface showed much higher nonuniformity in their surface contour over the period of image acquisition. The same cells remained inactive on a non EGFR-specific mutant aptamer coated surface (FIG. 36). In addition, as described above, the control cells (astrocytes) also do not show such activity or morphological changes on the EGFR-specific surface. Enhanced activity of the cancer cells on the surface resulted in higher cell nonuniformity. Over 25 frames, tumor cells showed nonuniformity ranging from 8-10 (a.u.) on average, whereas in the controls for other combinations, this remained below 1 (a.u.), thus providing a non-uniformity factor of greater than 8-10 (where the "non-uniformity factor" is the ratio of the non-uniformity of the tumor cells compared to the non-uniformity of the control cells when measured as described herein). In some cases, the non-uniformity factor is about 2-100, 2-50, 2-20, 5-100, 5-50, 5-20, 5-10, 10-100, 10-50, or 10-20.

Figure 37:
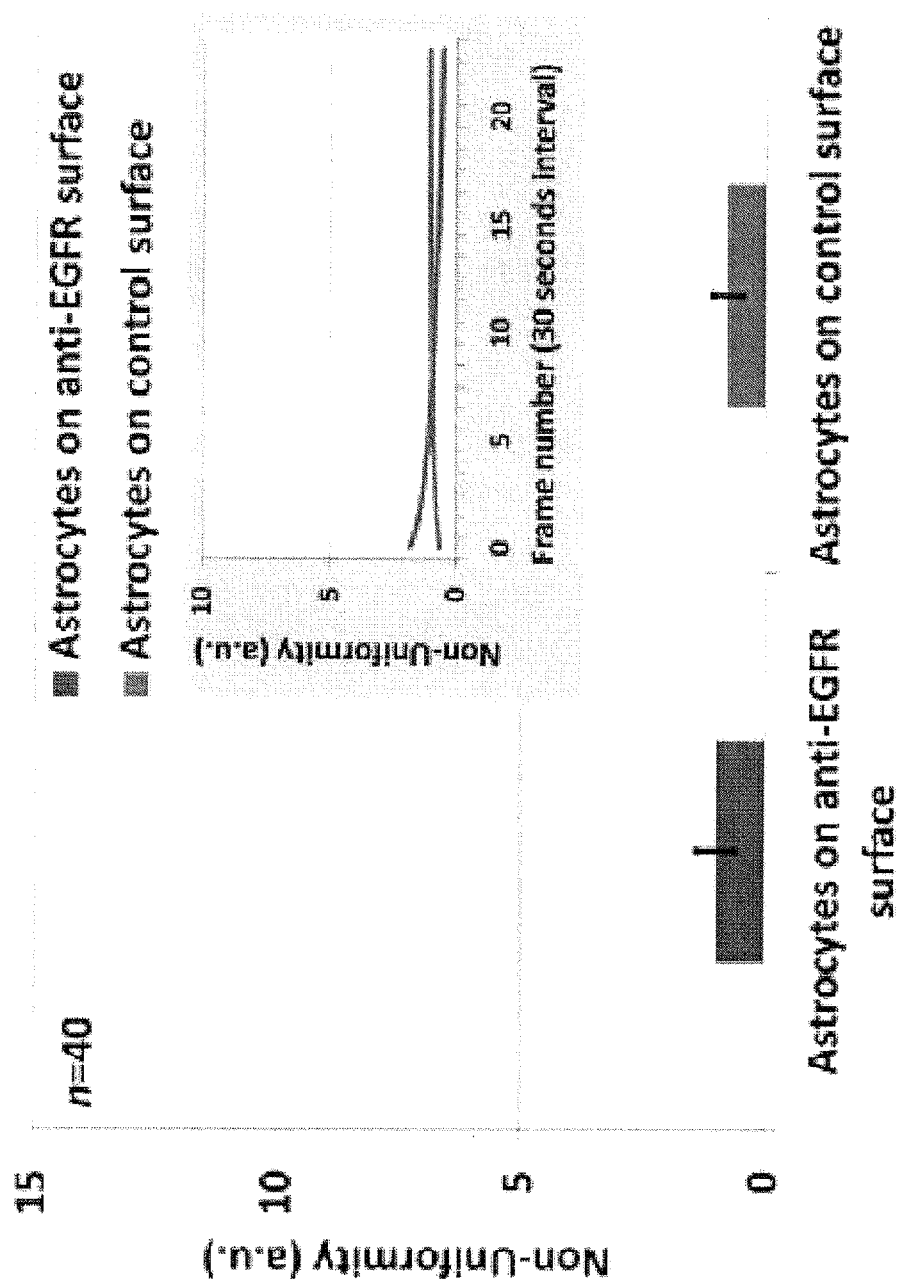
FIG. 37 illustrates comparative data regarding a method of detecting tumor cells according to one embodiment described herein.

To verify whether such activity was EGFR specific, in a separate experiment, astrocytes cells were incubated on both the anti-EGFR and the mutant aptamer coated control surfaces. These cells showed negligible activity on the surfaces (FIG. 37). This result indicates that the surface was indeed passivated by the RNA layer and a complementary ligand on the surface can activate the cell towards shape changes. Such activity might could also be triggered by a complementary antibody layer on the surface.

Figure 38:
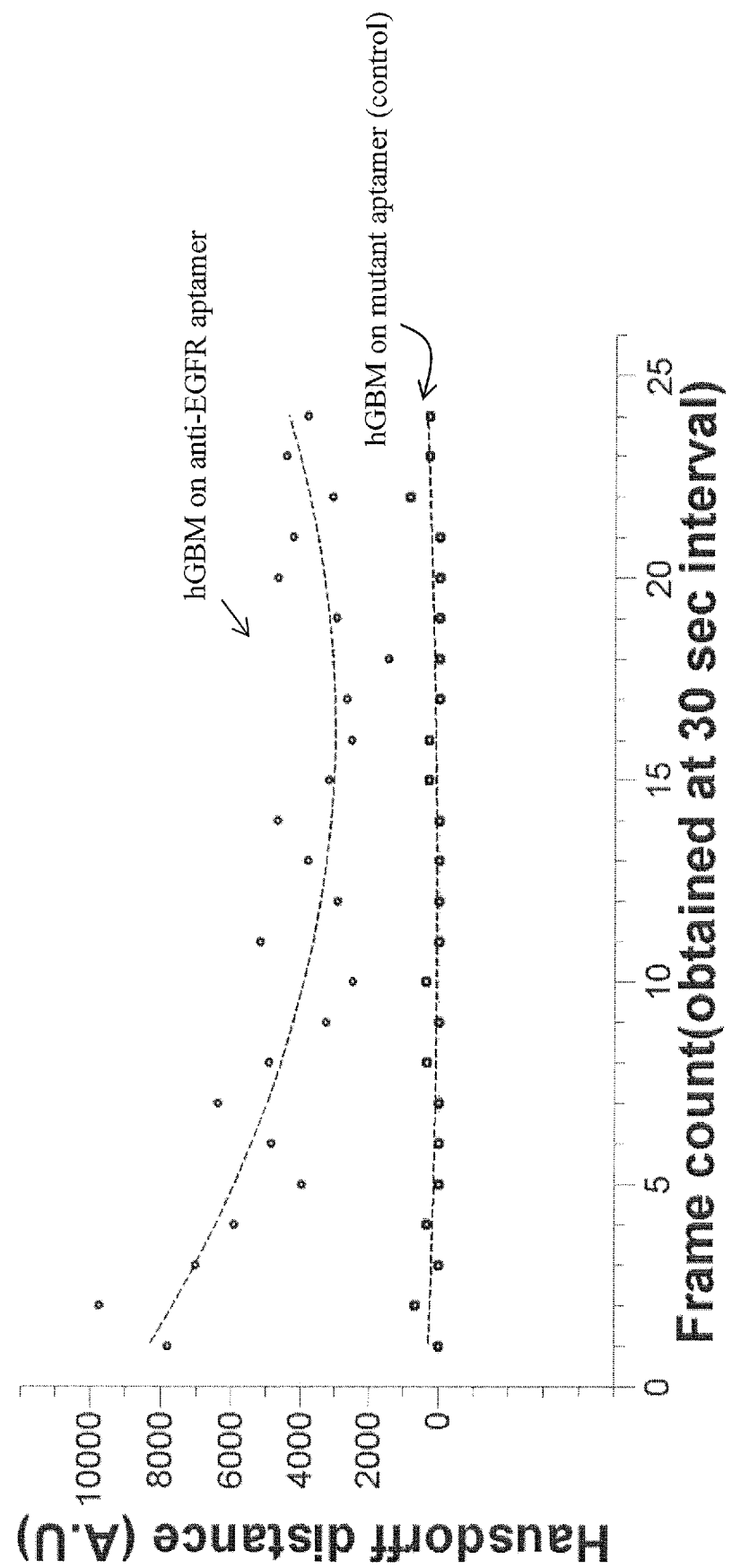
FIGS. 38 and 39 each illustrates data regarding a method of detecting tumor cells according to some embodiments described herein.

The Hausdorff distance between the contours of cells also showed distinguishing behavior, as illustrated in FIG. 38. The tumor cells on the anti-EGFR aptamer surfaces consistently showed higher Hausdorff distances compared to the controls. On average, the Hausdorff distance was calculated to be 4500 (a.u.) for tumor cells whereas for control combinations, it stayed around 200 (a.u.), thus providing a Hausdorff distance factor of about 22.5 (where the "Hausdorff distance factor" is the ratio of the Hausdorff distance of the tumor cells compared to the Hausdorff distance of the control cells when measured as described herein). In some cases, the Hausdorff distance factor is about 2-100, 2-50, 2-40, 5-100, 5-50, 5-30, 10-100, 10-50, 10-40, 10-30, 20-100, 20-50, 20-40, or 20-30.

The rates of change of pseudopods between frames are shown in TABLE V. On average, the tumor cells on anti-EGFR aptamer surface showed pseudopods forming at different locations on the wall of the same cell as seen in consecutive frames. There was constant formation and contraction of pseudopods. Each contraction was considered as a change of −1 while formation of a new pseudopod was counted as +1. On the other hand, control combinations showed minimal changes in cell contour. Even if there were pseudopods at start, these stayed at the same orientation in all subsequent frames.

TABLE V

| Cell and surface combination | Differential Change over 25 frames |||||||||| 
| | Data set no. |||||||||| 
| | 1 | 2 | 3 | 4 | 5 | 6 | 7 | 8 | 9 | 10 |
|---|---|---|---|---|---|---|---|---|---|---|
| Astrocytes on anti-EGFR aptamer | 0 | 0 | 0 | 0 | 5 | 3 | 2 | 5 | 0 | 1 |
| Astrocytes on mutant aptamer | 0 | 0 | 3 | 0 | 0 | 4 | 0 | 0 | 1 | 0 |
| hGBM on anti-EGFR aptamer | 20 | 7 | 28 | 12 | 6 | 11 | 9 | 7 | 5 | 14 |
| hGBM on mutant aptamer | 0 | 0 | 1 | 0 | 0 | 0 | 0 | 0 | 1 | 0 |

Cell motility is a natural phenomenon, where cells move by protruding a section of the membrane. This complex process is accomplished by sophisticated force balancing acts between internal cytoskeleton structures, adhesion molecules and the cell membrane. Cytoskeleton structures works in coordination of actin filament, microtubules, and tubulin protein. Major force contribution comes from the actin filament that polymerizes and thus changes length in response to physical and chemical stimuli. Depending on the actin concentration on the membrane, several nano-Newtons of force on the membrane is applied by the actin filament structure. This force is calculated from the association/disassociation constant of the actin monomer to the filament. On the other hand, the membrane molecules are dynamic in nature due to Brownian motion and are flexible when subjected to external force. Different models such as ratchet models and autocatalytic models have been proposed to describe molecular mechanisms of actin force generation and protrusion of the leading edge.

Flexibility of the cancer cell membranes are reported to be higher than the healthy cells due to their inherent weak structures. Because of overexpression of several proteins on the membrane of cancer cells, the balancing forces between the cytoskeleton and the membrane protein are different than healthy cells. The hGBM cells, with strong overexpression of the EGFR, when seeded on a surface functionalized with anti-EGFR aptamer have an added parameter in the force balancing equation. The surface passivation due to anti-EGFR aptamer coating on the surface reduces adhesion while the binding interaction between EGFR and anti EGFR aptamer interaction enhances the membrane protrusion. This leads to enhanced cell movement activity. However, having no certain directional signaling, cells do not show significant translational movement.

Conclusion

The foregoing Example illustrates that quantitative differences in the interactions of normal and tumor cells on functionalized surfaces can be used as a rapid cytological indicator of cancer cells. By using appropriate image processing techniques in combination with suitable surface preparation, a detection method for tumor cells can be implemented. Thus, methods described herein, in some embodiments, can serve as an additional modality to support histological findings and/or to identify tumor cells based on their physical behavior from blood samples or biopsy specimen drawn directly from patients.

Example 6

In this Example, a method of differentiating tumor cells from non-tumor cells was carried out in a manner similar to that described above in Example 5.

Materials and Methods

Nanotextured and plain glass slides were used for cancer cell isolation. In either case, the surfaces were functionalized with anti-EGFR aptamer through multi-step layer by layer assembly of molecules, as described above. First, the slides were cleaned with Piranha solution ($H_2O_2:H_2SO_4$, 1:1) followed by silanization. A single-stranded DNA (ssDNA) sequence was then attached to the surfaces through a homobifunctional linker. The linker would bind to the silane on one end and the amine group of ssDNA on the other end. After ssDNA attachment and blocking of unreactive linker functional groups, anti-EGFR RNA was hybridized to the ssDNA on the chips. After incubating the chips with tumor cell mixtures, time lapsed images were taken.

These recorded images were then processed though several steps towards final contour detection. After initial image enhancement, cell boundaries were detected and images were converted to binary format for processing. The temporal changes in contours of cells from frame to frame gave information like size, the change in cell boundary, the growth, and the formation of pseudopods. Based on these features several feature vectors were defined that would differentiate one cell type from the other, as described further herein.

The image enhancement operations showed dependence of the computation speed on a number of factors (e.g., the density of cells in a frame, the frequency of frame capture by the camera, the depth of field of the imaging plane, the resolution of the captured image, and the ability to reimage the same cell (or set of cells) at exactly same position). The processes consisted of tone detection (dark versus bright areas), identification of bright region (cell tagged), segmentation (conversion to binary image), angular sectoring (to breakdown circular cell into parts), boundary tracing (cell growth and motility) and detection of protrusions (pseuodpods).

Results

Figure 39:
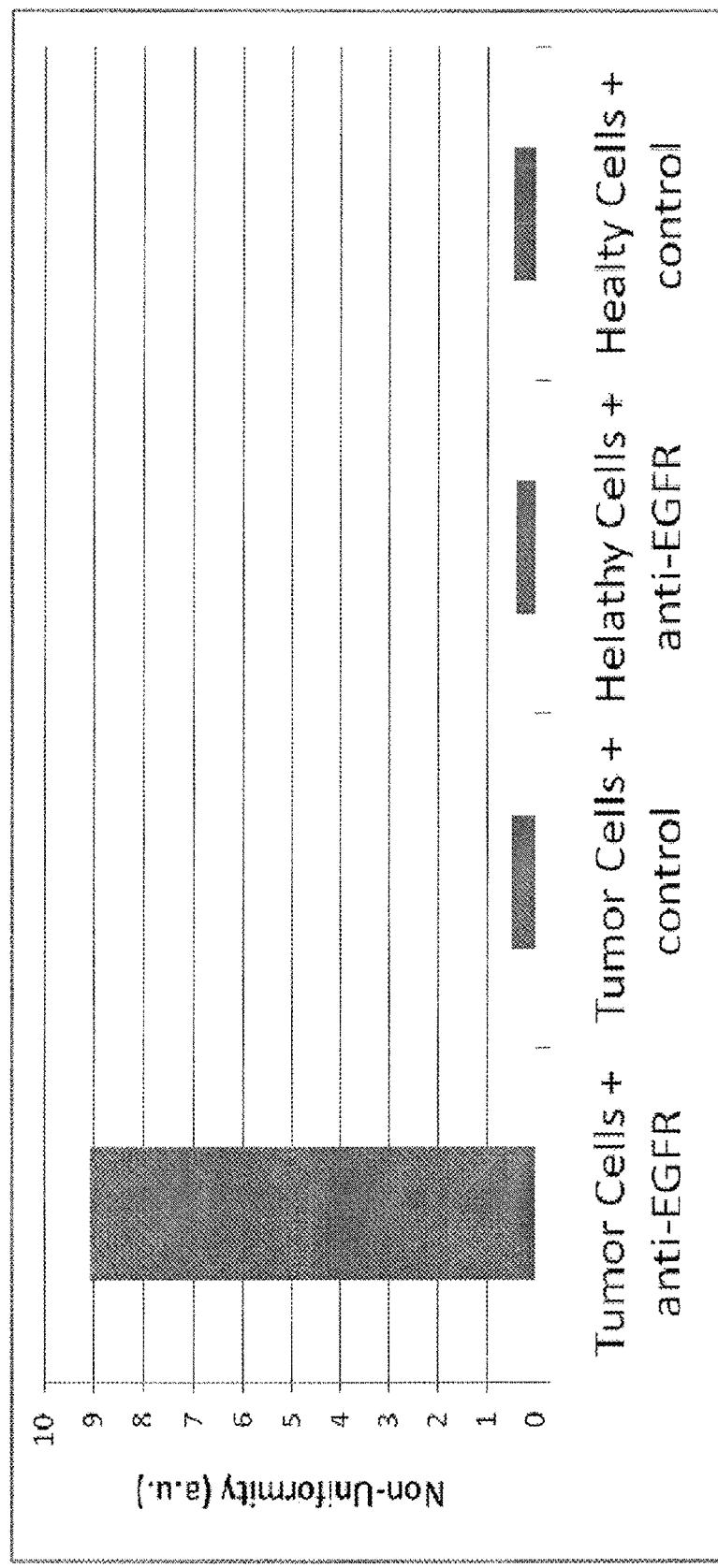

EGFR-specific aptamers selectively isolated EGFR overexpressing human glioblastoma (hGBM) cells with high specificity. Tumor cells, when bound to such functionalized surfaces, showed distinct morphological patterns and enhanced activity as compared to healthy cells, which remained calm. These cells showed clear changes in cell shapes from spherical to semi-elliptical with very flat orientation, formed pseudopods (possibly to cover much more surface area) and showed rapid growth. Cell behavior on both EGFR-specific surface and control surface was quantified and different feature vectors like non-uniformity (FIG. 39), Hausdorff distance, frame-to-frame differential pseudopod formations were calculated. The non-uniformity feature was based on the formation of finger-like projections protruding out of the cell walls. This also made the focal point move and required manual focusing of the microscope. A frequency of 4 images per minute was found to be optimal to essentially capture the slow movements of the cells.

That which is claimed is:

1. A method of detecting tumor cells comprising:
   providing a device, the device comprising:
   a substrate surface; and
   a plurality of first aptamer probes attached to the substrate surface;
   contacting a plurality of cells with the plurality of first aptamer probes attached to the substrate surface;
   adhering one or more of the plurality of cells to the substrate surface; and
   measuring a Hausdorff distance of at least one adhered cell.

2. The method of claim 1 further comprising using the Hausdorff distance of the adhered cell to identify the adhered cell as a tumor cell or a non-tumor cell.

3. The method of claim 1, wherein the substrate surface is formed from glass, silicon, or a polymer.

4. The method of claim 1, wherein the plurality of first aptamer probes forms a uniform or substantially uniform coating on the substrate surface.

5. The method of claim 4, wherein at least about 80% of the substrate surface is coated by the plurality of first aptamer probes.

6. The method of claim 1, wherein the plurality of first aptamer probes comprises an anti-EGFR aptamer.

7. The method of claim 1, wherein the plurality of cells comprises tumor cells.

8. The method of claim 7, wherein the tumor cells comprise circulating tumor cells.

9. The method of claim 7, wherein the tumor cells comprise breast cancer cells, cervical cancer cells, lung cancer cells, bladder cancer cells, ovarian cancer cells, esophageal cancer cells, head and neck cancer cells, kidney cancer cells, glioma cells, bladder cancer cells, pancreatic cancer cells, colon cancer cells, or a combination thereof.

10. The method of claim 1, wherein the plurality of cells comprises a mixture of tumor cells and non-tumor cells.

11. The method of claim 1, wherein contacting a plurality of cells with the plurality of first aptamer probes comprises contacting a bodily fluid with the plurality of first aptamer probes.

12. The method of claim 11, wherein the bodily fluid comprises blood, saliva, urine, or bladder wash.

13. The method of claim 10, wherein more than one cell is adhered to the substrate surface and the adhered cells exhibit a Hausdorff distance factor of 2-100, the Hausdorff distance factor being a ratio of the Hausdorff distance of the adhered tumor cells compared to the Hausdorff distance of the adhered non-tumor cells.

14. The method of claim 1, wherein the substrate is formed from silicon.

15. A method of detecting tumor cells comprising:
providing a device, the device comprising:
a substrate surface; and
a plurality of first aptamer probes attached to the substrate surface;
contacting a plurality of cells with the plurality of first aptamer probes attached to the substrate surface;
adhering one or more of the plurality of cells to the substrate surface; and
measuring a change in the number of pseudopods of at least one adhered cell.

16. The method of claim 15, further comprising using the change in the number of pseudopods of the adhered cell to identify the adhered cell as a tumor cell or a non-tumor cell.

17. The method of claim 15, wherein the substrate surface is formed from glass, silicon, or a polymer.

18. The method of claim 15, wherein the plurality of first aptamer probes forms a uniform or substantially uniform coating on the substrate surface.

19. The method of claim 18, wherein at least about 80% of the substrate surface is coated by the plurality of first aptamer probes.

20. The method of claim 15, wherein the plurality of first aptamer probes comprises an anti-EGFR aptamer.

* * * * *